(12) United States Patent
Miles et al.

(10) Patent No.: US 8,167,894 B2
(45) Date of Patent: May 1, 2012

(54) METHODS, SYSTEMS AND DEVICES FOR REDUCING THE SIZE OF AN INTERNAL TISSUE OPENING

(75) Inventors: Scott D. Miles, Sandy, UT (US); Clark C. Davis, Holladay, UT (US); DeWayne C. Fox, South Jordan, UT (US); Daryl R. Edmiston, Draper, UT (US); Richard J. Linder, Sandy, UT (US)

(73) Assignee: Coherex Medical, Inc., Salt Lake City, UT (US)

( * ) Notice: Subject to any disclaimer, the term of this patent is extended or adjusted under 35 U.S.C. 154(b) by 0 days.

(21) Appl. No.: 11/836,123

(22) Filed: Aug. 8, 2007

(65) Prior Publication Data

US 2008/0119891 A1 May 22, 2008

Related U.S. Application Data

(60) Provisional application No. 60/821,947, filed on Aug. 9, 2006, provisional application No. 60/821,949, filed on Aug. 9, 2006, provisional application No. 60/829,507, filed on Oct. 13, 2006, provisional application No. 60/866,047, filed on Nov. 15, 2006, provisional application No. 60/942,625, filed on Jun. 7, 2007.

(51) Int. Cl.
*A61B 17/03* (2006.01)

(52) U.S. Cl. .......................... 606/139; 606/151; 606/213

(58) Field of Classification Search .................. 606/213, 606/139, 142, 151, 200; 623/1.11, 1.23
See application file for complete search history.

(56) References Cited

U.S. PATENT DOCUMENTS

| 2,755,060 A | 7/1956 | Twyman |
| 3,874,388 A | 4/1975 | King et al. |

(Continued)

FOREIGN PATENT DOCUMENTS

EP 0539125 B1 4/1993

(Continued)

OTHER PUBLICATIONS

"Intravascular Occluding Device using a Modified Gianturco Stent as a Coil Cage." Wilson, Gordon, LaBerge, Saavedra and Kerlan. JVIR. 2000.

(Continued)

*Primary Examiner* — Corrine M McDermott
*Assistant Examiner* — Mark Mashack
(74) *Attorney, Agent, or Firm* — Holland & Hart LLP

(57) ABSTRACT

A medical system for treating an internal tissue opening can include a closure device and associated delivery device. The closure device can include a multi-cellular body portion operatively associated with a first anchor and a second anchor. The closure device can be configured to apply lateral force to tissue of the internal tissue opening for tissue approximation. The closure device can have a substantially flat aspect, and have a depth that is substantially greater than the thickness of a majority of the members forming the closure device. The closure device can also include an in-growth material. The delivery device can include an actuating assembly configured to partially deploy the closure device by a first movement, and deploy a second portion of the closure device by a second movement. The delivery device can also include a release assembly to selectively release or disconnect the closure device from the delivery device.

18 Claims, 48 Drawing Sheets

U.S. PATENT DOCUMENTS

| | | | |
|---|---|---|---|
| 4,007,743 A | 2/1977 | Blake |
| 4,708,140 A | 11/1987 | Baron |
| 4,762,129 A | 8/1988 | Bonzel |
| 4,840,185 A | 6/1989 | Hernandez |
| 4,917,089 A | 4/1990 | Sideris |
| 4,957,501 A | 9/1990 | Lahille et al. |
| 4,988,356 A | 1/1991 | Crittendon et al. |
| 5,002,531 A | 3/1991 | Bonzel |
| 5,040,548 A | 8/1991 | Yock |
| 5,041,093 A | 8/1991 | Chu |
| 5,108,420 A | 4/1992 | Marks |
| 5,171,259 A | 12/1992 | Inoue |
| 5,217,450 A | 6/1993 | Prior et al. |
| 5,232,445 A | 8/1993 | Bonzel |
| 5,234,458 A | 8/1993 | Metais |
| 5,300,085 A | 4/1994 | Yock |
| 5,334,217 A | 8/1994 | Das |
| 5,339,803 A | 8/1994 | Mayzels et al. |
| 5,425,744 A | 6/1995 | Fagan et al. |
| 5,433,723 A | 7/1995 | Lindenberg et al. |
| 5,433,727 A | 7/1995 | Sideris |
| 5,451,235 A | 9/1995 | Lock et al. |
| 5,484,449 A | 1/1996 | Amundson et al. |
| 5,496,277 A | 3/1996 | Termin et al. |
| 5,501,227 A | 3/1996 | Yock |
| 5,578,045 A | 11/1996 | Das |
| 5,634,931 A | 6/1997 | Kugel |
| 5,643,317 A | 7/1997 | Pavcnik et al. |
| 5,683,411 A | 11/1997 | Kavteladze et al. |
| 5,702,421 A | 12/1997 | Schneidt |
| 5,709,224 A | 1/1998 | Behl et al. |
| 5,725,552 A | 3/1998 | Kotula et al. |
| 5,741,297 A | 4/1998 | Simon |
| 5,766,184 A | 6/1998 | Matsuno et al. |
| 5,792,179 A | 8/1998 | Sideris |
| 5,846,261 A | 12/1998 | Kotula et al. |
| 5,853,422 A | 12/1998 | Huebsch et al. |
| 5,861,003 A | 1/1999 | Latson et al. |
| 5,879,366 A | 3/1999 | Shaw et al. |
| 5,904,703 A | 5/1999 | Gilson |
| 5,916,145 A | 6/1999 | Chu et al. |
| 5,944,738 A | 8/1999 | Amplatz et al. |
| 5,947,997 A | 9/1999 | Pavcnik et al. |
| 5,993,484 A | 11/1999 | Shmulewitz |
| 6,004,328 A | 12/1999 | Solar |
| 6,007,563 A | 12/1999 | Nash et al. |
| 6,031,148 A | 2/2000 | Hayes et al. |
| 6,077,281 A | 6/2000 | Das |
| 6,077,291 A | 6/2000 | Das |
| 6,080,182 A | 6/2000 | Shaw et al. |
| 6,165,167 A | 12/2000 | Delaloye |
| 6,168,616 B1 | 1/2001 | Brown, III |
| 6,171,329 B1 | 1/2001 | Shaw et al. |
| 6,174,322 B1 | 1/2001 | Schneidt |
| 6,196,995 B1 | 3/2001 | Fagan |
| 6,200,336 B1 | 3/2001 | Pavcnik et al. |
| 6,206,907 B1 | 3/2001 | Marino et al. |
| 6,210,338 B1 | 4/2001 | Afremov et al. |
| 6,214,029 B1 * | 4/2001 | Thill et al. ............... 606/213 |
| 6,241,678 B1 | 6/2001 | Afremov et al. |
| 6,267,777 B1 | 7/2001 | Bosma et al. |
| 6,273,901 B1 | 8/2001 | Whitcher et al. |
| 6,342,064 B1 | 1/2002 | Koike et al. |
| 6,355,052 B1 * | 3/2002 | Neuss et al. ............... 606/213 |
| 6,368,339 B1 | 4/2002 | Amplatz |
| 6,375,671 B1 | 4/2002 | Kobayashi et al. |
| 6,379,368 B1 | 4/2002 | Corcoran et al. |
| 6,440,152 B1 | 8/2002 | Gainor et al. |
| 6,482,221 B1 | 11/2002 | Hebert et al. |
| 6,551,344 B2 | 4/2003 | Thill |
| 6,589,207 B1 | 7/2003 | El-Nounou |
| 6,592,549 B2 | 7/2003 | Gerdts et al. |
| 6,596,013 B2 | 7/2003 | Yang et al. |
| 6,605,062 B1 | 8/2003 | Hurley et al. |
| 6,605,109 B2 | 8/2003 | Fiedler |
| 6,613,075 B1 | 9/2003 | Healy et al. |
| 6,645,225 B1 | 11/2003 | Atkinson et al. |
| 6,645,239 B1 | 11/2003 | Park et al. |
| 6,656,206 B2 | 12/2003 | Corcoran et al. |
| 6,679,909 B2 | 1/2004 | McIntosh et al. |
| 6,689,144 B2 | 2/2004 | Gerberding |
| 6,709,667 B1 | 3/2004 | Lowe et al. |
| 6,712,836 B1 | 3/2004 | Berg et al. |
| 6,723,071 B2 | 4/2004 | Gerdts et al. |
| 6,736,823 B2 | 5/2004 | Darios et al. |
| 6,743,210 B2 | 6/2004 | Hart et al. |
| 6,793,667 B2 | 9/2004 | Hebert et al. |
| 6,800,065 B2 | 10/2004 | Duane et al. |
| 6,837,894 B2 | 1/2005 | Pugsley, Jr. |
| 6,893,417 B2 | 5/2005 | Gribbons et al. |
| 6,913,614 B2 | 7/2005 | Marino et al. |
| 6,932,832 B2 | 8/2005 | Patel et al. |
| 6,979,311 B2 | 12/2005 | Miles et al. |
| 6,979,991 B2 | 12/2005 | Burns et al. |
| 6,994,689 B1 | 2/2006 | Zadno-Azizi et al. |
| 7,011,671 B2 | 3/2006 | Welch |
| 7,037,293 B2 | 5/2006 | Carrillo et al. |
| 7,087,088 B2 | 8/2006 | Berg et al. |
| 7,122,043 B2 | 10/2006 | Greenhalgh et al. |
| 7,137,990 B2 | 11/2006 | Hebert et al. |
| 7,144,410 B2 | 12/2006 | Marino et al. |
| 7,169,165 B2 | 1/2007 | Belef et al. |
| 7,179,252 B2 | 2/2007 | Agro et al. |
| 7,220,265 B2 | 5/2007 | Chanduszko et al. |
| 7,288,105 B2 | 10/2007 | Oman et al. |
| 7,318,833 B2 | 1/2008 | Chanduszko |
| 7,323,006 B2 | 1/2008 | Andreas et al. |
| 7,377,936 B2 | 5/2008 | Gainor et al. |
| 7,479,155 B2 | 1/2009 | Gainor et al. |
| 7,708,755 B2 * | 5/2010 | Davis et al. ............... 606/200 |
| 8,062,325 B2 * | 11/2011 | Mitelberg et al. ............... 606/200 |
| 2001/0007939 A1 | 7/2001 | Fleischman |
| 2001/0037129 A1 | 11/2001 | Thill |
| 2001/0039434 A1 | 11/2001 | Frazier et al. |
| 2002/0095141 A1 | 7/2002 | Belef et al. |
| 2002/0100485 A1 | 8/2002 | Stevens et al. |
| 2002/0111647 A1 | 8/2002 | Khairkhahan et al. |
| 2002/0169475 A1 * | 11/2002 | Gainor et al. ............... 606/213 |
| 2003/0028213 A1 * | 2/2003 | Thill et al. ............... 606/200 |
| 2003/0028235 A1 | 2/2003 | McIntosh et al. |
| 2003/0109886 A1 | 6/2003 | Keegan et al. |
| 2003/0139819 A1 | 7/2003 | Beer et al. |
| 2003/0167060 A1 | 9/2003 | Buzzard et al. |
| 2003/0181942 A1 | 9/2003 | Sutton et al. |
| 2003/0191479 A1 | 10/2003 | Thornton et al. |
| 2003/0191495 A1 | 10/2003 | Ryan et al. |
| 2003/0195561 A1 | 10/2003 | Carley et al. |
| 2003/0199987 A1 | 10/2003 | Berg et al. |
| 2003/0204203 A1 | 10/2003 | Khairkhahan et al. |
| 2003/0208232 A1 | 11/2003 | Blaeser et al. |
| 2003/0225421 A1 | 12/2003 | Peavey et al. |
| 2004/0010285 A1 | 1/2004 | Carley et al. |
| 2004/0044361 A1 * | 3/2004 | Frazier et al. ............... 606/200 |
| 2004/0073242 A1 | 4/2004 | Chandusko |
| 2004/0073252 A1 * | 4/2004 | Goldberg et al. ............... 606/200 |
| 2004/0098042 A1 | 5/2004 | Devellian et al. |
| 2004/0111095 A1 | 6/2004 | Gordon et al. |
| 2004/0133236 A1 | 7/2004 | Chandusko |
| 2004/0143294 A1 | 7/2004 | Corcoran et al. |
| 2004/0176799 A1 | 9/2004 | Chanduszko et al. |
| 2004/0220596 A1 | 11/2004 | Frazier et al. |
| 2004/0220610 A1 | 11/2004 | Kreidler et al. |
| 2004/0220612 A1 | 11/2004 | Swainston et al. |
| 2004/0254594 A1 | 12/2004 | Alfaro |
| 2004/0267306 A1 | 12/2004 | Blaeser et al. |
| 2005/0027305 A1 | 2/2005 | Shiu et al. |
| 2005/0033327 A1 | 2/2005 | Gainor et al. |
| 2005/0034735 A1 | 2/2005 | Deem et al. |
| 2005/0049681 A1 | 3/2005 | Greenhalgh et al. |
| 2005/0055050 A1 | 3/2005 | Alfaro |
| 2005/0065547 A1 | 3/2005 | Marino et al. |
| 2005/0113902 A1 | 5/2005 | Geiser et al. |
| 2005/0125032 A1 | 6/2005 | Whisenant et al. |
| 2005/0222603 A1 | 10/2005 | Andreas et al. |
| 2005/0228434 A1 | 10/2005 | Amplatz et al. |
| 2005/0228475 A1 | 10/2005 | Keeble et al. |
| 2005/0234509 A1 | 10/2005 | Widomski et al. |

| | | | |
|---|---|---|---|
| 2005/0251154 A1 | 11/2005 | Chanduszko et al. | |
| 2005/0251201 A1 | 11/2005 | Roue et al. | |
| 2005/0256532 A1 | 11/2005 | Nayak et al. | |
| 2005/0267524 A1 | 12/2005 | Chanduszko | |
| 2005/0267525 A1 | 12/2005 | Chanduszko | |
| 2005/0273119 A1 | 12/2005 | Widomski et al. | |
| 2005/0288706 A1 | 12/2005 | Widomski et al. | |
| 2005/0288786 A1 | 12/2005 | Chanduszko | |
| 2006/0009799 A1 | 1/2006 | Kleshinski et al. | |
| 2006/0106420 A1 | 5/2006 | Dolan et al. | |
| 2006/0116710 A1 | 6/2006 | Corcoran | |
| 2006/0122647 A1 | 6/2006 | Callaghan et al. | |
| 2006/0178694 A1 | 8/2006 | Greenhalgh et al. | |
| 2006/0271089 A1 | 11/2006 | Alejandro et al. | |
| 2007/0073389 A1 | 3/2007 | Bolduc et al. | |
| 2007/0100356 A1* | 5/2007 | Lucatero et al. | 606/139 |
| 2007/0106327 A1 | 5/2007 | Thill | |
| 2007/0112382 A1 | 5/2007 | Thill | |
| 2007/0123934 A1 | 5/2007 | Whisenant et al. | |
| 2007/0270905 A1* | 11/2007 | Osborne | 606/213 |
| 2008/0015636 A1 | 1/2008 | Olsen et al. | |
| 2008/0039743 A1 | 2/2008 | Fox et al. | |
| 2008/0039804 A1 | 2/2008 | Edmiston et al. | |
| 2008/0039922 A1 | 2/2008 | Miles et al. | |
| 2008/0039929 A1 | 2/2008 | Davis et al. | |
| 2008/0039952 A1 | 2/2008 | Linder et al. | |
| 2008/0039953 A1 | 2/2008 | Davis et al. | |
| 2008/0058866 A1 | 3/2008 | Young et al. | |

FOREIGN PATENT DOCUMENTS

| | | | |
|---|---|---|---|
| EP | 0541063 B1 | 9/1998 | |
| EP | 0545091 B1 | 7/1999 | |
| EP | 0614342 B1 | 7/1999 | |
| EP | 1013227 B1 | 6/2000 | |
| EP | 1046375 B1 | 10/2000 | |
| EP | 0474752 B2 | 12/2000 | |
| EP | 0861049 B1 | 4/2001 | |
| EP | 0698373 B1 | 11/2003 | |
| EP | 1179999 B1 | 1/2006 | |
| EP | 1211983 B1 | 3/2007 | |
| EP | 1864613 A1 | 12/2007 | |
| EP | 1222897 B1 | 3/2008 | |
| EP | 1923005 A2 | 5/2008 | |
| EP | 1923019 A1 | 5/2008 | |
| WO | WO0149185 A1 | 7/2001 | |
| WO | WO 03/068302 | 8/2003 | |
| WO | WO03082076 A2 | 10/2003 | |
| WO | WO2004052213 A1 | 6/2004 | |
| WO | WO2004091411 A2 | 10/2004 | |
| WO | WO2004103162 A2 | 12/2004 | |
| WO | WO2004103209 | 12/2004 | |
| WO | WO2005034738 A2 | 4/2005 | |
| WO | WO2006028813 A2 | 3/2006 | |
| WO | WO2006036837 A2 | 4/2006 | |
| WO | WO2006062711 A2 | 6/2006 | |
| WO | WO2006093968 A1 | 9/2006 | |
| WO | WO2006110147 | 10/2006 | |
| WO | WO2006130836 A2 | 12/2006 | |
| WO | WO2007021647 A2 | 2/2007 | |
| WO | WO2007028092 A2 | 3/2007 | |
| WO | WO2008025405 A1 | 3/2007 | |
| WO | WO2007038608 A1 | 4/2007 | |
| WO | WO2007038609 | 4/2007 | |
| WO | WO2007083288 A2 | 7/2007 | |
| WO | WO2007092860 | 8/2007 | |
| WO | WO2007120186 A2 | 10/2007 | |
| WO | WO2007136660 A2 | 11/2007 | |
| WO | WO2007140419 | 12/2007 | |
| WO | WO2007140420 A2 | 12/2007 | |
| WO | WO2008033309 A1 | 3/2008 | |
| WO | WO2008040555 A2 | 4/2008 | |
| WO | WO2008124603 A1 | 10/2008 | |
| WO | WO2008125689 A1 | 10/2008 | |

OTHER PUBLICATIONS

"Construction of hydraulic cuff colluders for blood vessels." Shoukas, Arin A., Department of Biomedical Engineering. Johns Hopkins University. 1976.

International Search Report dated Sep. 26, 2008 for International Application No. PCT/US07/75611 (2 pages).

International Search Report dated Sep. 9, 2008 for International Application No. PCT/US07/75608 (2 pages).

* cited by examiner

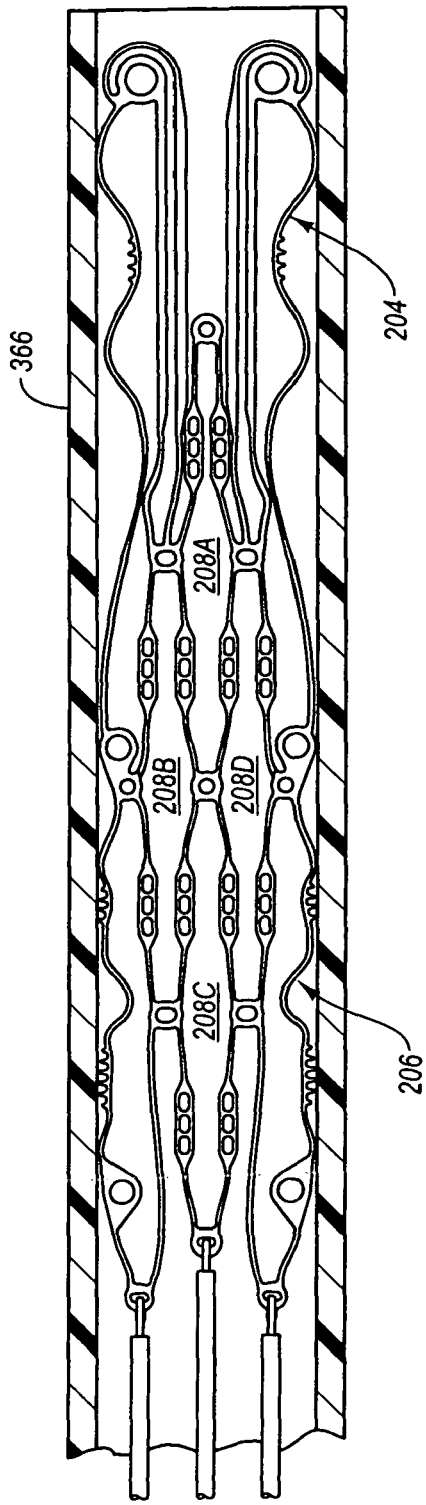
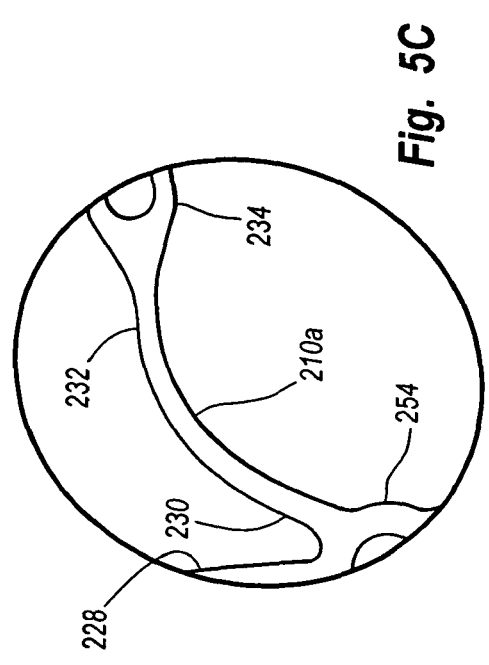
Fig. 5B
Fig. 5C

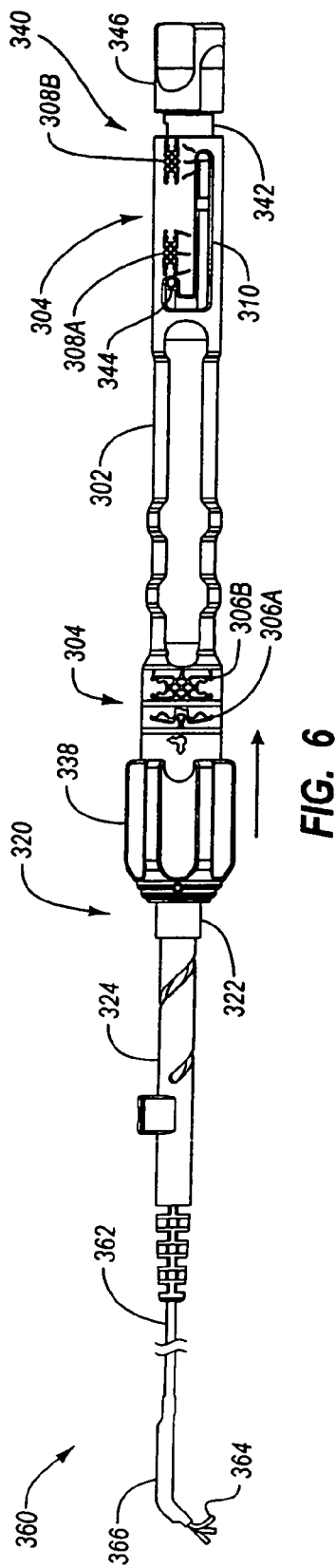
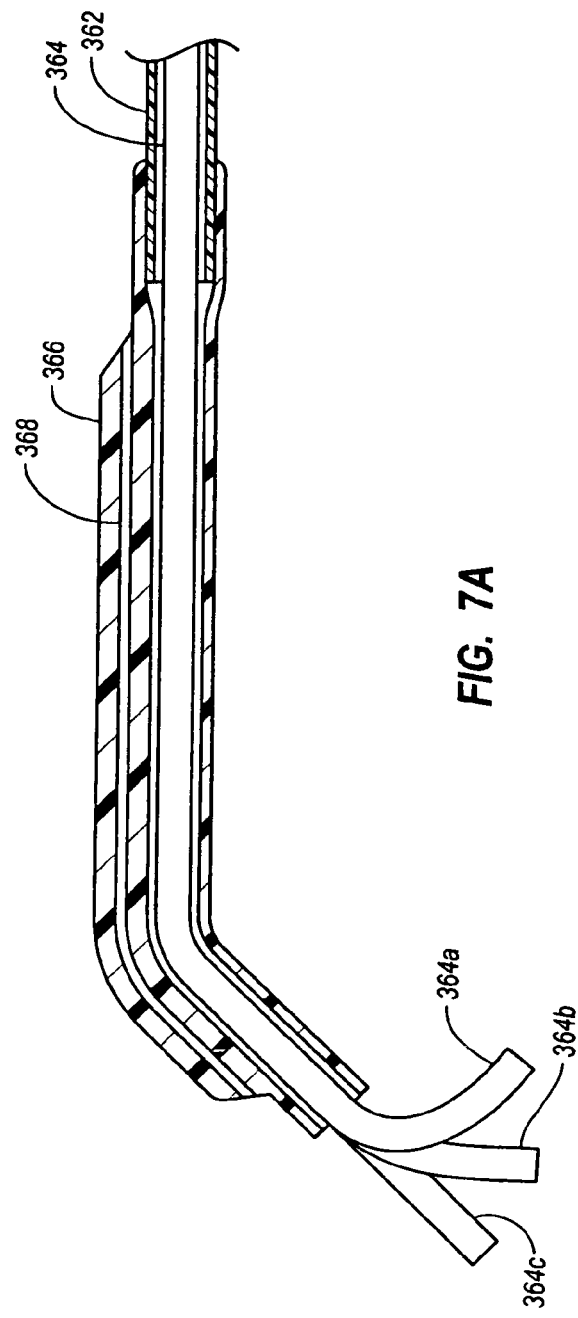
FIG. 6
FIG. 7A

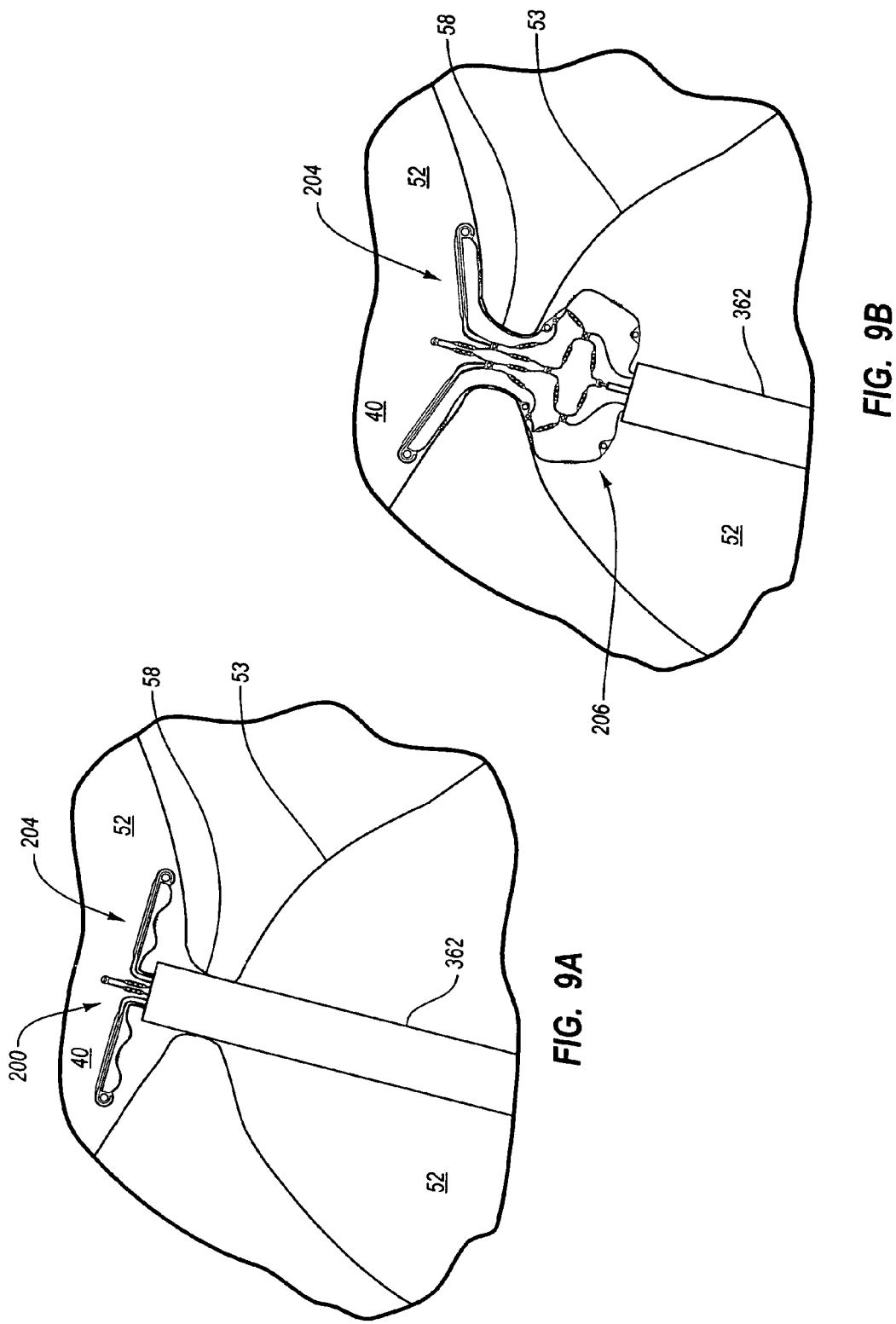

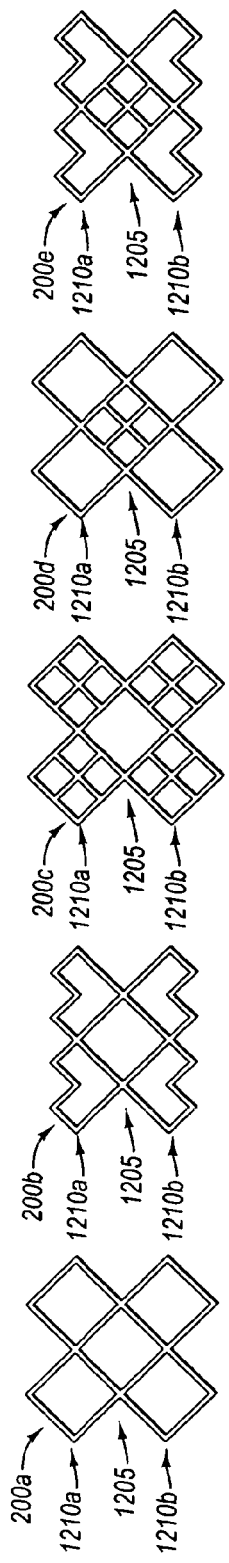
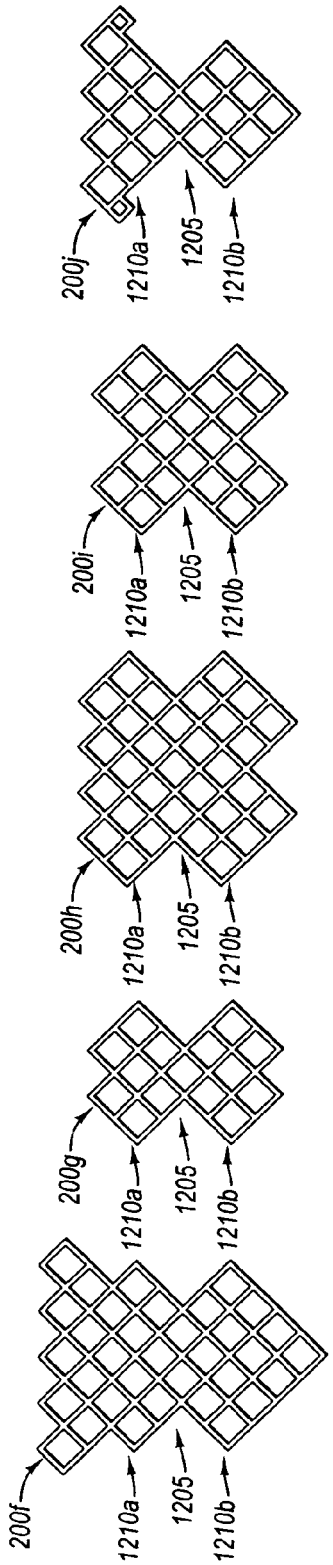
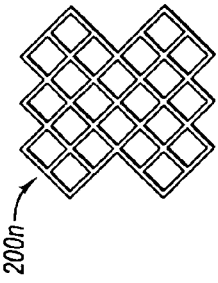
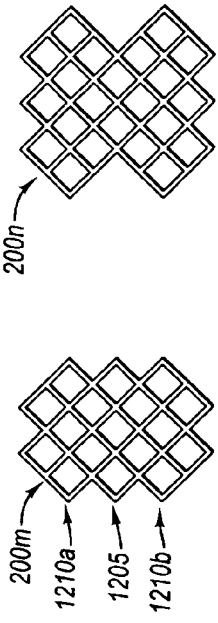
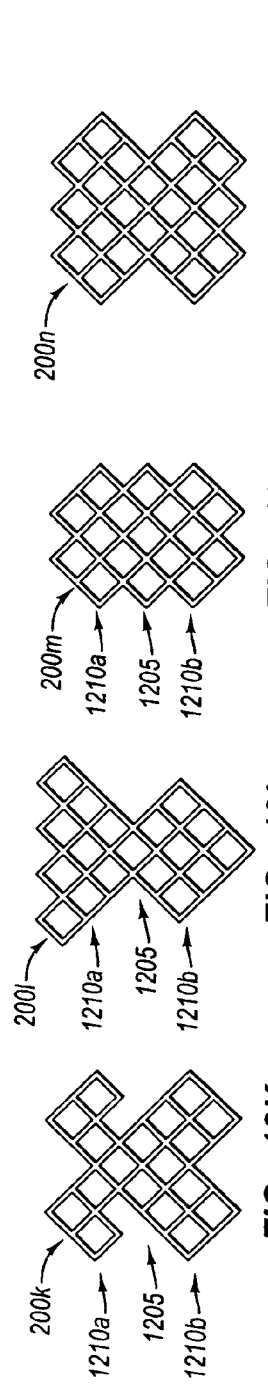

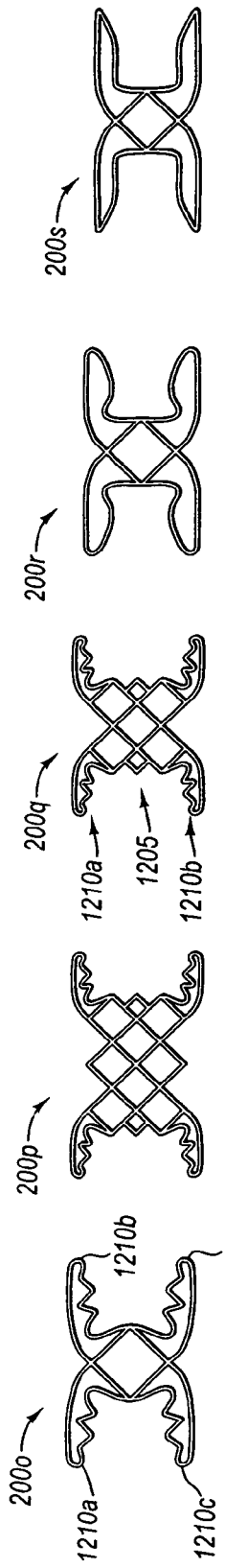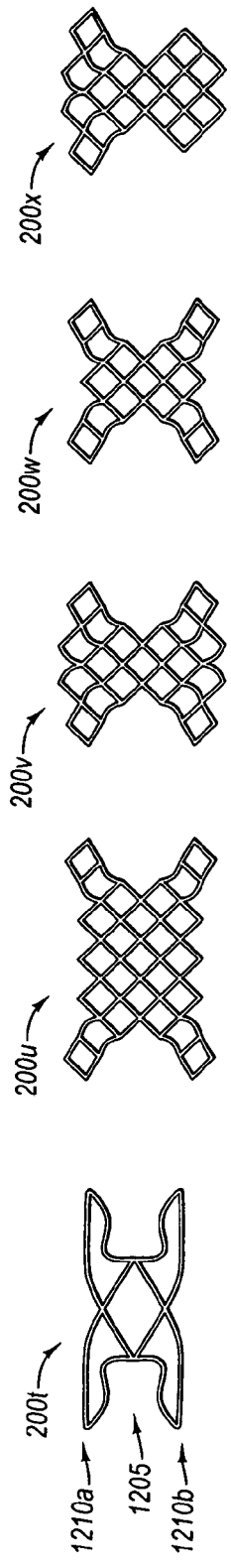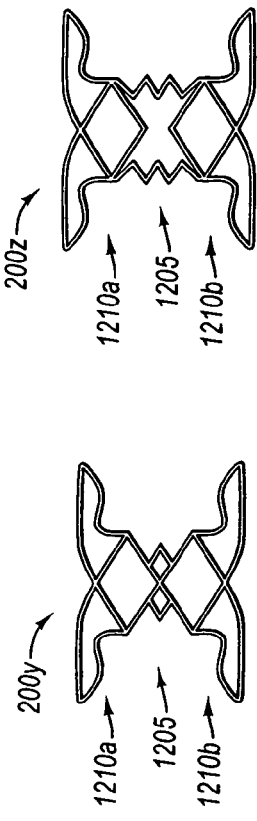

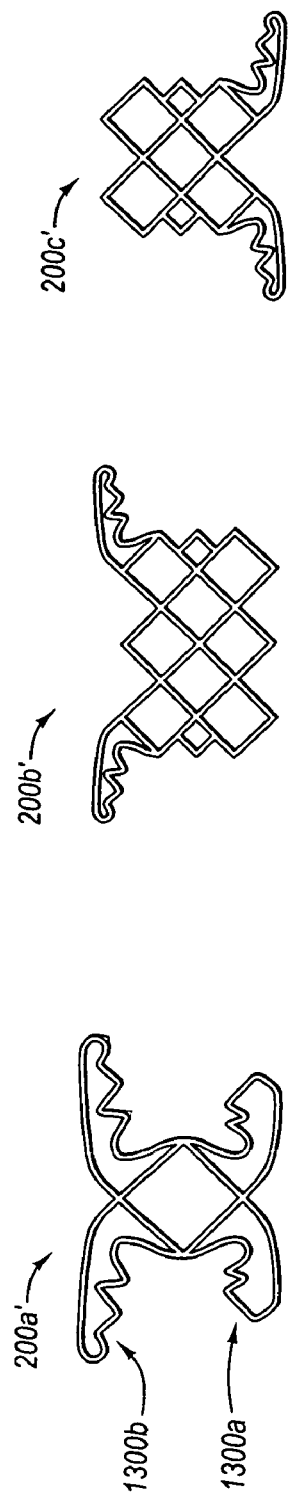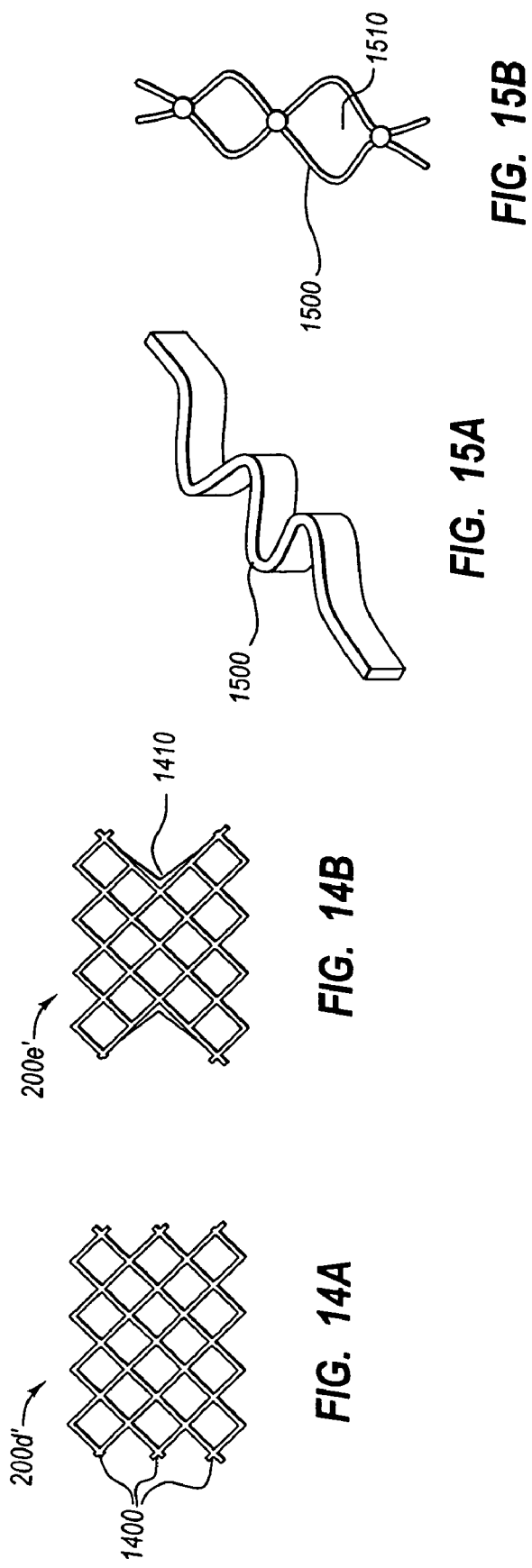

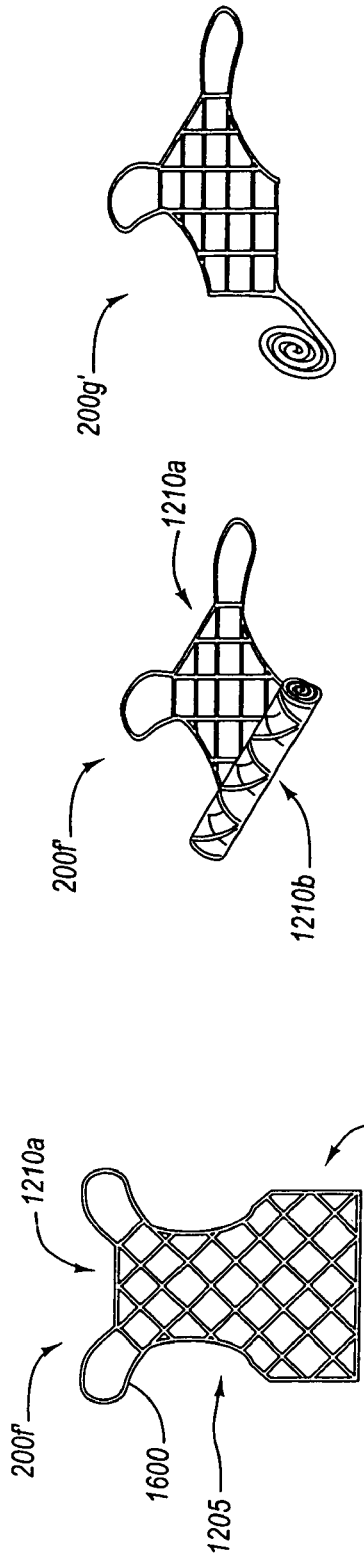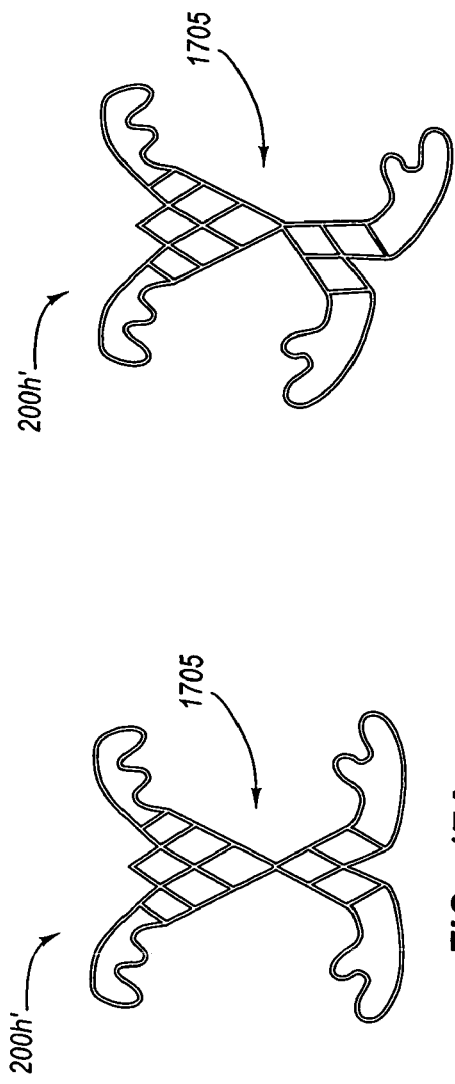

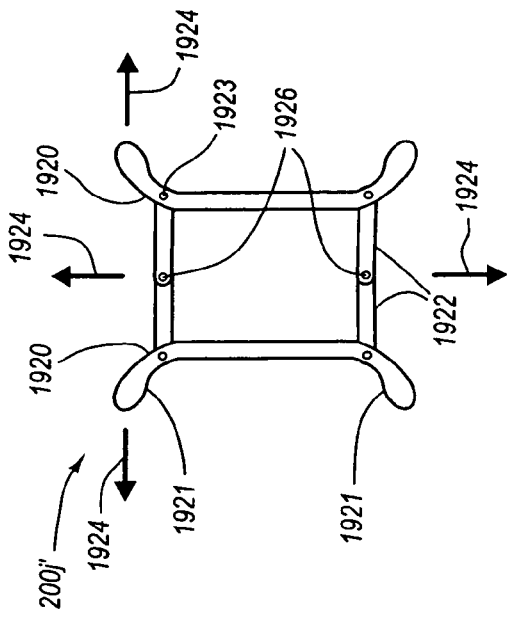
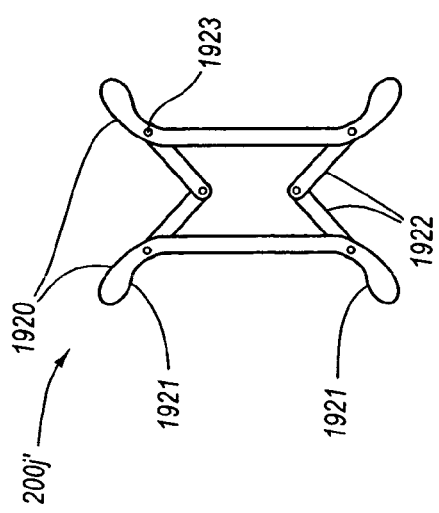
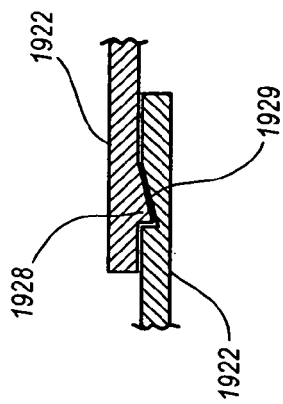
FIG. 19A
FIG. 19B
FIG. 19C
FIG. 19D

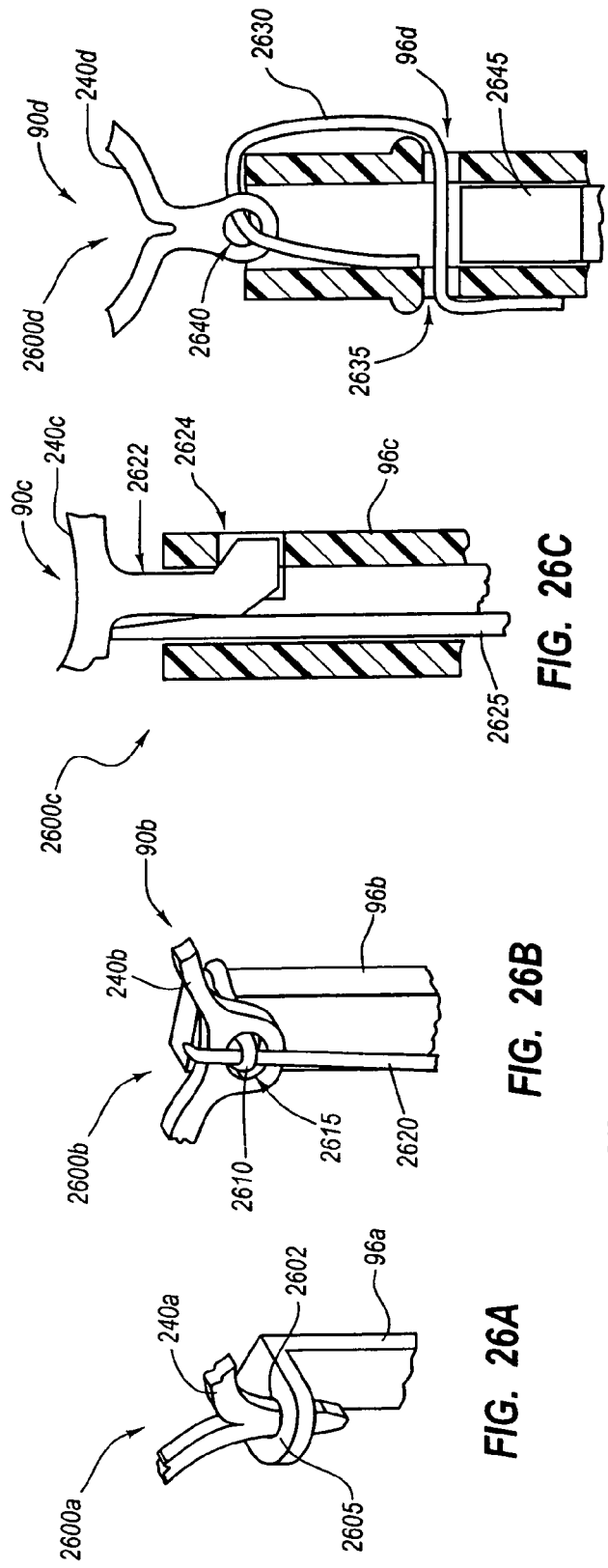

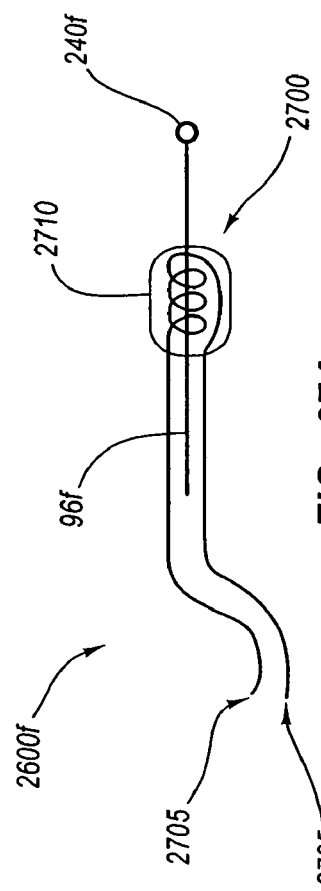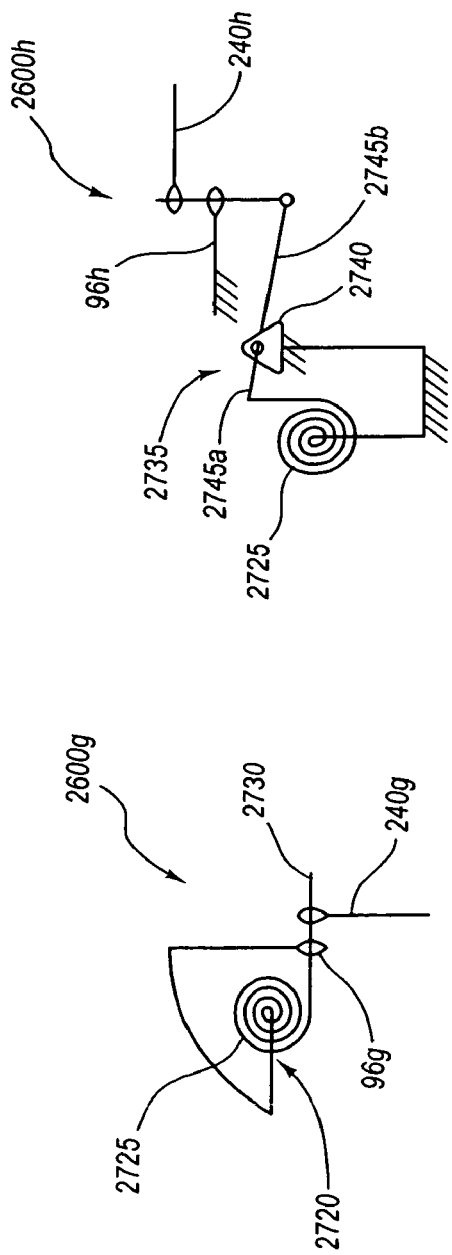
FIG. 27A
FIG. 27B
FIG. 27C

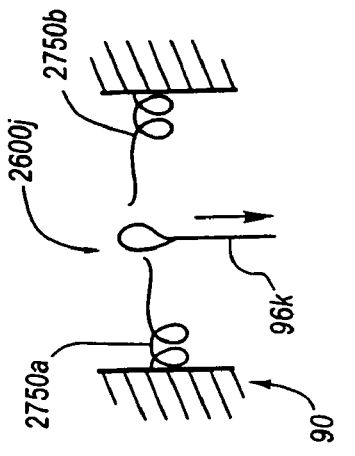
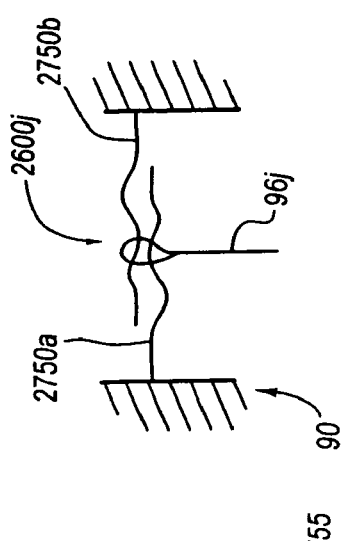
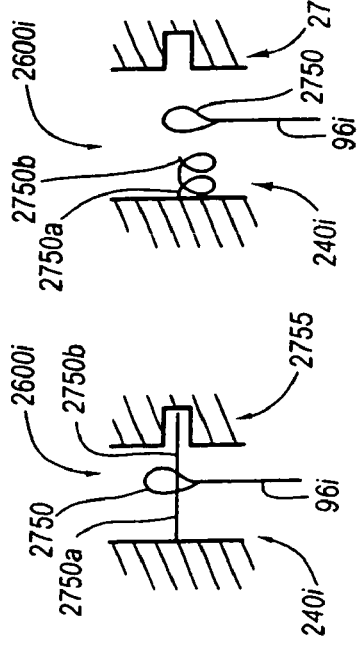
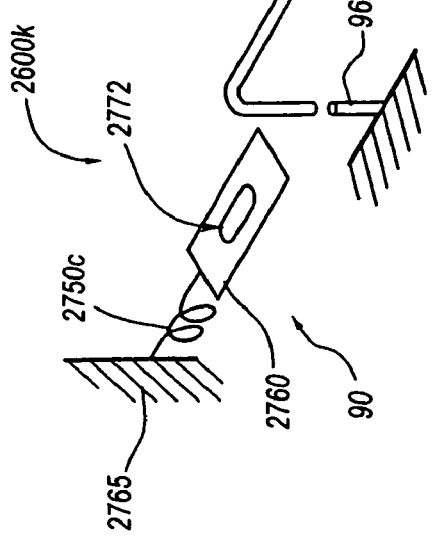
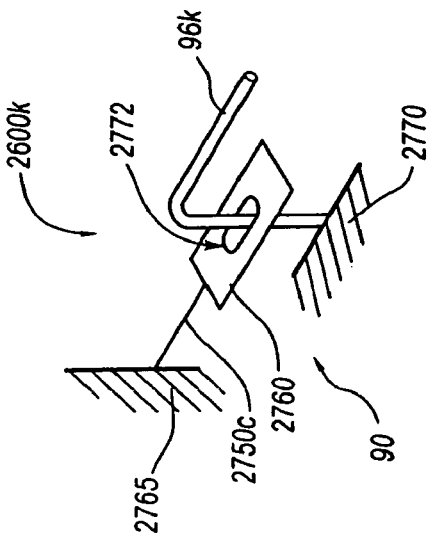

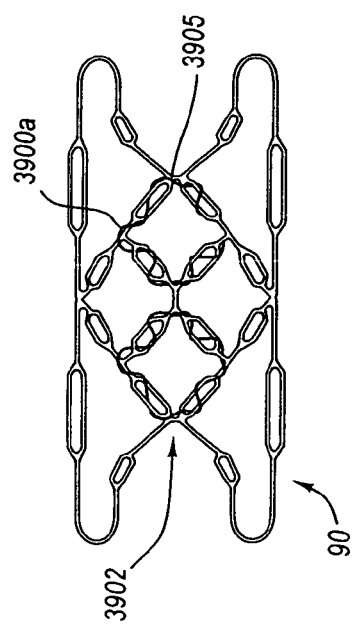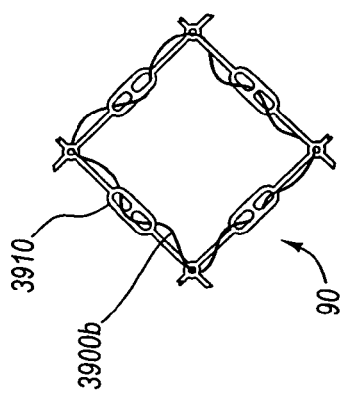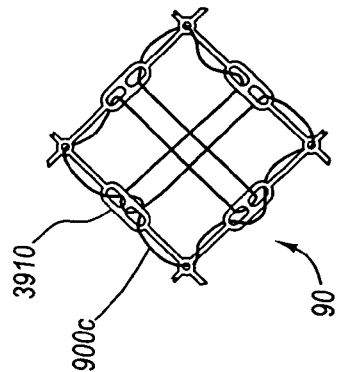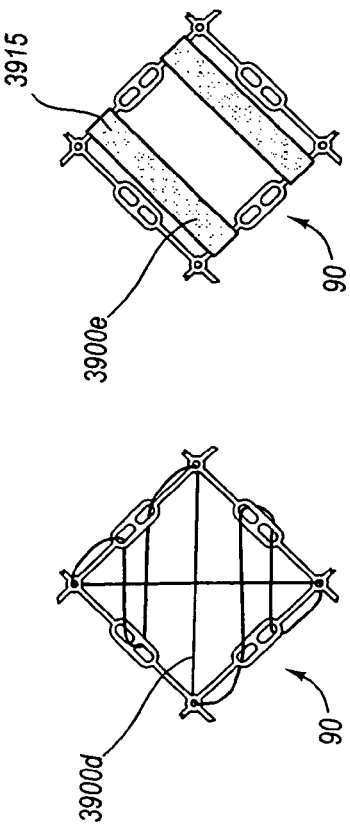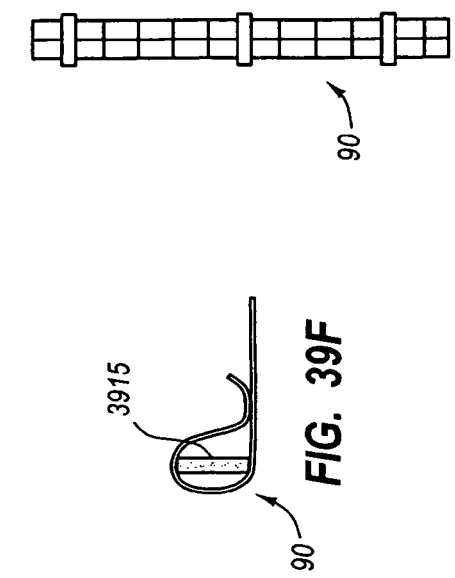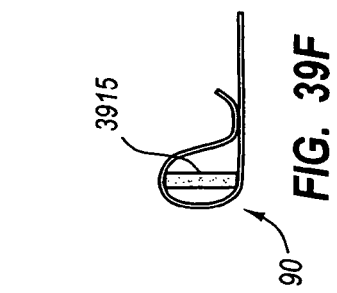

METHODS, SYSTEMS AND DEVICES FOR REDUCING THE SIZE OF AN INTERNAL TISSUE OPENING

CROSS-REFERENCE TO RELATED APPLICATIONS

This application claims the benefit of U.S. Provisional Application No. 60/821,947, filed Aug. 9, 2006, U.S. Provisional Application No. 60/821,949, filed Aug. 9, 2006, U.S. Provisional Application No. 60/829,507, filed Oct. 13, 2006, U.S. Provisional Application No. 60/866,047, filed Nov. 15, 2006, and U.S. Provisional Application No. 60/942,625, filed Jun. 7, 2007, the contents of each of which are hereby incorporated by reference in their entirety. This application relates to U.S. patent application Ser. No. 11/836,000, filed Aug. 8, 2007, titled DEVICES FOR REDUCING THE SIZE OF AN INTERNAL TISSUE OPENING, U.S. patent application Ser. No. 11/836,016, filed Aug. 8, 2007, titled DEVICES FOR REDUCING THE SIZE OF AN INTERNAL TISSUE OPENING, U.S. patent application Ser. No. 11/836,037, filed Aug. 8, 2007, titled DEVICES FOR REDUCING THE SIZE OF AN INTERNAL TISSUE OPENING, U.S. patent application Ser. No. 11/836,051, filed Aug. 8, 2007, titled SYSTEMS AND DEVICES FOR REDUCING THE SIZE OF AN INTERNAL TISSUE OPENING, U.S. patent application Ser. No. 11/836,013, filed Aug. 8, 2007, titled SYSTEMS AND DEVICES FOR REDUCING THE SIZE OF AN INTERNAL TISSUE OPENING, and U.S. patent application Ser. No. 11/836,026, filed Aug. 8, 2007, titled METHODS FOR DETERMINING CHARACTERISTICS OF AN INTERNAL TISSUE OPENING, the contents of each of which are hereby incorporated by reference in their entirety.

BACKGROUND OF THE INVENTION

1. The Field of the Invention

The present invention relates generally to medical devices and methods of use for treating an internal tissue structure. More particularly, the present invention relates to medical devices, systems, and methods for reducing the size of an internal tissue opening.

2. The Relevant Technology

Physical malformations or defects that are present at birth can be detrimental and even lethal when left uncorrected. A PFO is an example of a cardiac birth defect that can be problematic and even result in death when combined with other factors such as blood clots or other congenital heart defects. A PFO occurs when an opening between the upper two chambers of the heart fail to close after birth.

Some of the problems associated with a PFO can occur when a blood clot travels from the right to the left atria of the heart through the PFO, and lodges in an artery that feeds blood to the brain. A blood clot in the left atrium can be passed through the aorta and travel to the brain or other organs, and cause embolization, stroke, or a heart attack. A PFO can be treated by being closed by a surgical procedure. Additionally, other similar defects (e.g., septal or otherwise) where some tissue needs to be closed in order to function properly can include the general categories of atrial-septal defects ("ASDs"), ventricular-septal defects ("VSDs") and patent ductus arteriosus ("PDA"), and the like.

FIGS. 1A-1C depict various views of a heart having a PFO. The heart 10 is shown in a cross-sectional view in FIG. 1A. In a normal heart 10, the right atrium 30 receives systemic venous blood from the superior vena cava 15 and the inferior vena cava 25, and then delivers the blood via the tricuspid valve 35 to the right ventricle 60. However, in the depicted heart 10, a septal defect, which is shown as a PFO 50, is present between right atrium 30 and left atrium 40.

The PFO 50 is depicted as an open flap on the septum between the heart's right atrium 30 and left atrium 40. In a normal heart 10, the left atrium 40 receives oxygenated blood from the lungs via pulmonary artery 75, and then delivers the blood to the left ventricle 80 via the mitral valve 45. In a heart 10 having a PFO 50, some systemic venous blood can also pass from the right atrium 30 through the PFO 50, mixes with the oxygenated blood in the left atrium 40, and then is routed to the body from the left ventricle 80 via the aorta 85.

During fetal development of the heart 10, the interventricular septum 70 divides the right ventricle 60 and left ventricle 80. In contrast, the atrium is only partially partitioned into right and left chambers during normal fetal development, which results in a foramen ovale fluidly connecting the right and left atrial chambers. As shown in FIG. 1B, when the septum primum 52 incompletely fuses with the septum secundum 54 of the atrial wall, the result can be a tunnel 58 depicted as a PFO 50.

FIG. 1C provides a view of the crescent-shaped, overhanging configuration of the septum secundum 54 from within the right atrium 30 in a heart 10 having a PFO 50. The septum secundum 54 is defined by its inferior aspect 55, corresponding with the solid line in FIG. 1C, and its superior aspect 53 represented by the phantom line, which is its attachment location to the septum primum 52. The septum secundum 54 and septum primum 52 blend together at the ends of the septum secundum 54. The anterior end 56a and posterior end 56p are referred to herein as "merger points" for the septum secundum 54 and septum primum 52. The length of the overhang of the septum secundum 54, which is the distance between superior aspect 53 and inferior aspect 55, increases towards the center portion of the septum secundum as shown.

The tunnel 58 between the right atrium 30 and left atrium 40 is defined by portions of the septum primum 52 and septum secundum 54 between the merger points 56a and 56p, which have failed to fuse. The tunnel 58 is often at the apex of the septum secundum 54 as shown. When viewed within right atrium 30, the portion of the septum secundum 54 to the left of tunnel 58, which is referred to herein as the posterior portion 57p of the septum secundum, is longer than the portion of the septum secundum 54 to the right of tunnel 58, which is referred to herein as the anterior portion 57a of the septum secundum 54. In addition to being typically longer, the posterior portion 57p also typically has a more gradual taper than the anterior portion 57a as shown. The anterior pocket 59a is the area defined by the overhang of the anterior portion 57a of the septum secundum 54 and the septum primum 52, and it extends from the anterior merger point 56a toward the tunnel 58. Similarly, the posterior pocket 59p is the area defined by the overhang of the posterior portion 57p of septum secundum 54 and the septum primum 52, and it extends from the posterior merger point 56p toward the tunnel 58.

Conventional treatments for PFO and other related conditions have generally involved invasive surgery, which also presents risks to a patient. Although there are some less invasive treatments for PFO, such treatments have been less efficient at closing the PFO opening than techniques involving invasive surgery.

BRIEF SUMMARY OF THE INVENTION

The invention relates to a medical system, devices and methods of use for reducing the size of an internal tissue opening, such as a Patent Foramen Ovale ("PFO"). In one embodiment of the invention, the medical system can include a closure device and an associated delivery device. The medical system can be configured to enable a practitioner to selectively position and deploy the closure device in an internal tissue opening to approximate the tissue of the opening.

According to one embodiment of the invention, the closure device can include a multi-cellular body portion operatively associated with a first anchor and a second anchor. The multi-cellular body portion can be configured to enable the closure device to collapse into a relatively narrow non-deployed orientation and expand into a non-deployed orientation without plastic deformation or failure of the closure device. The first and second anchors can be configured to engage at least a portion of a wall of the internal tissue opening and/or tissue, such as tunnel tissue, of the opening.

In one embodiment of the invention, the closure device can include an in-growth material to facilitate tissue growth. The closure device can also include one or more indicators to facilitate the estimation of the position and/or orientation of the closure device with respect to the internal tissue opening.

In accordance with the present invention, the delivery device can include a delivery assembly, an actuating assembly, and a release assembly operatively associated with a handle body. In one embodiment of the invention, the delivery assembly facilitates selective delivery of the closure device from the delivery device, and is operatively associated with the actuating assembly and the release assembly. The actuating assembly interacts with the handle body to selectively deploy the closure device from the delivery assembly. In one embodiment of the invention, the actuating assembly can be configured to deploy at least a portion of the closure device by a first movement and deploy a second portion of the closure device by a second movement. The release assembly can be linked to the handle body to facilitate detachment of the closure device from the delivery device.

In one embodiment, the closure device is linked to the delivery device by one or more tethers and one or more wires, the tethers being coupled to the handle body and the wires being coupled to a biasing member of the release assembly. The tethers can be configured to receive a portion of the closure device therein to facilitate securement of the closure device to the delivery device. The wires can be detachably coupled to the closure device to enable selective detachment of the closure device from the delivery device by movement of the biasing member.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof, which are illustrated in the appended drawings. It is appreciated that these drawings depict only typical embodiments of the invention and are, therefore, not to be considered limiting of its scope. The invention will be described and explained with additional specificity and detail through the use of the accompanying drawings in which:

FIGS. 5A-5C illustrate a closure device in accordance with the present invention:

FIG. 6 illustrates a delivery device according to one example;

FIGS. 7A-7D illustrate cross-sectional views of a delivery device according to one example;

FIG. 9A illustrates an embodiment of a closure device being partially deployed in an internal tissue opening;

FIG. 9B illustrates a delivery device in an orientation corresponding to the partially deployed closure device of FIG. 8A according to one example;

FIGS. 12A-21B are schematic diagrams of closure devices in accordance with the present invention;

FIGS. 26A-27M illustrate release mechanisms according to several examples;

FIGS. 39A-39M illustrate configurations to promote tissue growth according to several examples.

DETAILED DESCRIPTION OF THE PREFERRED EMBODIMENTS

The present invention extends to medical systems, methods, and apparatus for reducing the size of an internal tissue opening. By way of explanation, the devices disclosed herein can be used to treat a variety of internal tissue openings, such as a left atrial appendage, paravalvular leaks, PDAs, and VSDs, for example. For purposes of simplicity, frequent reference is made herein to reducing the size of or closing an opening in heart tissue known as Patent Foramen Ovale ("PFO"). Accordingly, it will be understood that references to PFO openings are not limiting of the invention.

In at least one example, a closure device is disclosed herein that is configured to acutely provide forces to close the opening associated with a PFO and allow the natural healing processes to effect a chronic closure. The closure device, when deployed, can have a flat aspect having a width and length, but a small thickness. The length of the device may correspond to a length of the internal tissue opening or the tunnel length of the internal tissue opening. The width of the device may correspond to a dimension that is generally transverse to the length.

Figure 1B:
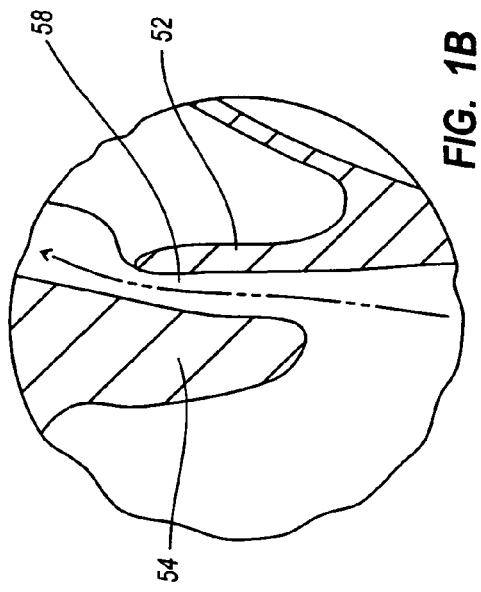
FIGS. 1A-1C illustrate exemplary views of a heart having a Patent Foramen Ovale.
Figure 1C:
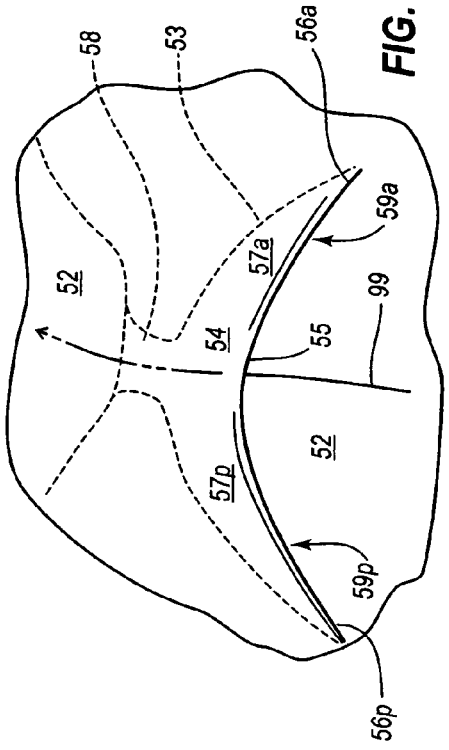
Figure 1A:
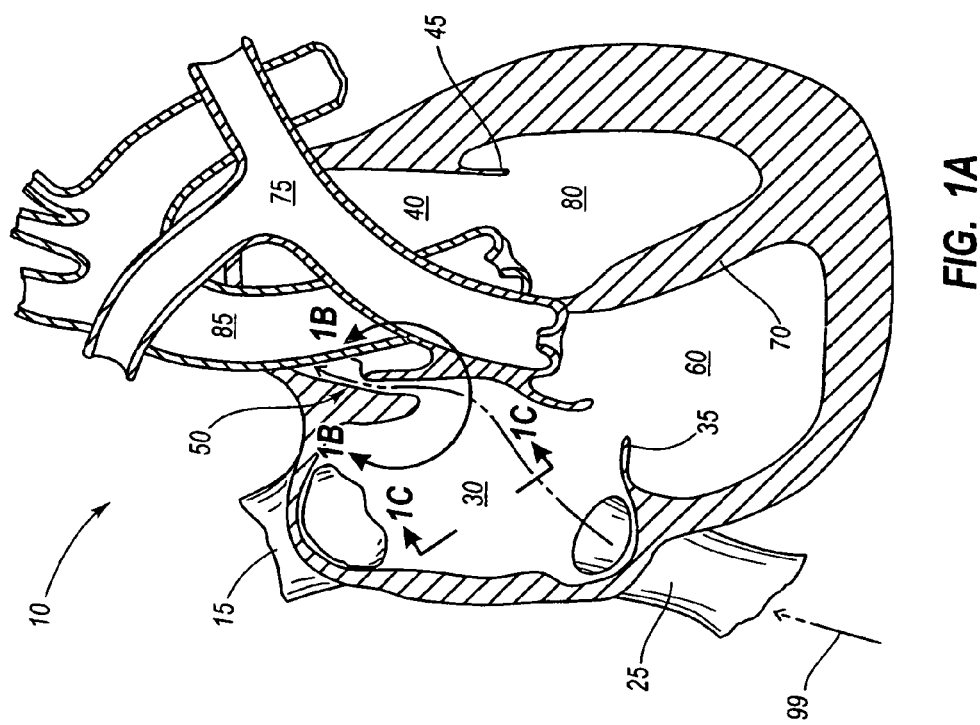

The closure device may have an expandable, multi-cellular structure that is configured to exert a lateral force on the walls of the internal tissue opening. In at least one example, the lateral force expands the width dimension of the tunnel a sufficient amount to reduce the height of the tunnel to thereby reduce the size of the tunnel and thereby close the internal tissue opening. The structural properties of the device can resist bending or curling out of plane to prevent or substantially limit the tendency of the device to prop the PFO open rather than closing it. This property may be achieved by utilizing struts with a preferential bending direction that is oriented parallel to the plane of the device and a non-preferential bending direction that is oriented perpendicular to the plane of the device, as is shown in FIG. 1E and will be described in more detail hereinafter.

In the following description, numerous specific details are set forth to assist in providing an understanding of the present invention. In other instances, aspects of delivery and/or closure devices, or medical devices in general have not been described in particular detail in order to avoid unnecessarily obscuring the present invention. In addition, it is understood that the drawings are diagrammatic and schematic representations of certain embodiments of the invention, and are not limiting of the present invention, nor are they necessarily drawn to scale.

Figure 2:
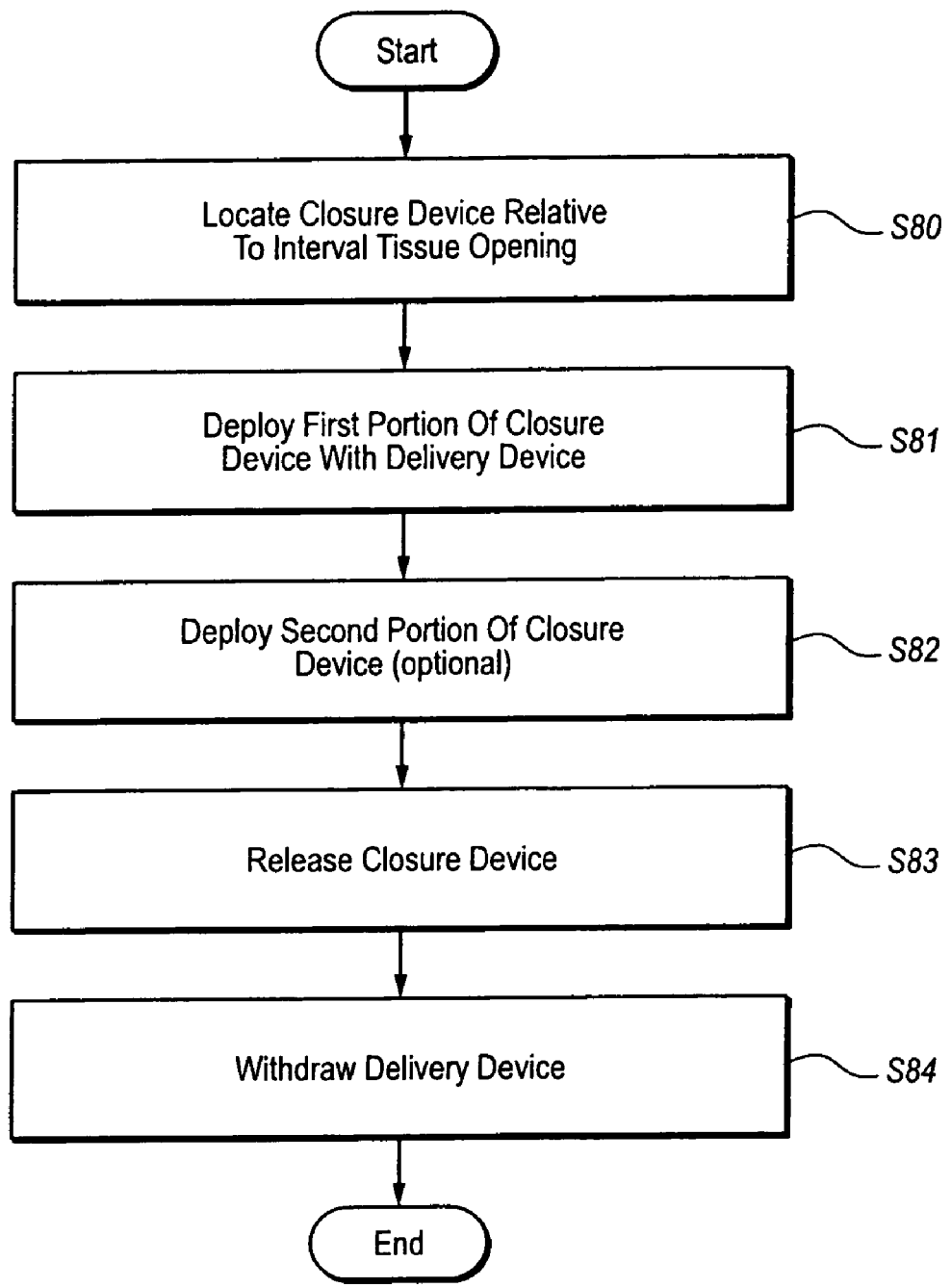
FIG. 2 is a flowchart illustrating a method of reducing the size of an internal tissue opening according to one example.

FIG. 2 is a flowchart illustrating a method of reducing the size of an internal tissue opening according to one example. Each of the steps will be introduced generally, followed by a discussion of each step with respect to the schematic diagrams illustrated in FIGS. 3A-3D. The method begins at step S80 by initially locating a closure device with respect to the internal tissue opening. In at least one example, initially locating a closure device with respect to an internal tissue opening includes using a delivery device that is configured to retain the closure device in a distal end while allowing a user to control the deployment of a closure device at a proximal end.

The closure devices described herein include collapsible multi-cellular closure devices that are configured to be stored in a collapsed state within the delivery device while the closure device is located relative to the internal tissue opening. Further, the configuration of the closure devices described herein can enable the closure device to be movable between a non-deployed or compressed state and a deployed or decompressed state without causing failure or plastic deformation of the closure device.

The method continues at step S81 by deploying a first portion of the closure device using the delivery device. Deployment of the first portion of the closure device may include expanding at least one of the cellular portions from the collapsed position within the delivery device to an expanded state. Further, at step S82 the method may further optionally include the deployment of a second portion of the closure device and may include expanding additional cellular portions from the previously described collapsed position with the delivery device to an expanded state. As many cellular portions may be deployed in as many steps as desired.

As will be discussed with reference to FIG. 3A, regardless of the number of stages in which the closure device is deployed, once deployed, the closure device exerts a force on the internal tissue opening to close the opening. Once the closure device has been deployed to close the internal tissue opening, the closure device is released from the delivery device at step S83 and the delivery device is withdrawn at step S84. A schematic diagram will now be discussed to illustrate various steps of the process illustrated in FIG. 2.

Figure 3:
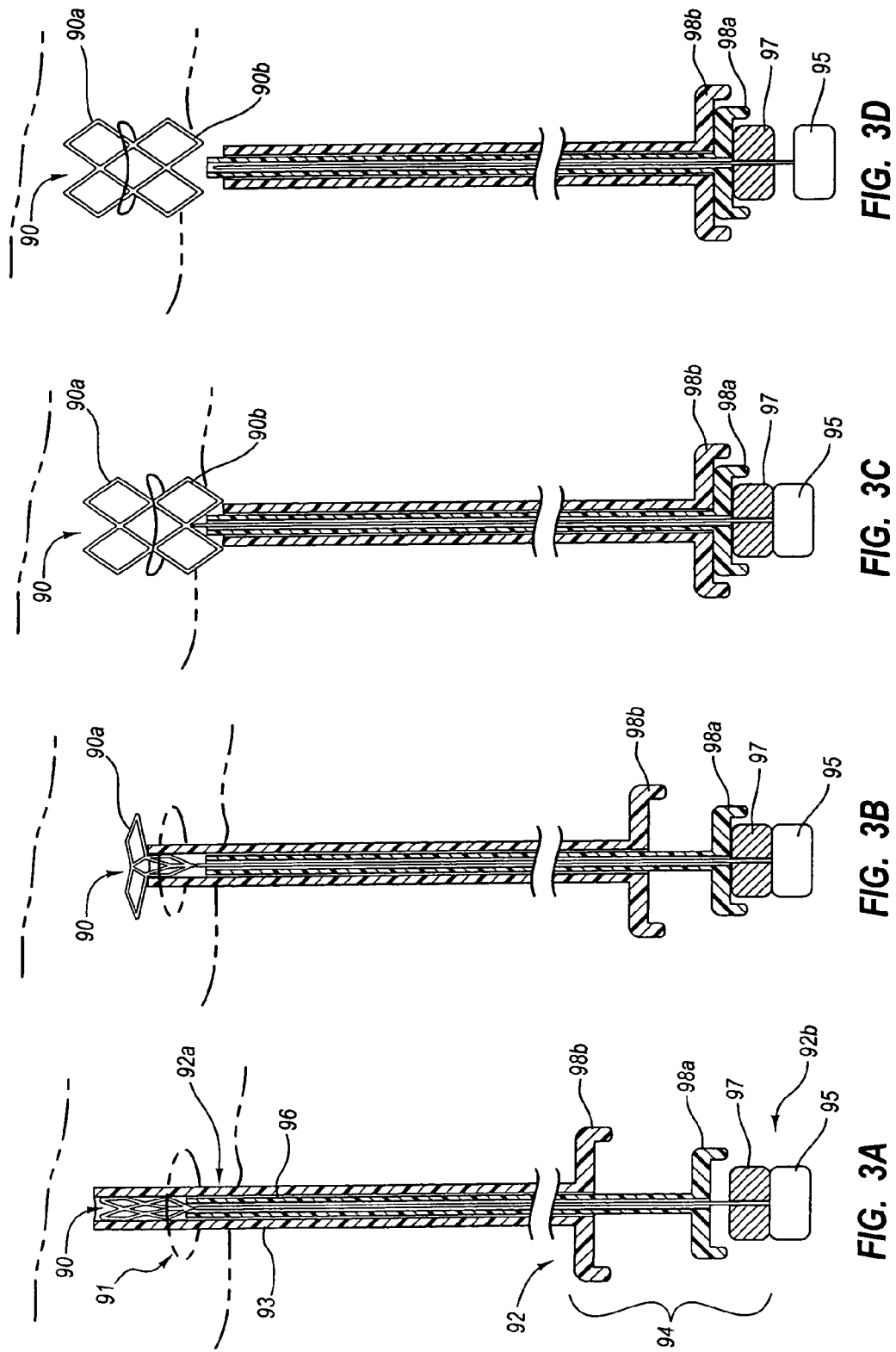
FIG. 3A is a schematic diagram illustrating a step for locating a closure device with respect to an internal tissue opening using a delivery device according to one example.
FIG. 3B is a schematic diagram illustrating a step for deploying a first portion of a closure device according to one example.
FIG. 3C is a schematic diagram illustrating a step for deploying a second portion of a closure device and an internal tissue opening having a reduced size according to one example.
FIG. 3D is a schematic diagram illustrating release of a closure element from a delivery device according to one example.

FIG. 3A is a schematic diagram illustrating the step of locating a closure device 90 with respect to an internal tissue opening 91 using a delivery device 92 (step S80). The internal tissue opening 91 may be described as an opening having a tunnel that extends between a proximal surface and through a distal surface of tissue. For ease of reference, the distance between the proximal surface and the distal surface may be described as a length of the internal tissue opening 91.

As introduced, the dimension of the closure device 90 that corresponds to the length of the internal tissue opening 91 is referred to as the length of the closure device 90. As the closure device 90 is deployed, the closure device 90 expands to apply a lateral force on the wall(s) of the internal tissue opening 91 to thereby reduce the size thereof. The direction in which the closure device 90 expands may be referred to as the width of the closure device 90. In at least one example, the closure device 90 may be generally flat across its width, both when in the collapsed state as well as in the expanded state illustrated and described below.

The delivery device 92 according to the present example includes a distal end 92a and a proximal end 92b. The delivery device 92 further includes delivery assembly 93 near distal end 92a, and an actuation assembly 94 and a release assembly 95 near the proximal end 92b. The closure device 90 is a multi-cellular device that includes a plurality of collapsible cells that may expand to an expanded state described above. The closure device 90 is illustrated in a collapsed state within the delivery assembly 93. Accordingly, locating the closure device 90 relative to the internal tissue opening 91 may include locating a distal end 93a of the delivery assembly 93 near the internal tissue opening 91.

While located within the delivery assembly 93, the closure device 90 is coupled to a push member 96, which in turn is coupled to a control anchor 97. The delivery assembly 93 is coupled to control assemblies 98a, 98b, which may be part of the closure device 90. In one example, the control assemblies 98a, 98b and delivery assembly 93 may be held in a fixed relationship relative to each other as the control anchor 97 is advanced. As the control anchor 97 advances relative to the control assemblies 98a, 98b and the delivery assembly 93, control anchor 97 drives the push member 96, which in turn pushes the closure device 90 distally relative to the delivery assembly 93.

As illustrated in FIG. 3B, the control anchor 97 may be thus advanced until the control anchor 97 comes into contact with first control assembly 98a while driving a first portion 90a of the closure device 90 from the distal end 93a of the delivery assembly 93. As the first portion 90a of the closure device 30 is thus driven from the delivery assembly 93, the first portion 90a is deployed by expanding from the compressed state illustrated in FIG. 3A to the expanded state illustrated in FIG. 3B. In the example of FIG. 3B, the delivery assembly 93 may extend at least partially through the internal tissue opening 91 to deliver the first portion 90a of the closure device 90 distally of the internal tissue opening 91 (step S81). The first portion 90a may then be drawn into contact with the distal opening of the internal tissue opening 91.

Thereafter, while the control anchor 97 is in contact with the first control assembly 98a, the control anchor 97 and the first control assembly 98a may be moved together relative to the second control assembly 98b and the delivery assembly 93 to drive the closure device 90 further from the delivery assembly 93. In particular, as illustrated in FIG. 3C, the control anchor 97 and the first control assembly 98a may be driven until the first control assembly 98a comes into contact with the second control assembly 98b. In at least one example, this distance may be sufficient for the push member 96 to push the closure device 90 clear of the distal end 93a of the delivery assembly 93 to thereby fully deploy closure device 90 (step S82).

As the closure device 90 is fully deployed, at least a second portion 90b of the closure device 90 expands outwardly within the internal tissue opening 91. As the second portion 90b expands outwardly, the width of the second portion 90b expands to apply a lateral force on the internal tissue opening 91, the force being generally along the width of the internal tissue opening 91. As the second portion 90b becomes wider, the portions of the internal tissue opening 91 illustrated as the sides are drawn apart while the portion of the internal tissue opening illustrated as the top and bottom are approximated. The overall result is that the internal tissue opening 91 is constricted to close down the internal tissue opening 91.

A third portion 90c of the closure device 90 may be deployed proximally of the internal tissue opening 91 as the closure device 90 is fully deployed. As previously introduced, the first portion of the closure device 90 may be deployed distally of the internal tissue opening 91. Once fully deployed, the third portion 90c may be deployed proximally of the internal tissue opening 91. Such a configuration may reduce the likelihood that the closure device 90 will migrate through the internal tissue opening 91.

Once the internal tissue opening 91 has been closed, the closure device 90 is released from the delivery device 92 as in FIG. 3D (step S83). As illustrated in FIGS. 3A-3D, the release assembly 95 of the delivery device 92 moves in concert with the push member 96 during the deployment of the closure device 90. A release coupler 99 links the release assembly 95 to the closure device 90. In one example, to release the closure device 90, the release assembly 95 is moved proximally relative to the actuation assembly 94. As the release assembly 95 moves proximally, the release coupler 99 releases the closure device 90 from the delivery device 92 and from the delivery assembly 93 in particular. Several release configurations are discussed in more detail below.

Accordingly, the system is configured to deploy a closure device to close an internal tissue opening. One medical system will now be described in more detail that includes a detailed discussion of one exemplary delivery device and exemplary closure device. Additional closure devices will then be discussed, followed by a discussion of in-growth material configurations that may be used with closure devices. Next, additional delivery devices will be discussed as well as several release assemblies that may be used with delivery and closure devices.

One configuration of relative movement between several control assemblies and a control anchor have been described for multi-stage deployment of the closure device 90, which includes a plurality of cells. In addition to the movement described above, movements may be performed in any order with any number of control assemblies and/or control anchors to deploy the closure device 90. Several delivery devices will be described herein which are configured to fully deploy the closure device 90. Each of the components may be combined as desired and are not limited to the use with devices or assemblies that may be discussed for context.

Figure 4:
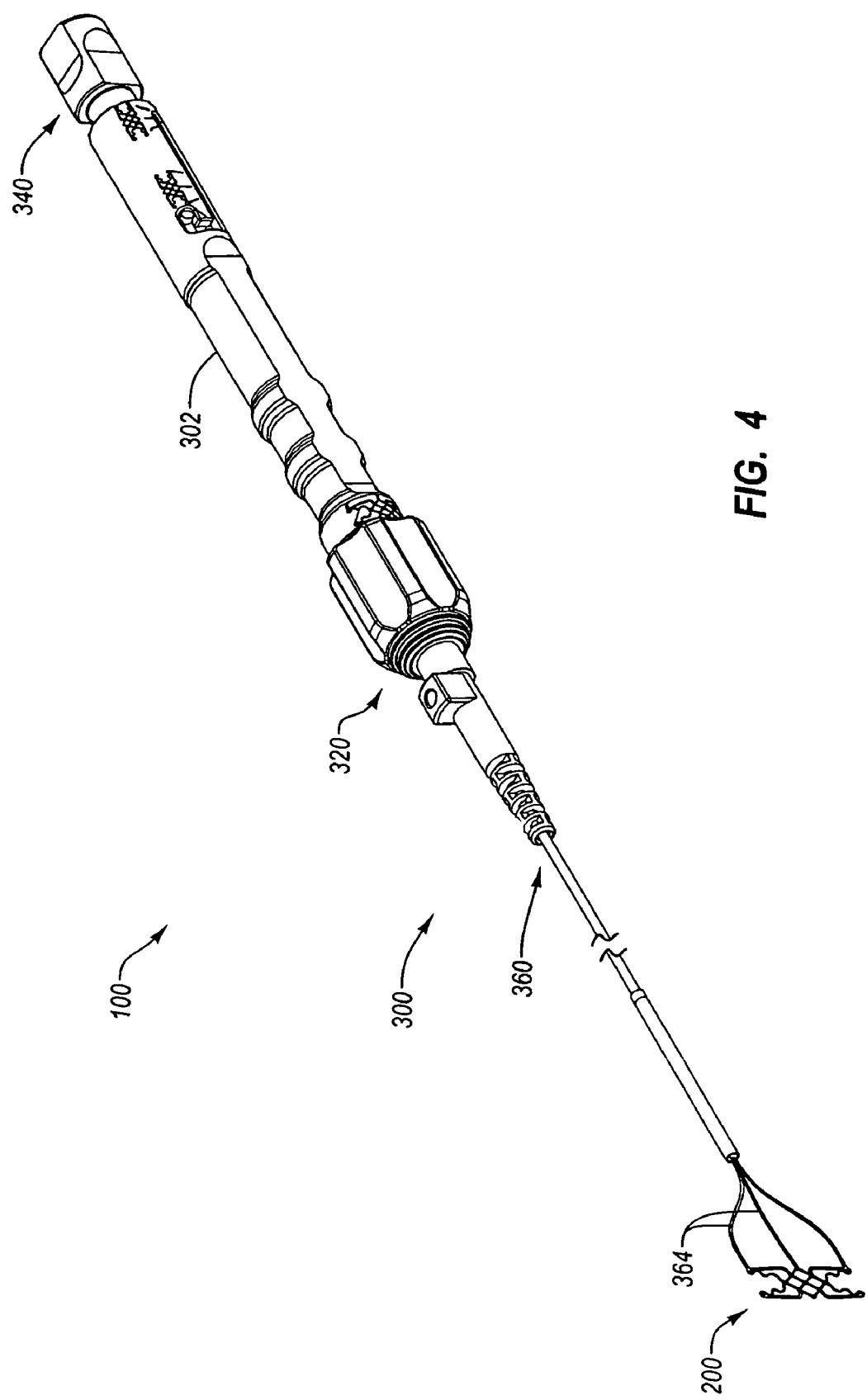
FIG. 4 illustrates a medical system according to one example.

FIG. 4 is a perspective view of a medical system 100 configured to facilitate closure of an internal tissue opening according to one embodiment of the present invention. In the illustrated embodiment, the medical system 100 comprises a closure device 200 adapted to reduce the size of the internal tissue opening and a delivery device 300 adapted to facilitate placement and deployment of the closure device 200 with respect to the internal tissue opening.

The medical system 100 of the present invention can provide benefits. For example, the medical system 100 can be configured to be used with different sizes, shapes and types of internal tissue openings. Furthermore, the medical system 100 can provide various safety measures to increase the safety and effectiveness of positioning the closure device 200. In addition, the medical system 100 can be configured to provide distributed lateral force to tissue of the internal tissue opening.

In the illustrated embodiment, delivery device 300 comprises a handle body 302, an actuating assembly 320 operatively associated with handle body 302, a release assembly 340 operatively associated with the handle body 302 and a delivery assembly 360 operatively associated with the actuating assembly 320, the release assembly 340 and the handle body 302. Handle body 302 can be configured to provide a gripping surface for a user. Handle body 302 can be used to position closure device 200, as well as facilitate deployment of the closure device 200 from the delivery assembly 360. Actuating assembly 320 can be moved with respect to handle body 302 to selectively deploy portions of the closure device 200 from the delivery assembly 360. For example, the actuation assembly 320 is configured to receive actuation inputs from a user to deploy the closure device 200 in one or more stages, as will be discussed more fully hereinbelow.

Delivery assembly 360 can house closure device 200 in a non-deployed orientation and facilitate deployment of closure device 200. Delivery assembly 360 can include one or more tethers 364 linked to the closure device 200 to facilitate selective deployment of the closure device 200 as well as the selective detachment of the closure device 200 from the delivery device 300. The configuration of the closure device 200 will first be discussed in more detail, followed by a discussion of deploying the closure device 200 with the delivery device 300.

Figure 5A:
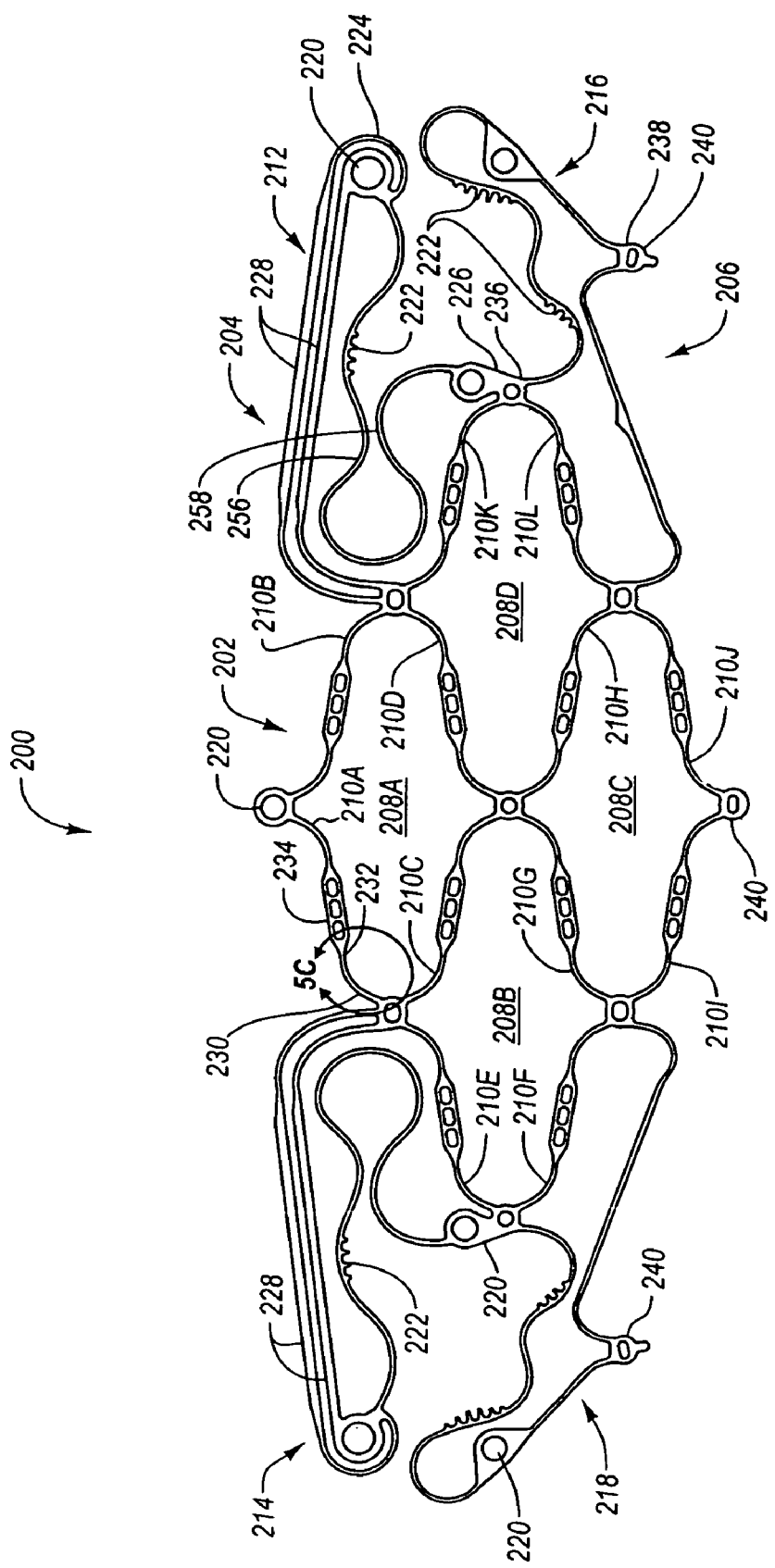

With reference to FIG. 5A, the closure device 200 is illustrated in a fully deployed, expanded, relaxed or non-constrained orientation. According to one embodiment of the invention, the closure device 200 can be configured to close an internal tissue opening, or to reduce the size of an internal tissue opening so as to close the internal tissue opening. In one embodiment, the closure device 200 can reduce the size of an internal tissue opening by approximating or, in other words, bringing together tissue of the internal tissue opening, such as tunnel tissue in a PFO. The closure device 200 can approximate tissue by applying lateral force to tissue of the internal tissue opening, as will be discussed more fully hereinafter. Also, the closure device 200 can be configured to enable a user to estimate the position and/or orientation of the closure device 200 with respect to an internal tissue opening, during and after positioning of the closure device 200 in the internal tissue opening.

According to one embodiment of the invention, the closure device 200 can be a non-tubular stent. The closure device 200 can be configured to assume a substantially flat configuration or, in other words, be configured to be substantially planar, such as illustrated in FIGS. 5A and 39M, for example. Furthermore, the closure device 200 can be configured to resist movement out of plane, such as plane 260 of FIG. 39M. However, the closure device 200 may bend out of plane when positioned in a tissue opening.

The closure device 200 according to one embodiment of the invention has many advantages. For example, the closure device 200 can be configured to be reliable and compliant. The configuration of the closure device 200 can enable the closure device 200 to be movable between a non-deployed orientation and a deployed orientation without causing failure or plastic deformation of the closure device 200. The closure device 200 can be used to close various types, shapes and sizes of internal tissue openings. Furthermore, the closure device 200 can accommodate for a range of PFO tunnel lengths, for example. Also, the closure device 200 can be partially or fully deployed from or received back into the delivery device 300. Closure device 200 can be configured to substantially conform to the size and shape of a tissue opening. For example, the undulations on the distal and proximal anchors can enable the anchors to substantially, or to a certain degree, conform to the anatomy of a tissue opening.

Generally, the closure device 200 can have a substantially flat aspect having a length and height greater than its depth or depth thickness. For example, in one embodiment, the closure device 200 has an overall length of 22 mm, a height of 7.5 mm and a depth thickness of 0.4 mm. According to one embodiment of the present invention, when the closure device 200 is in the relaxed or completely expanded orientation, as illustrated in FIG. 5A, the distance between the opposing ends of the proximal anchor 218 can be about 22 mm, the distance between the most proximal attachment member 240 of the body portion 202 and the most distal indicator 220 of the body portion 202 can be about 7.5 mm, and the depth thickness, designated as DT in FIG. 39M, of the closure device 200 can be about 0.4 mm.

Furthermore, the majority of segments comprising the closure device 200 can have a thickness or width that is substantially less than the depth thickness of the segments. The closure device 200 can resist out-of-plane movement due to the size and configuration of the segments. For example, the closure device 200 can be configured to assume a substantially flat configuration in a first plane. The configuration of the segments, for example, the segments having certain depth thickness, can facilitate the closure device 200 resisting movement out of the first plane in a manner similar to an I beam resisting bending in the direction of the web of the beam. The first plane can be plane 260 as illustrated in FIG. 39M.

Also, the closure device 200, according to one embodiment of the invention, can have a unitary construction or may be formed from multiple pieces. If the closure device 200 has a unitary construction, the closure device 200 can be cut from a single piece of material, such as cut by a laser, thereby removing the need to assemble or join different segments together. The closure device may also be formed of multiple pieces of material. A unitary construction can provide advantages, such as ease of manufacturing and reliability. For example, assembly is not required for a closure device having a unitary construction. Also, a closure device having a unitary construction may not include distinct elements or segments that require joining by joints, thereby reducing a likelihood of failure. The closure device 200 can be made from a super-elastic material, such as a super-elastic metal or a super-elastic polymer. Furthermore, the closure device 200 can be made from NiTiNol, stainless steel alloys, magnesium alloys, and polymers including bio-resorbable polymers.

In some embodiments according to the present invention, the closure device can be formed by utilizing a pressurized stream of water, such as a water jet, to remove material from a piece of material to form the closure device. Furthermore, it is contemplated that the closure device can be formed by utilizing one or more of the following: die casting, chemical etching, photolithography, electrical discharge machining, or other manufacturing techniques. It is contemplated that the closure device can be formed through use of a mill or some other type of device adapted to remove material to form a desired shape.

It will be appreciated by one of ordinary skill in the art in view of the disclosure provided herein that the closure device 200 can comprise multiple segments joined together by a known joining process, such as by an adhesive, by interference fits, crimping, by fasteners, or a weld, or some combination thereof. For example, in one embodiment, the closure device can include multiple segments joined together by various welds to form a closure device according to the present invention. In other embodiments, the segments can be joined together by a plurality of means, such as by the combination of welding, fasteners, and/or adhesives. The segments can be a wire or multiple joined or rolled wires crimped together or joined by a joining process to form the closure device 200.

In the illustrated embodiment, the closure device 200 includes a body portion 202, a first anchor 204 operatively associated with the body portion 202 and a second anchor 206 operatively associated with the body portion 202. The body portion 202 can be configured to facilitate application of lateral force against tissue of an internal tissue opening. Also, the body portion 202 can be configured to enable the closure device 200 be movable between a non-deployed and deployed orientation. For example, the closure device 200 can be configured to be self-expanding from the constrained or non-deployed orientation, as illustrated in FIG. 5B for example, to the relaxed orientation, as illustrated in FIG. 5A. In other words, the closure device 200 can have a preferential orientation, such that movement of the closure device 200 from a first orientation to a second orientation can create internal stresses in the closure device 200. These internal stresses can serve to bias the closure device 200 to the first orientation. For example, in one embodiment, the closure device 200 can have a preferential orientation of the relaxed or fully deployed orientation as illustrated in FIG. 5A. In this embodiment, movement of the closure device 200 to a constrained orientation, such as illustrated in FIG. 5B for example, can create internal stresses in the closure device 200, thereby creating in the closure device 200 a bias to return to the relaxed orientation.

In the illustrated embodiment, body portion 202 includes one or more cells 208 defined by a plurality of segments 210. The body portion 202 can include one or more apertures. In one embodiment, an aperture is defined by the cell 208 or, in other words, by the plurality of segments 210. In one embodiment, segment 210 can be a strut or a body support segment. Cells 208 can be distinct, or can be at least partially defined by a common segment. For example, cell 208A, as the distal-most cell, and cell 208C, as the proximal-most cell of body portion 202, are distinct and defined by distinct segments 210 with respect to each other. However, cell 208B is partially defined by a segment 210C, which also defines a portion of cell 208A. Similarly, cell 208B is partially defined by a segment 210G, which also partially defines cell 208C. Likewise, cell 208D shares a segment 210D with cell 208A and shares a segment 210H with cell 208C.

Segments 210 can be shaped and configured to have a substantially uniform stress at any given point along a certain length, when the segment 210 is deflected. For example, segment 210A can include a first portion 230 having a width or thickness greater than a second portion 232, wherein the width or thickness decreases from the first portion 230 to the second portion 232 or, in other words, is tapered, in a manner that provides for substantially uniform stress levels along the certain length. In other embodiments, segments can have a substantially constant width along their length.

FIG. 5C is a cut-out view of a portion of the closure device 200, including the first portion 230 and the second portion 232 of segment 210A. In the illustrated embodiment, the width or thickness of the segment 210A varies along the portion of the segment 210A from the location where segment 210A extends from the joining portion 254 that joins segment 210A to segment 210C to the intermediate portion 234. As the closure device 200 moves between an expanded or otherwise related orientation and a constrained or otherwise collapsed orientation, the segments 210 are deflected, with the highest levels of stress in the segment 210 being concentrated at the joining portion 254 and decreasing towards the intermediate portion 234. The segments 210 can be configured in a manner so as to have a substantially equal stress level along the length of the segment 210 between the joining portion 254 and the intermediate portion 234. The uniform stress level can be accomplished by having the width of the segment 210 vary from the first portion 230 to the second portion 232 in a calculated manner. In one embodiment, the width of the first portion 230 of the segment can be about 0.1 mm and the taper to a width of about 0.05 mm at the second portion 232 of the segment.

In other embodiments, the uniform stress level can be accomplished by utilizing a gradient of material having varying properties. In other embodiments, the segment 210 can have varying widths along its length and comprise a gradient of material sufficient to achieve a substantially uniform stress level between the first portion 230 and the second portion 232 of the segment. In the illustrated embodiment, the first portion is adjacent the joining portion 254 and the second portion is adjacent the intermediate portion 234. In yet additional embodiments, the joints of the interconnecting segments can include a biasing member, such as a spring, thereby enabling the segments to move relative to each other to collapse or expand the closure device 200. Furthermore, the biasing member of the joint can cause the segments to have a preferential orientation with respect to each other.

With continued reference to FIG. 5A, segments 210 can also be configured to have a rectangular cross-section. In other embodiments, segments 210 can have an oval-shaped cross-section. In yet another embodiment, sections 210 can have a round or rounded cross-section. Furthermore, in one embodiment, the ratio, or aspect ratio, of the thickness or width to the depth thickness of the first and second portions 230, 232 can range between at least about 1:2 to about 1:20. In one embodiment, the aspect ratio of the width to the depth thickness of the first portion 230 can be at least 1:2 and the ratio of the width to the depth thickness of the second portion 232 can be at least 1:4. In an alternative embodiment, the aspect ratio of the first portion 230 can be about 1:4 and the aspect ratio of the second portion 232 can be about 1:8. In this manner, the closure device 200 can substantially resist out-of-plane movement, while allowing in-plane movement during reorientation of various portions of the closure device 200.

Segments 210 can be configured to be compliant. Compliancy of segments 210 can enable cells 208, and thus the body portion 202, to be oriented in various orientations. For example, body portion 202 can be oriented or, in other words, moved, between a non-deployed orientation, such as illustrated in FIG. 5B, and a fully deployed orientation, such as illustrated in FIG. 5A. The compliancy of segments 210 can facilitate the accommodation by the closure device 200 of a variety of types, shapes and sizes of internal tissue openings. For example, the size and configuration of the first and second anchors 204, 206 and the body portion 202 can enable the closure device 200 to accommodate varying sizes, shapes and types of internal tissue openings. In one implementation, the first anchor 204 can engage wall tissue of an internal tissue opening and the second anchor 206 can engage only the tunnel tissue of the internal tissue opening to approximate tissue. In an alternative implementation where the internal tissue opening has a shorter tunnel length, the second anchor 206 can engage the tunnel tissue and an opposing wall of the internal tissue opening to approximate tissue.

Segments 210 can include an intermediate portion 234 configured to facilitate securement of in-growth materials to the closure device 200, or can be used as an indicator 220 to facilitate estimation of the position of the closure device 200 with respect to an internal tissue opening. Furthermore, intermediate portion 234 can be configured to facilitate measuring of a characteristic of an internal tissue opening. In one embodiment, intermediate portion 234 can include one or more apertures. The apertures can be configured to receive a securing element, such as a thread, therethrough to facilitate securing an in-growth material to the closure device 200. Intermediate portion 234 can be configured to be stiffer or more rigid than first portion 230, second portion 232, or both. A stiffer intermediate portion 234 can increase the reliability of segments 210.

In another embodiment, the intermediate portion 234 can include an indicator 220, such as a dense metallic rivet or concentration of dense material, for use in estimating the orientation and/or position of the closure device 200. Understanding of the orientation and/or position of the closure device 200 can facilitate estimating a physical characteristic of an internal tissue opening and/or the relative position of the closure device 200 with respect to the internal tissue opening. For example, if the distance between the indicators 220 is known, a practitioner can estimate a physical characteristic, such as the opening or tunnel width, by determining the new distance between the indicators 220 when the closure device 200 is positioned in the tissue opening. Similarly, indicators 220 can be positioned on the first and second anchors 204, 206. The indicators 220 can be configured and arranged on the closure device 200 such that when the first anchor 204 is deployed, the indicators 220 are substantially aligned. In this manner, a practitioner can estimate whether the first anchor 204 has fully deployed.

In some cases, it may be difficult to view the closure device 200 in the event the closure device 200 is at a skewed angle with respect to the viewing plane, such as a fluoroscope. When the closure device 200 is skewed in this manner, it can be difficult to determine accurately the distance of interest. However, when various distances between indicators is known, a user can use the known distances to calculate the distances of interest by using geometry.

In one embodiment, segments 210 along a similar or common lateral plane can have substantially equal lengths. Substantially equal lengths of segments 210 in this manner can enable body portion 202 to be moved between the non-deployed and deployed orientation without failure of the segments 210. For example, in one embodiment, segments 210A and 210B have substantially the same length, segments 210E, 210C, 210D, and 210K have substantially the same length, segments 210F, 210G, 210H and 210L have substantially the same length, and segments 210I and 210J have substantially the same length. In this configuration, body portion 202 can be collapsed or oriented into the non-deployed orientation, as illustrated in FIG. 5B, without causing damage to the body portion 202 of closure device.

The closure device 200 can be configured to have a preferential orientation of the fully deployed orientation as illustrated in FIG. 5A. As the closure device 200 is deployed from the delivery device 300, the configuration of closure device 200 can cause the closure device 200 to preferentially move toward the fully deployed orientation. Thus, as the closure device 200 is deployed in an internal tissue opening, the preferential orientation of the closure device 200 can cause the closure device 200 to apply lateral force to the tissue of the internal tissue opening. In other words, the body portion 202, first anchor 204 and the second anchor 206 are deflected by an applied force in order to reorient the closure device 200 from the fully deployed orientation to a non-deployed orientation, for example. In this manner, the closure device 200, because of the deflection of the body portion 202, first anchor 204 and the second anchor 206, will have tendency to return to the fully deployed orientation. When the closure device 200 is positioned in an internal tissue opening, the deflected body portion 202, first anchor 204 and the second anchor 206 can have a tendency to apply a lateral force to tissue of the opening as the closure device 200 attempts to return to the fully deployed orientation.

Body portion 202 can be operatively associated with the first anchor 204 and the second anchor 206. First and second anchors 204, 206 can be configured to move between a deployed and non-deployed orientation. First and second anchors 204, 206 can be configured to apply lateral force to tissue of an internal tissue opening, and to engage and/or contact a portion of wall tissue and/or tunnel tissue of an internal tissue opening. In one embodiment, the first anchor 204 can be a left atrial anchor, and the second anchor 206 can be a right atrial anchor.

In the illustrated embodiment, the first anchor 204 can include a first anchor segment 212 and an opposing second anchor segment 214. Likewise, the second anchor 206 can include a first anchor member 216 and an opposing second anchor member 218. The first anchor segment 212 can be configured to move relative to the second anchor segment 214. Likewise, the first anchor member 216 can be configured to move relative to the second anchor member 218. In this manner, the closure device 200 can accommodate for a variety of types, shapes and sizes of internal tissue openings. The first anchor segment 212 and the second anchor segment 214 can be configured to be substantially similar in size, shape and configuration. As such, reference to the configuration and/or function of one of the first or second anchor segments can apply to the other anchor segment. In one embodiment of the invention, the first anchor 204 and/or the second anchor 206 can include one or more undulations. The undulations can facilitate reorienting or movement of the anchors with respect to the body portion 202, for example, from a deployed to a non-deployed configuration. Furthermore, the undulations can facilitate the anchor substantially conforming to the anatomy of the tissue opening.

The first anchor segment 212 can include a distal end 224 and a proximal end 226. The first anchor segment 212 can be defined by various segments and can include reinforced segments 228 and one or more engaging members 222. For example, in the illustrated embodiment, the first anchor segment 212 is at least partially defined by segment 210K of cell 208D. The engaging members 222 can be microposts or tines configured to contact and/or engage tissue. The engaging members 222 can include a sharp tip or can be blunt. The engaging members 222 can be configured to provide a degree of surface texture in order to increase engagement of the first anchor 204 with tissue.

The first anchor segment 212 can be configured to be moved between a non-deployed orientation, as illustrated in FIG. 5B, and a fully deployed orientation, as illustrated in FIG. 5A. The first anchor segment 212 can be configured such that the distance from the proximal end 226 to the distal end 224 of the segment which includes the engaging members 222 is substantially equal to the distance from the proximal end 226 to the distal end 224 of the segment that includes the reinforced segments 228 and segment 210K. The second anchor segment 214 can be configured similar to the first anchor segment 212.

First anchor segment 212 can be configured to define a closed periphery. For example, first anchor segment 212 can include the reinforced segment 228 extending from the body portion 202 to the segment having the engaging members 222 that is connected to segments 210K, 210L to define a closed periphery with segment 210K. Furthermore, two reinforced segments 228 can extend from the joining portion 254 of the body portion 202 and join together near the distal end 224 of the first anchor 204. As such, there are multiple anchor portions extending from the body portion 202. In this manner, anchors of the present invention are reinforced to provide greater rigidity and strength to facilitate stabilization and maintenance of the closure device 200 within a tissue structure.

First anchor member 216 can include a distal end 236 and a proximal end 238. The first anchor member 216 can be defined by various segments and can include one or more engaging members 222. For example, in the illustrated embodiment, the first anchor member 216 is at least partially defined by segment 210L of cell 208D. The engaging members 222 can be microposts or tines configured to contact and/or engage tissue. The engaging members 222 can include a sharp tip or can be blunt. The engaging members 222 can be configured to provide a degree of surface texture to increase engagement of the second anchor 206 with tissue.

It will be understood by one of ordinary skill in the art in view of the disclosure provided herein that the engaging members 222 can vary in size and shape, and can be positioned at various locations on the closure device 200. In alternative embodiments, one or more engaging members can extend out of plane of the closure device so as to contact tissue which is perpendicular, for example, to the substantially flat plane, such as plane 260 of FIG. 11B, of the closure device 200.

The first anchor member 216 can be configured to be moved between a non-deployed orientation, as illustrated in FIG. 5B and a fully deployed orientation, as illustrated in FIG. 5A. The first anchor member 216 can be configured such that the distance from the proximal end 238 to the distal end 236 of the segment that includes the engaging members 222 is substantially equal to the distance from the proximal end 238 to the distal end 236 of the segment that includes segment 210L. In this manner, first anchor member 216 can be detachably coupled to the delivery device 300 when in a non-deployed orientation inside the delivery device 300 as illustrated in FIG. 5B. The second anchor member 218 can be configured similar to the first anchor member 216.

The first anchor segment 212 can also include a first portion 256 and a second portion 258 configured to facilitate engagement of the internal tissue opening. For example, first anchor segment 212 can be configured to include one or more undulations causing the first portion 256 to be positioned in close proximity with second portion 258. In this manner, as tissue is positioned between the first and second portions 256, 258, the configuration of the first anchor segment 212 can engage or, to some degree, pinch the tissue therebetween to facilitate maintenance of the position of the closure device 200 with respect to the tissue opening.

The closure device 200 can also include attachment members 240 for use in detachably linking the closure device 200 to the delivery device 300, as will be discussed more fully hereinafter. The attachment members 240 can include an aperture 242 for use in facilitating the linking of the closure device 200 to the delivery device 300.

FIG. 5B illustrates the closure device 200 in a non-deployed or constrained orientation. The configuration of the body portion 202, and the first and second anchors 204, 206 enables the closure device 200 to be reoriented from the fully deployed and preferential orientation, as illustrated in FIG. 5A, to the non-deployed or collapsed orientation as illustrated. In the collapsed or non-deployed orientation, the first anchor 204 extends distally and the second anchor 206 extends proximally, with the attachment members 240 being the proximal-most portions of the second anchor 206 and the body portion 202.

In the illustrated embodiment, the closure device 200 is positioned inside of a delivery portion 366 of the delivery device 300. The configuration of the closure device 200 can cause portions of the closure device to apply force to the wall of the delivery portion 366 due to the preferential orientation of the closure device 200. The closure device 200 is configured to be received into and deployable from the delivery portion 366.

FIG. 6 illustrates one embodiment of the delivery device 300. In the illustrated embodiment, the delivery assembly 360 includes a catheter 362 having a delivery portion 366, and a plurality of tethers 364 at least partially housed by the catheter 362. The tethers 364 can be configured to facilitate selective detachment of the closure device 200 from the delivery device 300. The delivery portion 366 can be configured to receive the closure device 200 therein. The catheter 362 can be coupled to the actuating assembly 320, such that movement of the actuating assembly 320 can cause movement of the catheter 362.

In the illustrated embodiment, the actuating assembly 320 includes a first member 322 operatively associated with the handle body 302, a second member 324 operatively associated with the first member 322 and the handle body 302, and a knob 338 linked to the first member 322. The actuating assembly 320 can be utilized by a user to selectively deploy the closure device 200 from the catheter 362. As will be discussed in more detail below, a practitioner can move the knob 338, which is coupled to the first member 322, in the proximal direction to deploy first anchors 204 (FIG. 4). Thereafter, the second member 324 can be rotated in order to selectively deploy the remaining portions of the closure device 200 from the delivery portion 366 of the delivery device 300.

In addition to providing for a two-step deployment process, the exemplary delivery device 300 illustrated in FIG. 6 is also configured to allow a practitioner to estimate the progress of the deployment process. In particular, the handle body 302 can include indicia 304 to enable a user to estimate the degree of deployment of the closure device 200 from the delivery device 300, as well as predict detachment of the closure device 200 from the delivery device 300. For example, indicia 304 can include deployment indicia 306 and release indicia 308. Deployment indicia 306 can be utilized to enable a user to estimate the degree of deployment of the closure device 200 from the catheter 362, and the release indicia 308 can be utilized to predict the detachment of the closure device 200 from the delivery device 300. The handle body 302 can also include a release pin groove 310. The release pin groove 310 can be operatively associated with the release assembly 340 to facilitate the selective detachment of the closure device 200 from the tethers 364.

According to one embodiment of the invention, the release assembly 340 can include a biasing member 342 operatively associated with the handle body 302 to facilitate detachment of the closure device 200. A release knob 346 can be provided to manipulate the position of biasing member 342 in order to release or detach the closure device 200. In one embodiment, the release knob 346 is coupled to the biasing member 342, such that movement of the release knob 346 can cause movement of the biasing member 342 relative to the handle body 302 to thereby cause separation between the handle body 302 and the release knob 346. In the present example, release knob 346 is operatively associated with the tethers 364A-364C, such that as the release knob moves proximally relative to the handle body 302, the tethers 364A-364C are drawn proximally to release closure device 200. Specifics of the operation of the release assembly 340 and other release assemblies will be discussed in more detail below.

FIG. 7A is a cross-sectional view of the distal end of the catheter 362. In the illustrated embodiment, the catheter 362 includes a delivery portion 366 for use in positioning the catheter 362. The catheter 362 can be made from a resilient material having sufficient axial stiffness to allow a practitioner to position the catheter 362 with respect to an internal tissue opening, and sufficient rotational stiffness to allow a practitioner to rotate the catheter 362 by rotating the handle body 302. In one embodiment, the catheter 362 comprises a braided polyimide. In other embodiments, the catheter 362 can be made from a material having a sufficient axial stiffness, such as a braid of reinforced polymer, axially reinforced polymer, metal reinforced polymer, carbon reinforced polymer, or some other type of axially stiff material. The delivery portion 366 can be made from a thermoplastic elastomer, such as PEBAX®. In other embodiments, the delivery portion or tip portion 366 can be made from a material having sufficient flexible properties, such as a polymeric material. In other embodiments, the delivery portion 366 can include a combination of materials, such as metallic materials and polymeric materials.

The delivery portion 366 can define a lumen 368 to facilitate placement of the catheter 362. For example, a guidewire can be received in the lumen 368 to guide the catheter 362 to a desired location. In this manner, the closure device 200 can be located proximate to the internal tissue opening in a quick and efficient manner. Furthermore, the delivery portion 366 can be shaped, such as including a bend, in order to facilitate placement of the delivery portion 366 through a PFO, for example. In one embodiment of the invention, the catheter 362 can be considered a rapid exchange catheter wherein the delivery or tip portion 366 enables a guidewire to be linked to the catheter 362 in a quick and efficient manner for placement of the catheter 362.

The catheter 362 and delivery portion 366 can be configured to at least partially house tethers 364 in a lumen that is distinct and separate from lumen 368. For example, lumen 368 can be in a spaced apart, non-coaxial arrangement from the lumen that houses tethers 364, such that a guidewire can be received through lumen 368 without being introduced into the lumen or space in which the tethers 364 are housed. In this manner, a user can introduce a guidewire into the lumen 368 at the distal end of the catheter 362, rather than the lumen that at least partially houses the tethers 364, which would require the guidewire to be introduced into the lumen at the proximal end of the catheter 362. In alternative embodiments, the lumen 368 configured to receive the guidewire therein can be positioned inside the lumen that houses the tethers 364. In this embodiment, lumen 368 would include an opening and an exit at the distal end of the catheter 362 in order to facilitate the quick placement of a guidewire through the lumen 368.

In one embodiment, catheter 362 can include a rounded cross-section and the delivery portion 366 can include a rectangular cross-section. The rectangular cross-section of the delivery portion 366 can facilitate proper deployment of the closure device 200 from the delivery device 300, as well as facilitate the closure device 200 being reintroduced back into the delivery portion 366. The rectangular cross-section of the delivery portion 366 can be sized to orient the tethers 364 next to each other in a linear fashion. In this manner, the likelihood that the tethers 364 cross each other upon reintroduction of the closure device 200 into the delivery portion 366 can be reduced.

In one embodiment of the invention, tethers 364 includes three tethers 364A-364C, each tether 364 being sized and configured to attach to and/or accommodate therein an attachment member 240 of the closure device 200. One example of a tether is a line or hollow tube coupled to the handle body 302. The tether 364 can comprise a flexible, hollow shaft having sufficient stiffness such that as actuating assembly 320 moves the catheter 362 proximally with respect to the handle body 302, the closure device 200 is forced out of the delivery portion 366. Likewise, the tether 364 can be configured to pull the closure device 200 back into the delivery portion 366 as the actuating assembly 320 is moved distally with respect to the handle body 302.

In one embodiment, the tethers 364 can be a coil of stainless steel covered by a heat-shrunk tubing to give the coil a degree of tensile strength and rigidity. In an alternative embodiment, the tether 364 can be a polymeric tube. In yet an additional embodiment, the tether 364 can be a combination of polymeric materials and metallic materials. In some embodiments, additional heat-shrunk tubing covers a proximal segment of the three tethers 364A-364C. The heat-shrunk covering can increase the column strength of the tether 364, which can enable the tethers 364 to assist with deployment and reintroduction of the closure device 200 from and into the delivery portion 366. The tethers 364 can have a distal tip configured to correspond to the shape and size of the attachment members 240 of the closure device, such that the attachment member 240 can be received into the distal tip of the tether 364, as illustrated in FIG. 7B.

Tethers 364 can be made from a material having sufficient flexibility to substantially prevent distortion or otherwise influence the orientation of the closure device 200 when the closure device is deployed from the catheter 362, yet have sufficient axial strength to facilitate deployment of the closure device 200 when the catheter 362 is moved proximally with respect to the closure device 200. The tethers 364 can have a lumen extending therethrough of sufficient size and configuration to enable a plurality of wires 378 to be housed and movable therein.

Figure 7B:
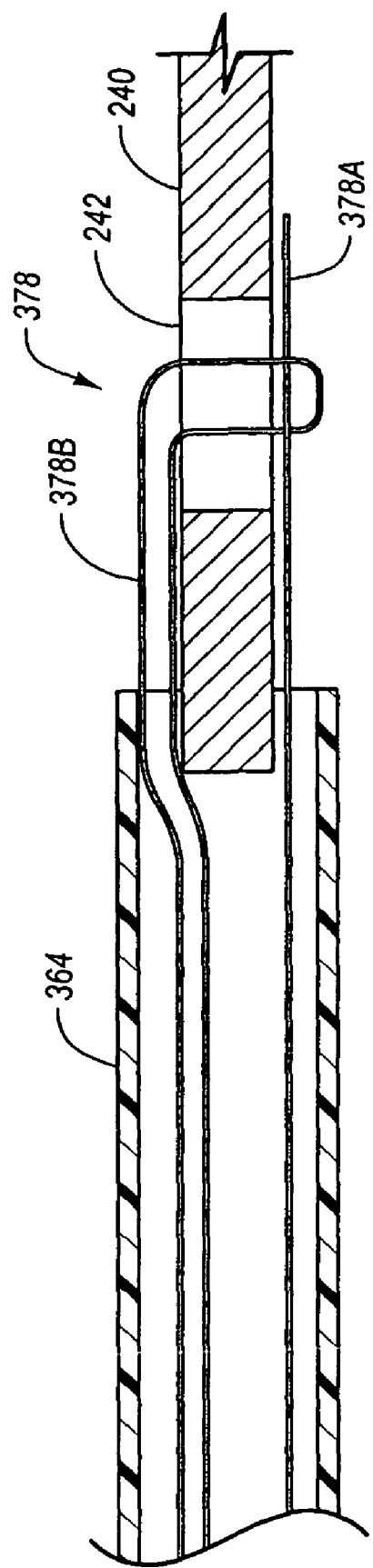

Illustrated in FIG. 7B is a cross-sectional view of attachment member 240 of the closure device 200 received into a tether 364 and coupled by first and second wires 378A, 378B. In the illustrated embodiment, a second wire 378B can extend through and out of the tether 364 and form a loop. The loop can extend through an aperture 242 of the attachment member 240 of the closure device 200. With the loop of second wire 378B positioned through the aperture 242 of the attachment member 240, a first wire 378A, which extends through and out of the tether 364, can extend through the loop of the second wire 378B to form a locking feature. When the first wire 378A extends sufficiently through the loop of the second wire 378B, the closure device 200 can remain coupled to the delivery device 300 until the first wire 378A is pulled through the loop of the second wire 378B, and the second wire 378B is pulled out of the aperture 242 of the attachment member 240.

The first wire 378A and the second wire 378B can be attached at their proximal ends to the biasing member 342 (FIG. 6). Accordingly, the first and second wires 378A, 378B extend from the distal end of the closure device 200 through the tethers 364A-364C to the biasing member 342. In this manner, movement of the biasing member 342 in the proximal direction can cause movement of the wires 378A, 378B also in the proximal direction.

Figure 7C:
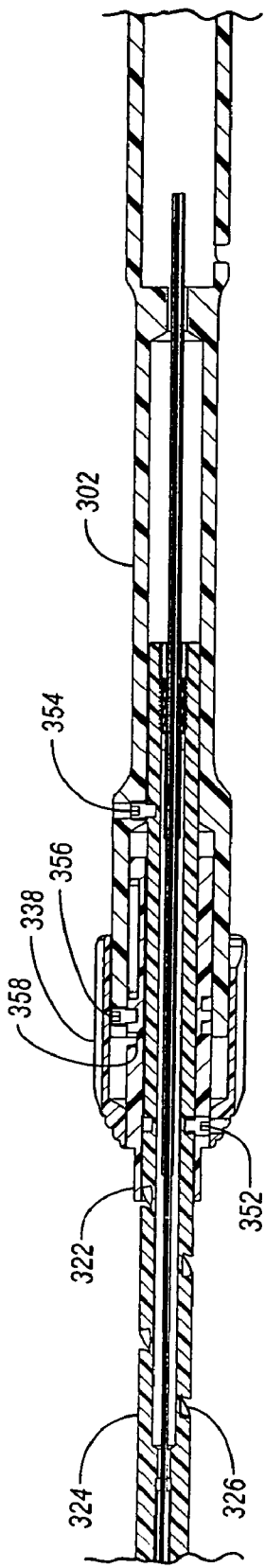
Figure 7D:
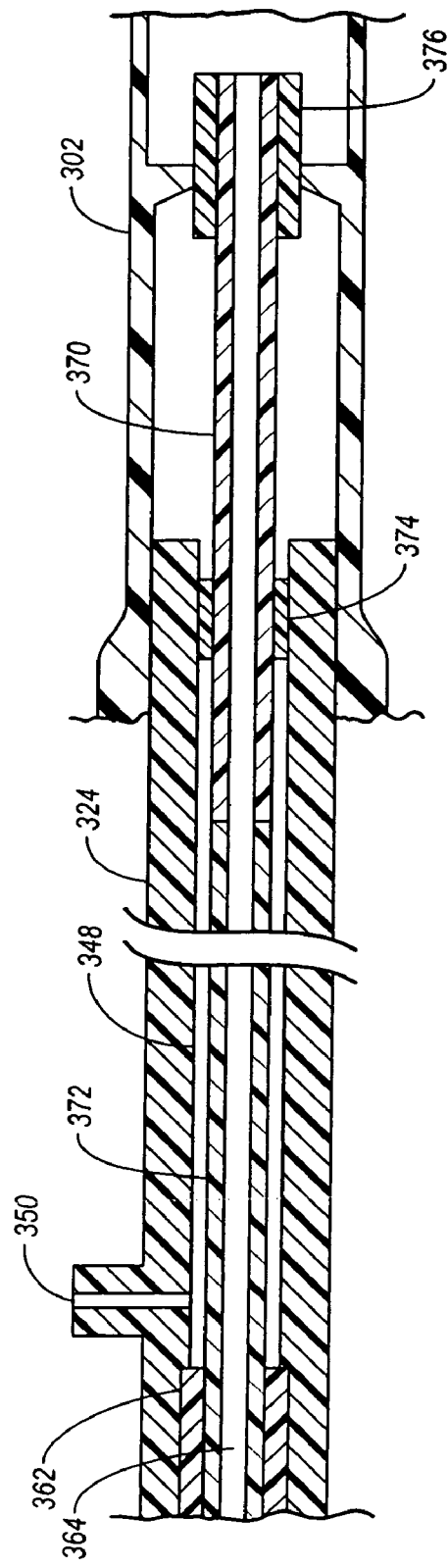

FIGS. 7C-7D are cross-sectional views illustrating the delivery assembly 360 in association with the actuating assembly 320. However, simplicity, FIG. 7C does not include the biasing member 342, release wires 378A, 378B and associated release knob 346, while FIG. 7D illustrates details about the interaction between the delivery assembly 360 and the actuating assembly 320 without illustrating the first member 322 and details about the handle body 302 and the second member 324. In the illustrated embodiment, the proximal end of the catheter 362 is coupled to the distal end of the second member 324. In this manner, movement of the second member 324 can cause a corresponding movement in the catheter 362. For example, as the second member 324 moves proximally with respect to the handle body 302, so also does the catheter 362 move proximally with respect to the handle body 302.

According to one embodiment of the invention, the tethers 364 can extend from the delivery portion 366, through the catheter 362 and the second member 324 and are coupled to the handle body 302. In at least one example, the tethers 364 are coupled to the handle body 302 while the first and second members 322, 324 may be coupled to the catheter 362 such that movement of the first and second members 322, 324 causes relative movement between the catheter 362 and handle body 302, which results in movement between the catheter 362 and the tethers 364A-364C. The tethers 364A-364C are secured to the closure device 200, such that movement of the tethers 364A-364C results in deployment of the closure device. As a result, movement of the first and second members 322, 324 deploys the closure device 200, as will now be discussed in more detail.

The tethers 364 can be secured to the handle body 302 by, for example, an intermediate member 376. The tethers 364 can be covered with a first and second housing 370, 372 to provide a degree of rigidity to the portions of the tethers 364 located inside of the handle body 302 and the second member 324. For example, in one embodiment, the first housing 370 comprises a rigid, hollow metal rod configured to house the three tethers 364A-364C therein. The first housing 370 can extend from the intermediate member 376, which facilitates securement of the tethers 364 to the handle body 302, and terminate at some point beyond the handle body 302.

In the illustrated embodiment, the second housing 372 can extend from the distal end of the first housing 370 and extend into the catheter 362. The second housing 372 can comprise a resilient material configured to resist axial stretching while allowing a degree of bending. In one embodiment, the second housing 372 comprises a coil of metal, such as stainless steel, configured to resist axial stretching, yet allow a degree of bending. The second housing 372 can allow a practitioner to bend a portion of the catheter 362, if needed, in order to manipulate delivery device 300 for placement of the closure device 200. A seal 374 can be provided between the first housing 370 and the second member 324 in order to reduce or substantially prevent bodily fluid, which may have entered the catheter 362, from entering the handle body 302 or otherwise inappropriately being expelled from the delivery device 300.

In the illustrated embodiment, the second member 324 can comprise an elongate shaft defining an axial lumen 348 and a lumen 350 in fluid communication therewith. Lumen 350 can be configured to couple to a medical device for removal of fluid from the delivery device 300. The axial lumen 348 can be sized to accommodate and allow movement of the tethers 364, the first housing 370 and the second housing 372 therein. The second member 324 can include a guide 326. The guide 326 can be configured to cooperate with a first pin 352 and a second pin 354 to influence movement of the second member 324 with respect to the handle body 302, as will be discussed more fully hereinbelow.

In the illustrated embodiment, the first member 322 comprises a hollow elongate tube sized and configured to enable the second member 324 to be received into and moveable within the first member 322. The first member 322 can be operatively associated with the handle body 302 and the second member 324 to facilitate deployment of the closure device 200. For example, the first member 322 is linked to the handle body 302 by a third pin 356. The third pin 356 is received in a guide 358 of the first member 322. The guide 358 is configured to interact with the third pin 356 in order to influence the movement of the first member 322 with respect to the handle body 302.

The first pin 352 can link the first member 322 to the second member 324. When the first pin 352 links the first member 322 to the second member 324, the second pin 354 links the handle body 302 to the second member 324, and the third pin 356 links the handle body 302 to the first member 322, movement of the first member 322 can selectively deploy the closure device 200 from the delivery portion 366.

Figure 8:
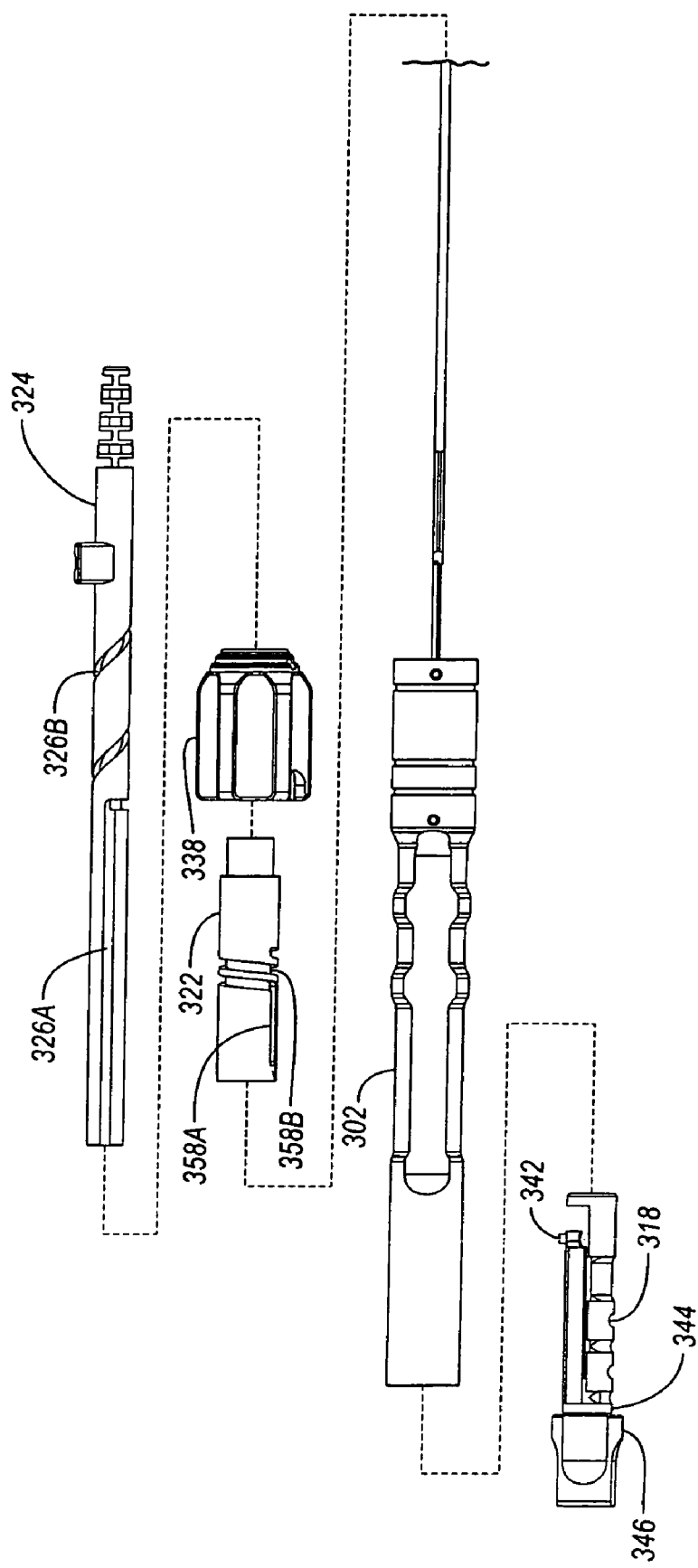
FIG. 8 illustrates an exploded view of a delivery device according to one example.

FIG. 8 is an exploded view of the actuating assembly 320 and the release assembly 340. The second member 324 is received into the first member 322, and the first member 322 is received into the knob 338 and the handle body 302. The second member 324 can include a guide 326 having a first portion 326A and a second portion 326B, which guide 326 can be defined by a slot formed on the outer surface of the second member 324. In the illustrated embodiment, the first portion 326A is straight and extends along at least a portion of the length of the second member 324 and joins with the second portion 326B of the guide 326. The second portion 326B can include a helical groove or slot that begins with and is contiguous with the first portion 326A and extends distally therefrom.

The guide 326 of the second member 324 is configured to interact with the handle body 302 and the first member 322 to selectively retract the catheter 362 in order to deploy the closure device 200. For example, the first portion 326A of the guide 326 is configured to interact with the second pin 354, which is secured into the handle body 302 by means of threads and extend into the first portion 326A of the guide 326. In this manner, the second member 324 can move laterally with respect to the handle body 302. Thus, rotation of the handle body 302 can translate to rotation of the second member 324, and thus, the catheter 362 and the delivery portion 366.

The second portion 326B of the guide 326 is configured to interact with the first pin 352, which is secured to the first member 322 by means of threads and extends into the second portion 326B of the guide 326. In this manner, as the first member 322 is rotated, the first pin 352 will interact with the second portion 326B to move the second member 324 in the proximal direction. As the second member 324 is moved in the proximal direction with respect to the handle body 302, the catheter 362 moves proximally with respect to the handle body 302 thereby exposing or deploying the closure device 200 from the delivery portion 366.

In the illustrated embodiment, the first member 322 can include a guide 358 defined by a slot or groove formed in the outer surface of the first member 322. In the illustrated embodiment, the guide 358 can include a first portion 358A connected to a second portion 358B. The first portion 358A of guide 358 can be straight and extend along at least a portion of the length of the first member 322 and then join and be contiguous with the second portion 358B. The second portion 358B of the guide 358 can be a helical groove that wraps around at least a portion of the outer surface of the first member 322 and extends along at least a portion of the length of the first member 322.

As described previously, the third pin 356, which is secured to the handle body 302 by means of threads, can extend into the guide 358 in order to influence movement of the first member 322 with respect to the handle body 302. For example, as the third pin 356 is positioned in the most proximal portion of the first portion 358A, the closure device 200 is completely received into and enclosed by the delivery portion 366. As the first member 322 is moved in the proximal direction as illustrated by the arrow in FIG. 4, the third pin 356 moves in the first portion 358A of the guide 358 to deploy the first anchor 204 of the closure device 200 from the delivery portion 366.

The length of the first portion 358A can correspond with the distance that the first member 322, and thus the catheter 362, must move in order to deploy the first anchor 204 of the closure device 200 from the delivery portion 366. For example, a practitioner can move the knob 338, which is coupled to the first member 322, in the proximal direction. Movement of the knob 338 in the proximal direction can cause the third pin 356 to move linearly in the first portion 358A of the guide 358. In this manner, the second member 324 can move correspondingly with the first member 322 because of the first pin 352, which links the first member 322 to the second member 324. As the third pin 356 is positioned in the location of the guide 358 where the first portion 358A meets with the second portion 358B, the first member 322 can be rotated in order to selectively deploy the remaining portions of the closure device 200 from the delivery portion 366 of the delivery device 300.

As the first member 322 is rotated, the third pin 356 is positioned in the second portion 358B to influence movement of the first member 322 with respect to the handle body 302, and the first pin 352, which is coupled to the first member 322, interacts with the second portion 326B of the guide 326 to move the second member 324 in the proximal direction with respect to the handle body 302. Movement of the second member 324 in the proximal direction in this manner can cause further deployment of the closure device 200 from the delivery portion 366. As will be appreciated, the knob 338 can be coupled to the first member 322 to facilitate and enable movement of the first member 322 with respect to the handle body 302.

The dual movement required to deploy the closure device 200 can provide some efficiency and safety advantages. For example, a practitioner can move the knob 338 in a first direction (i.e., proximally in a linear fashion) to deploy the first anchor 204 from the delivery portion 366. Thereafter, the practitioner can move the handle body 302 to position the first anchor 204 against the wail tissue of an internal tissue opening, such as against the left atrial wall of a heart, for example. Once the first anchor 204 is positioned against the wall, the practitioner can move the knob 338 in a second direction (i.e., rotate the knob) to further deploy the closure device 200 from the delivery portion 366. The dual movement enables a user to predict the deployment of the closure device 200 to reduce the risk of premature deployment of the closure device.

It will be understood by one of ordinary skill in the art in view of the disclosure provided herein that other means of controlling movement of one member with respect to the other, such as the first member with respect to the second member, can be utilized without departing from the scope and spirit of the invention. For example, a structure configured to substantially restrict or control movement of the first element with respect to the second element and/or handle body can be utilized. In one embodiment, the structure can include a cam and a follower. In an alternative embodiment, the structure can include a slider.

The release assembly 340 can be configured to be received in the proximal end of the handle body 302. The release assembly 340 can be configured to provide additional safety features for the practitioner and patient by reducing the risk of premature detachment of the closure device 200 before it is positioned appropriately in an internal tissue opening. For example, a practitioner using the medical system 100 of the present invention can manipulate the actuating assembly 320 to deploy the closure device 200 for positioning in an internal tissue opening. In order to deploy a first portion of the closure device 200, a user can move the knob 338, and thus the first member 322, in the proximal direction with a first movement, which is a linear movement, and then deploy the remaining portions of the closure device 200 by a rotational movement. Once the closure device 200 is deployed, the practitioner can be required to move their hands in order to utilize the release assembly 340 to release the closure device 200 from the delivery device 300.

In the illustrated embodiment, the release assembly 340 can include a release knob 346 coupled to a biasing member 342, which is received into the proximal end of the handle body 302. The biasing member 342 can be configured to include a plurality of slots 318 configured and arranged to act similar to a spring. The slots 318 can be configured and arranged in the biasing member 342 to enable at least a portion of the biasing member 342 to be compressed. Compression of the biasing member 342 can cause the release pin 344 to move toward the distal end of the biasing member 342.

The biasing member 342 can be configured such that when biasing member 342 is positioned in the handle body 302, the biasing member 342 naturally tends to maintain its position with the release pin 344 in the release pin groove 310 as illustrated in FIG. 8. As force is applied to the release knob 346 in the distal direction (i.e., compress the biasing member 342), the release pin 344 can be moved out of a terminating portion of the release pin groove 310 and rotated and moved into a proximal terminating portion of the release pin groove 310 to release the closure device 200 from the delivery device 300.

The closure device 200 is released from the delivery device 300 by moving a plurality of wires 378 that are housed by a tether 364 and coupled to the biasing member 342. Illustrated in FIG. 7 is a cross-sectional view of attachment member 240 of the closure device 200 received into a tether 364 and coupled by first and second wires 378A, 378B. In the illustrated embodiment, a second wire 378B can extend through and out of the tether 364 and form a loop. The loop can extend through an aperture 242 of the attachment member 240 of the closure device 200. With the loop of second wire 378B positioned through the aperture 242 of the attachment member 240, a first wire 378A, which extends through and out of the tether 364, can extend through the loop of the second wire 378B to form a locking feature. When the first wire 378A extends sufficiently through the loop of the second wire 378B, the closure device 200 can remain coupled to the delivery device 300 until the first wire 378A is pulled through the loop of the second wire 378B, and the second wire 378B is pulled out of the aperture 242 of the attachment member 240.

The first wire 378A and the second wire 378B can be attached at their proximal ends to the biasing member 342. In this manner, movement of the biasing member 342 in the proximal direction can cause movement of the wires 378 also in the proximal direction. In one embodiment, the wires 378 can be coupled to the biasing member 342 such that movement of the biasing member 342 will cause the first wire 378A to move a distance sufficient to be removed front the loop of second wire 378B before the second wire 378B is moved by the biasing member 342. The wire 378 can comprise a metallic wire such as NiTiNol wire. The wire 378 can also include a stainless steel wire or some other type of metal or stiff polymer. The wires 378 can be made from a material having a sufficient tensile strength to secure the closure device 200 to the tethers 364 without causing the wires 378 to fail or substantially deform. In one embodiment of the invention, the wire 378B can include a stainless steal wire and wire 378A can include a NiTiNol wire.

Other types and configurations of biasing members can be utilized without departing from the scope and spirit of the invention. For example, in one embodiment, the release assembly can include a rotating member coupled to the securing elements. In this embodiment, rotation of the rotating member can cause the securing elements to wind around the rotating member thereby causing the distal ends of the securing elements to move proximally with respect to the handle body. The closure device 200 is released from the delivery device 300 by moving a plurality of wires 378 that are housed by a tether 364 and coupled to the biasing member 342.

The method of use of the medical system 100 will now be described with reference to a particular internal tissue opening, namely a PFO. FIG. 9A illustrates the positioning of the catheter 362 through the tunnel 58 of a PFO with the first anchor 204 of the closure device 200 deployed. The medical system 100 is utilized to close an internal tissue opening by positioning the catheter 362 through an internal tissue opening and moving the first member 322 by a first movement (i.e., linearly) in the proximal direction to deploy the first anchor 204 of the closure device 200. After the first anchor 204 of the closure device 200 is deployed, the delivery device 300 can be moved in the proximal direction in order to seat the first anchor 204 against the wall of the tissue opening or otherwise engage the wall of the internal tissue opening, as illustrated in FIG. 9A. This can be done by moving the handle body 302 in the proximal direction.

Figure 10A:
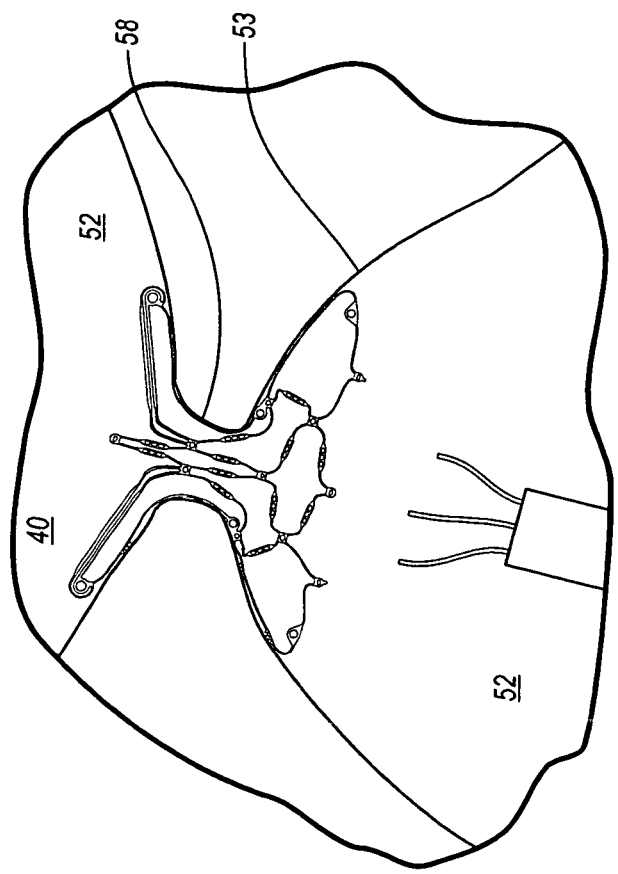
FIGS. 10A and 10B illustrate an exploded view of a delivery device according to one example.
Figure 10B:
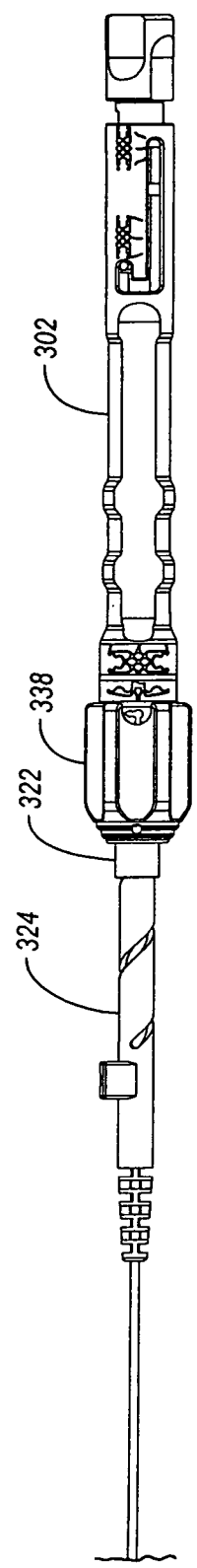
Figure 11:
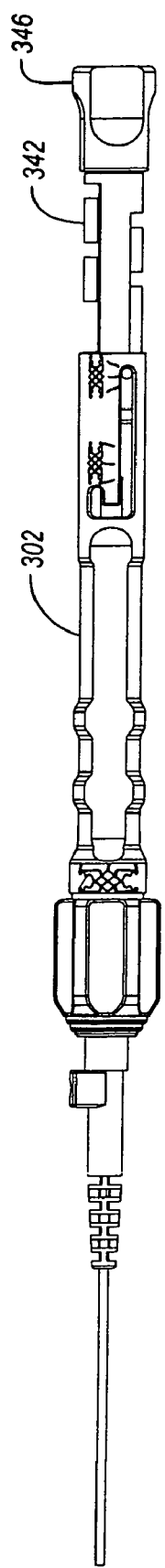
FIG. 11 illustrates the state of the delivery device upon releasing a closure device according to one example.

After the first anchor 204 has been positioned against the wall of the internal tissue opening, the knob 338, and thus the first member 322, can be moved by a second movement, or in other words, rotated to deploy additional portions of the closure device 200 as illustrated in FIG. 9B. After the closure device 200 has been fully deployed and conforms to the anatomy of the internal tissue opening, the release assembly 340 can be actuated to selectively detach the delivery device 300 from the closure device 200 as illustrated in FIGS. 10 and 11.

The release assembly 340 can be actuated by moving the biasing member 342 distally with respect to the handle body 302, then rotating the biasing member with respect to the handle body 302, and then moved proximally with respect to the handle body 302. In this manner, closure device 200 substantially conforms to the anatomy of the internal tissue opening. As noted previously, the configuration of the closure device 200 is such that when positioned in the internal tissue opening as illustrated, the members of the closure device 200 apply lateral force to the tissue of the internal tissue opening, such as the tunnel 58 of the PFO, to approximate tissue of the PFO for closure.

The delivery device 300 may be configured to deliver closure devices with additional configurations. In particular, FIGS. 12A-12N illustrate additional configurations for closure devices 200a-200n utilizing various patterns and sizes of cells, the patterns being selected to conform with typical PFO anatomy. Potential regularly sized cell structures are shown in FIGS. 12A-12N. The use of a multiple cellular structure may allow the closure elements shown in FIGS. 12A-12N to exhibit features that will increase the ability of the closure devices 200a-200n to conform to typical PFO anatomy while being collapsible within a catheter-based delivery system.

FIG. 12A depicts a closure element 200a having a five-cell design that is narrower in a middle portion 1205 than at the distal and proximal ends 1210a, 1210b, respectively. This basic design exhibits the ability to extend the cells on the distal end 1210a and cells on the proximal end 1210b outside a PFO tunnel having a relative narrow waist.

FIG. 12B illustrates a closure device 200b having a five-cell design that constrains the degree to which the device would extend into the atria of the heart while still providing wider anchoring points at the top and bottom-most cells. FIGS. 12C-12E show additional closure devices 200c-200e having varied cell configurations that include cells of different sizes. The different size cells may provide stiffness to selected areas of the structure, which in turn may result in the application of varying amounts of force to an internal tissue opening. For example, closure device 200c illustrated in FIG. 12C may provide additional stiffness at the anchoring points by providing relatively smaller cells located on or near the distal and proximal ends 1210a, 1210b. The closure device 200d illustrated in FIG. 12D may provide additional stiffness at the portion of the closure device 200d configured to be located in the tunnel, such as the middle portion 1205; therefore, smaller cells may be utilized in the middle portion 1205 as illustrated in FIG. 12D.

FIG. 12E illustrates a closure device 200e that includes a combination of the structures depicted in FIG. 12B and FIG. 12D. Other combinations of cell size and placement may be envisioned. Each of the combinations may be tailored to specific desired properties of the device. For example, FIGS. 12F-12N illustrate closure devices 200f-200n having additional cell structures that may provide adaptability to the varying needs of different PFOs of varying widths and lengths while still providing for their typical shape.

FIGS. 12O-12T illustrate closure devices 200o-200t having cell structures that have been adapted to further allow for proximal and distal anchoring and may also be adapted for varying-length PFO tunnels. FIG. 12O shows a closure device 200o having a single central cell structure with elongated arms 1220a-1220d at each corner designed to proximally and distally anchor the structure within an internal tissue opening, such as a PFO tunnel. The elongated arms 1220a-1220d may be considered as additional cells that are collapsible as the closure device 200o is collapsed within a delivery device.

In cases where the length of the single, central cell of the structure is not sufficient to completely span the length of the tunnel, the additional length of the arms may allow for the structure to be anchored with the central cell being substantially completely internal to the tunnel. FIGS. 12P and 12Q illustrate closure devices 200p and 200q in which additional central cells are added to provide additional width and length to the structure respectively. In FIGS. 12O-12Q, the elongate arms 1220a-1220d of the closure devices 200o-200q may include serrated edges. When the closure devices 200p, 200q are deployed, the serrated edges on the elongate arms 1220a-1220d may provide anchoring to the tissue.

FIGS. 12R-12T depict single-cell designs with smoother arms. These designs may provide a less aggressive anchoring to the internal tissue opening and surrounding tissues while still utilizing elongate arms 1220a-1220d, which may provide adaptability to accommodate length variations in the internal tissue openings.

FIGS. 12U-12X illustrate closure devices 200u-200x having cell structures that are similar to the cellular structures illustrated in FIGS. 12U-12X. These are examples of designs that will have adaptability to specific PFO anatomies.

The creation of cell structures that lend themselves to accommodating PFOs of varying lengths while maintaining anchoring features as well as the desired lateral force is possible and shown in FIGS. 12Y-12Z. A closure device 200y that makes use of the addition of cells with a wider aspect than taller aspect is shown in FIG. 12y. Such a configuration may create a structure that exhibits the ability to foreshorten while maintaining approximately the same width. FIG. 12Z depicts a cell structure that also has the ability to foreshorten while coupling the forces from the top and bottom of the structure by a larger amount by moving the attachment points from the middle of the structure to the edges of the waist. This provides for varying tunnel lengths while limiting the forces applied within the internal tissue opening as well as allowing the right and left anchoring features to operate more independently on one side without interference from the other side.

The structure of internal tissue openings, such as PFO anatomy, may also dictate that the right and left sides of a closure device structure have varying sizes as shown in FIGS. 13A-13C. In particular, FIG. 13A shows a closure device 200a' that includes a cell structure in which an anchor 1300a on the right (bottom) side is relatively smaller than an anchor 1300b on the left side. FIGS. 13B-13C illustrate closure devices 200b', 200c', respectively, that include anchors 1300 only on the left side or right side, respectively. Including anchors on only one side of the internal tissue opening will adapt to internal tissue opening with tapered tunnels on which it may be desirable to close only the wider side of the tunnel.

Anchoring of the PFO closure device structure within the PFO may also be done within the PFO tunnel as shown in the FIGS. 14A-14B. FIG. 14A illustrates a closure device 200d' that includes small barbs 1400 that are inclusive to the cell structure along the sides of the closure device 200d'. When deployed, the small barbs 1400 may aggressively engage the tissue and prevent migration of the closure device 200d' through the internal tissue opening. FIG. 14B illustrates separate, deployable structures 1410 that may be added to the structure of a closure device 200e' and expand into the width of the internal tissue opening when the device is deployed. In FIGS. 14A-14B it is to be understood that the anchors may be simple wire ends as shown or more aggressive, pointed or barbed features to engage the tissues associated with a tunnel of an internal tissue opening.

Various methods of construction of the closure device can be used, and as such, various materials can be used. In one configuration, a closure device may be constructed of rectangular cross-section wire that is bent to shape and joined as shown in FIGS. 15A-15B. One particular aspect ratio and bending of a single closure device element 1500 is shown FIG. 15A, and two of these components are shown connected in FIG. 15B where a row of cells 1510 is shown. Additions to this starting structure can be added to provide the desired, complete cellular structure. Starting wire may be made from metals, such as stainless steel (SS) and stainless steel alloys, tantalum, biocompatible metals, nickel titanium (NiTi), or polymer extrusions of various polymers or bioresorbable polymers. Shape memory materials such as NiTi, and shape-memory polymers could be heat-set into the bent configurations as shown in FIG. 15A.

In many cellular structures it may be desirable to keep the bending angle within the elastic limit of the starting material, to allow the structure to be collapsed within a catheter or other constraining member and to be deployed to the desired shape within the internal tissue opening. Connection of the components, shown in FIG. 15B, may be accomplished by small coils of wire held captive at the joint due to the bending of the components or with biocompatible solders or adhesives, resistance or laser welding in the case of metallic components or simply melting of polymer materials at the required junctions by application of heat directly or by ultrasonic heating. Combinations of these connection methods may be used to provide additional joint support or properties. For example, coils may be made of radiopaque material such as platinum or platinum alloys, which, in addition to providing fixation of the components, will provide for visualization by fluoroscope and X-ray.

Closure devices may also be cut from flat sheets of starting materials. By way of illustration only, cutting of the structure may be accomplished mechanically for larger cells and structures and/or by laser or photolithography for smaller structures. Cutting of these materials may be done with the device in the deployed, expanded form for materials without shape memory. For shape-memory metals, such as NiTi, the constrained shape may be cut followed by heat-setting the device to the expanded shape, which will provide for more efficient packing of the component when constrained for delivery.

Another method of creating the desired structure for the closure device is the utilization of a woven mesh of wires or polymer filaments that create a flat sheet. The cellular structure would exist as the voids between the woven wires and the structure would be collapsible for delivery through a catheter. Wire ends that extend from this construction method may be managed by tucking them back into the woven mesh, or by leaving them exposed and allowing them, when deployed in the internal tissue opening, to engage the surrounding tissues for fixation. They may also be terminated by creating interlocking loops at the edge intersections.

FIGS. 16A-16C illustrate a closure device that is configured to self-adjust according to a tunnel length of an internal tissue opening. In particular, FIG. 16A illustrates a closure device 200*f'* that includes anchoring features 1600 located on the distal end 1210*a*. The distal end 1210*a* and the proximal end 1210*b* are both illustrated as being wider than the central portion 1205, which may be a relative narrow waist portion. As previously discussed, as the closure device 200*f'* is deployed, the closure device 200*f'* expands from a compressed state within the delivery device to an expanded state in which the closure device 200*f'* becomes wider as it is deployed. In the present example, in addition to expanding from the compressed state, the length of the closure device 200*f'* is reduced to more closely approximate the length of the tunnel of the internal tissue opening. In FIG. 16A, the width of the closure device 200*f'* is in an expanded state while the overall length of the closure device 200*f'* is in an expanded state. The proximal portion 1210*b* may be configured to be reduced in length, such as through rolling.

FIG. 16A illustrates the closure device 200*f'* in a default, unconstrained state. In the unconstrained state, the proximal portion 1210*b* rolls onto itself toward the central portion 1205. As a result, the proximal portion 1210*b* shown in FIG. 16B can roll up to a PFO tunnel entry point in the right atrium and then provide an anchor that may reduce the possibility of migration of the closure device 200*f'* through the tunnel. FIG. 16C illustrates a closure device 200*g'* in which the proximal end 1210*b* of the structure comprises a coiled wire rather than coiling the entire structure. The closure devices 200*f'*, 200*g'* may be formed of metallic materials, including NiTi with its shape memory set to the configurations of FIG. 16B and/or FIG. 16C.

Yet another closure device 200*h'* is shown in FIG. 17A. A central portion 1705 of the closure device 200*h'* includes a mechanical relief point that may provide the distal and proximal ends 1210*a*, 1210*b* additional flexibility to adapt to variable anatomy of internal tissue openings. This flexibility may allow the distal end 1210*a* to rotate with respect to the proximal end 1210*b* as shown in FIG. 17B as well as allowing out-of-plane rotation.

Figure 18B:
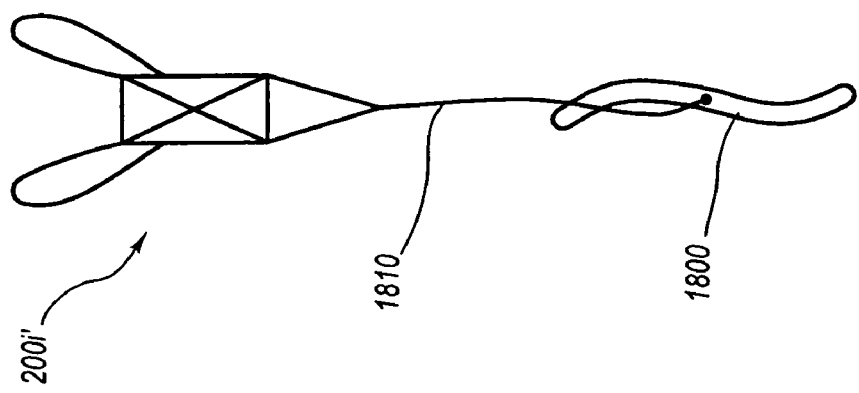
Figure 18A:
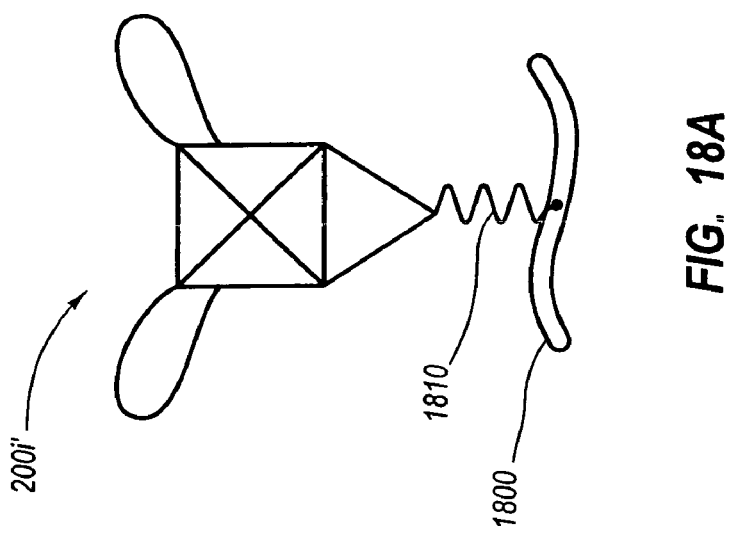

FIGS. 18A-18B illustrate closure devices 200*i'* in which a portion of the device intended to be deployed in the right atrium of the heart employs a proximal anchor 1800 that may be a rigid structural member. The proximal anchor 1800 may be attached to the rest of the closure device 200*i'* by a spring member 1810, which may allow the deployed position of the proximal anchor 1800 to vary according to the length of the PFO tunnel. Though the proximal anchor 1800 illustrated may be solid in this embodiment, it may be folded lengthwise for delivery, as shown in FIG. 18B. The solid proximal anchor 1800 may further have configurations not shown that are specifically designed to have conformance to the anatomy found on the right side of the atrial septum, including the ability to locate itself tucked under the typical arch of the septum secundum.

To this point, several examples of closure devices have been discussed. The closure devices have been discussed in the context of closure devices that expand from a compressed state to a default or decompressed state in which the expansion occurs due to the resiliency of the material used to form the closure device and/or to the shape of the closure device. Other configurations may be utilized in which the closure device is mechanically driven from the compressed to the decompressed state by forces apart from and/or in addition to spring forces associated with compression of the closure device.

FIGS. 19A and 19B are schematic diagrams of a closure element 200*j'*. The closure element 200*j'* includes expansion members 1920 with outwardly biased ends 1921, connecting members 1922, and pinned joints 1923. The connecting members 1922 are coupled to the opposing expansion members 1920 by way of the pinned joints 1923. Such a configuration allows the closure element 200*j'* to expand and collapse from a collapsed state as illustrated in FIG. 19A to an expanded state as illustrated in FIG. 19B. Further, the closure element 200*j'* may be further collapsed to fit within a delivery device.

As the closure element 200*j'* expands, the expansion members 1920 may exert a lateral force on the walls of the tunnel of an internal tissue opening in a similar manner as described above. As introduced, the expansion members 1920 include outwardly biased ends 1921. The outwardly biased ends 1921 may promote fixation of the expansion members 1920 to the internal tissue opening and/or fit the desired anatomy.

The closure element 200*j'* may be expanded by moving the central portions of the connecting members 1922 in opposing directions designated by arrows 1924. The connecting members 1922 move in opposing directions from the expansion members 1920, which are driving an outward direction, 1925. The connecting members 1922 may be locked into place by an over-center latching of the connecting members 1922 when the connecting members 1922 are forced apart from each other in directions 1924.

FIG. 19C illustrates a partial view of a connecting member 1922 in isolation. The connecting member 1922 may have engagement features 1927 at the interface of the pinned joints 1923, which will interlock at various angles allowing the separation between the expansion members 1920 to be varied. In particular, the features 1927 may include ramped tabs. FIG. 19D illustrates the interaction between connecting members 1922. The features 1927 may allow adjacent connecting members to be rotated relative to one another in one direction while preventing rotation in the opposite direction. In one example, the features 1927 may interact in a ratcheting manner.

Figure 20:
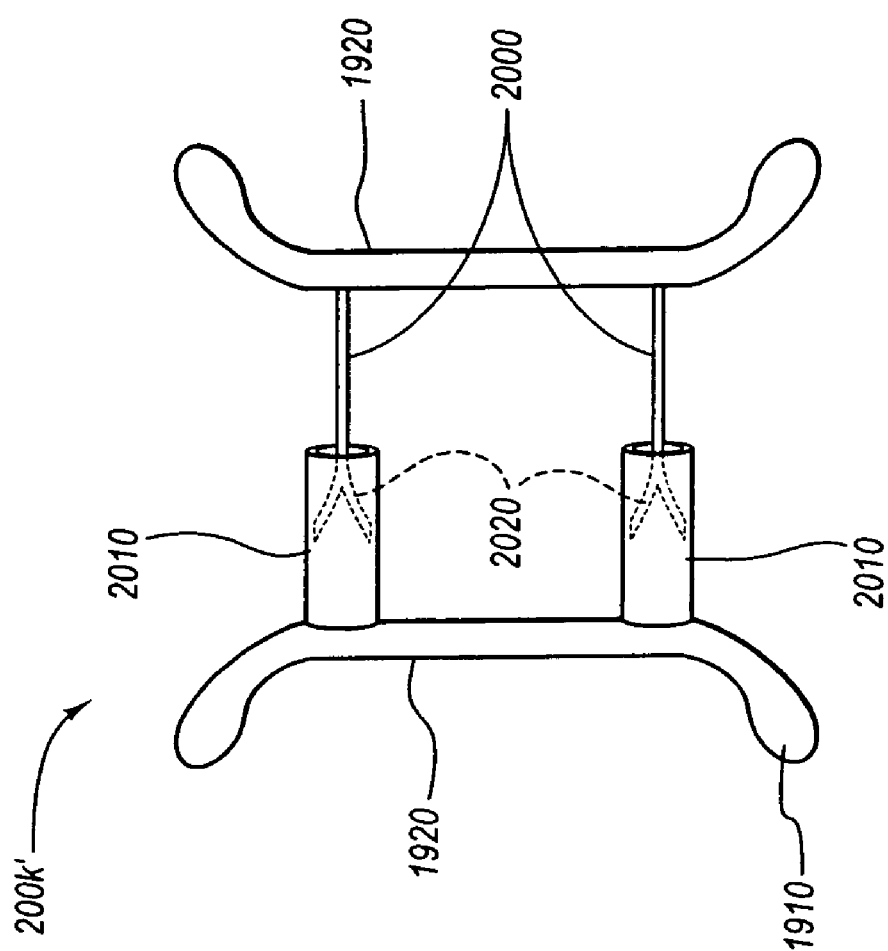

FIG. 20 illustrates a closure device 200k'. The closure device 200k' includes expansion members 1920 that are coupled together with struts 2000 positioned at least partially within tubes 2010. At the end of the struts 2000, outwardly biased biasing elements 2020 are constrained by the tubes 2010. Upon deployment of the closure device 200k', such as when the closure device 200k' is freed from a delivery device, the biasing elements 2020 allow a sliding but resist compression due to their outward bias. The outward bias of the biasing elements 2020 secure the closure device 200k' in the expanded state to secure the closure device 200k' to the walls of an internal tissue opening.

Figure 21B:
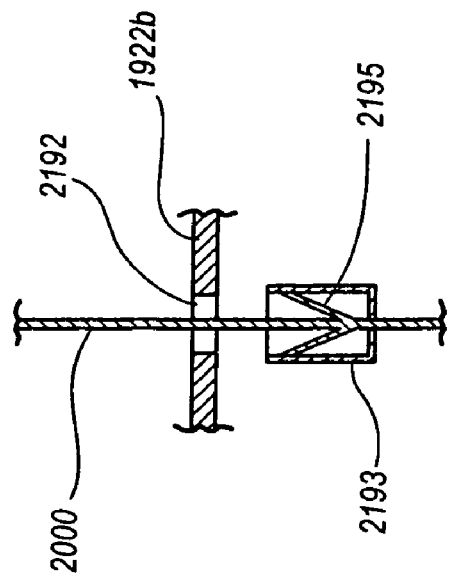
Figure 21A:
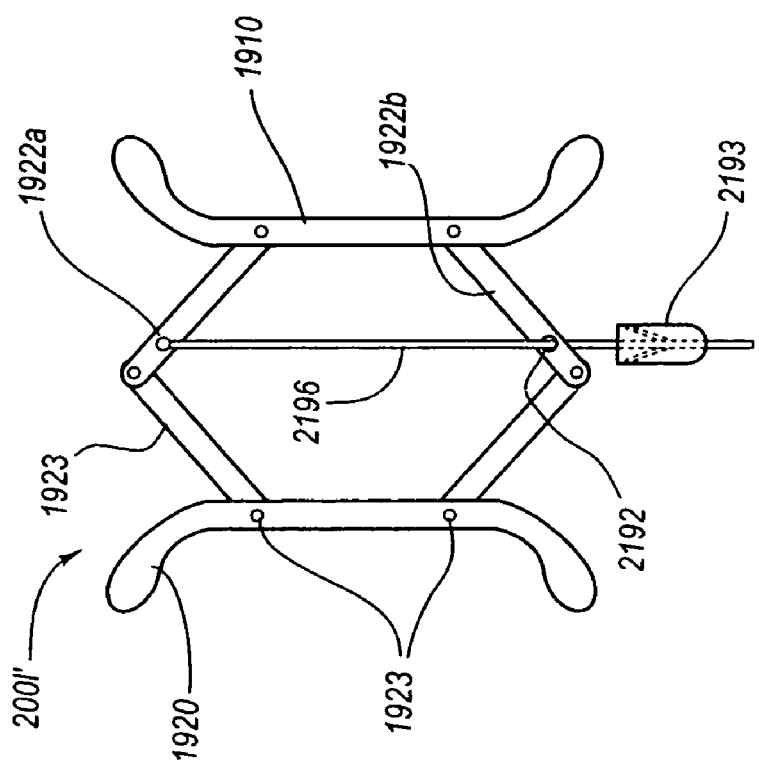

FIGS. 21A and 21B illustrate a closure device 200I' that may be mechanically deployed. The closure device 200I' with pinned joints 1923 and rigid connecting members 1923 are initially expanded along the axial direction 2198 of the structure. The expansion members 1920 are forced outward by the operation of a tether 2196 that is rigidly connected to a distal connecting member 1922a at point 2191 and extends through an opening 2192 in a proximal connecting member 1922b. Tension is maintained in the tether 2196 and a clasp 2193 is slid distally along the tether 2196 until connecting with the proximal connecting member 1922b to force the proximal connecting member 1922b proximally. As the proximal connecting member 1922b moves proximally, the proximal connecting member 1922b moves the expansion members 1920 outwardly.

FIG. 21B shows a cross-section of the clasp 2193 in relation to the opening 2192 of a proximal connecting member 1922b in which a barbed surface 2195 is configured to secure the clasp 2193 from proximal movement in relation to the tether 2196. After the clasp 2193 is cinched against the proximal connecting member 1922b, the tether 2196 is cut proximally relative to the clasp 2193 thereby releasing the closure device 200I' in its expanded position.

Figure 22B:
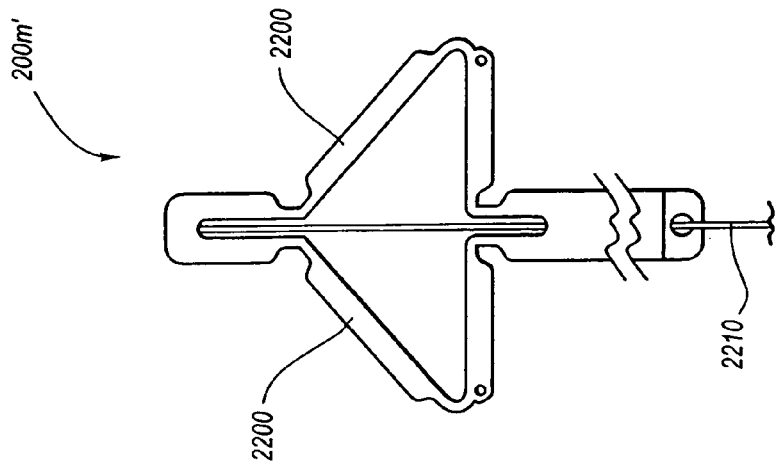
FIGS. 22A-25B illustrate delivery of closure devices using distal and/or proximal locator devices according to the present invention.
Figure 22A:
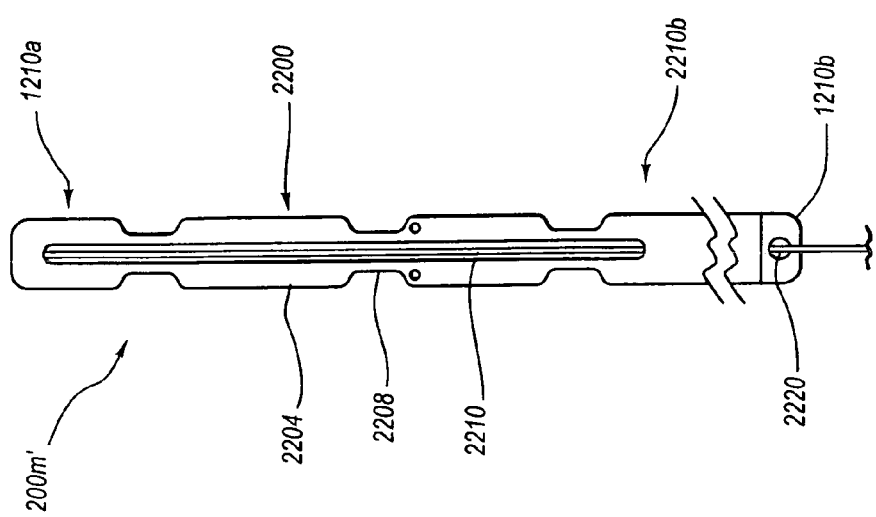

FIGS. 22A and 22B illustrate a closure device 200m' that can be deformed from an inline shape (FIG. 22A) to a "T" shape (FIG. 22b). The closure device 200m' includes anchoring arms 2200 that may be expanded to close the internal tissue opening as described above and/or to locate the system relative to the internal tissue opening. The closure device 200m' includes alternating thick portions 2204 and thin portions 2208 to form flexural hinges. The closure device 200m' further includes an actuation member 2210 that is secured to a distal end 1210a and extends from the distal end 1210a through a hole 2220 defined in the proximal end 1210b.

In order to move the closure device 200m' from the in-line position illustrated in FIG. 22A to the expanded position illustrated in FIG. 22B, the distal end 1210a is drawn toward the proximal end 1210b by drawing the actuation member 2210 toward the proximal end 1210b. As the actuation member 2210 is drawn toward the proximal end 1210b, the configuration of the closure device 200m' and of the anchoring arms 2200 in particular causes the anchoring arms 2200 to expand as illustrated in FIG. 22B.

The closure device 200m' may be made of NiTiNol, stainless steel or other material that is capable of elastic recovery from large deformations. The actuation member may be made of metal or polymeric materials with one or more strands. The flexural structure may be fabricated from tubing or from a flat sheet.

Figures 23A, 23B, 23C, 23D:
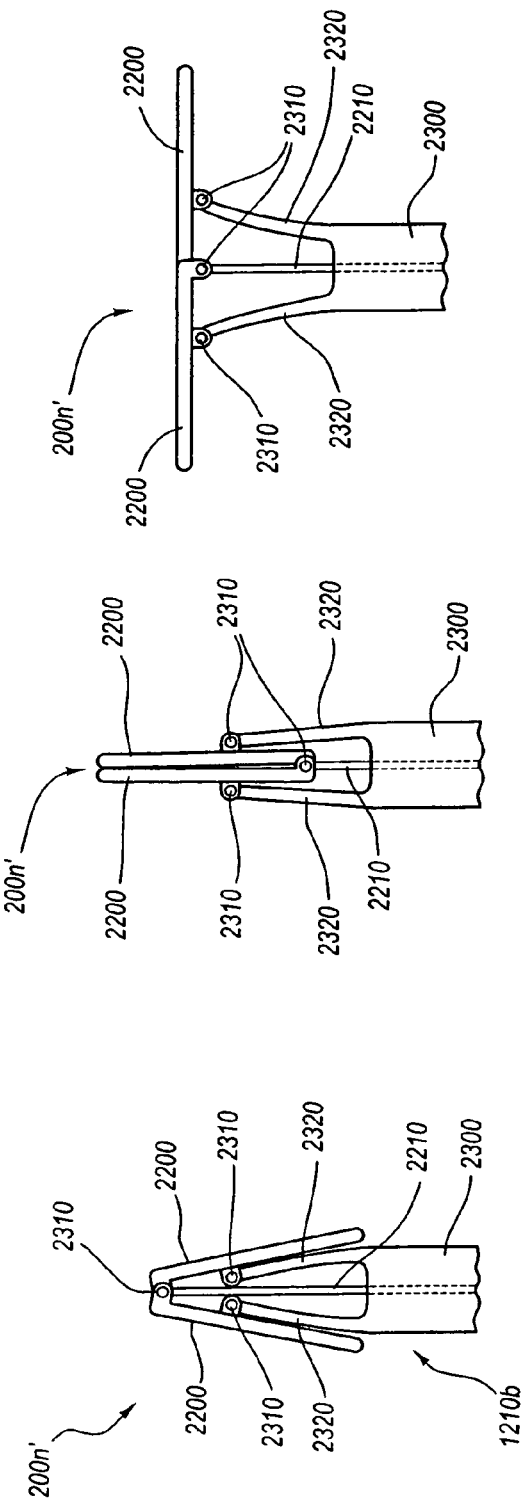

FIGS. 23A-23D illustrate a closure device 200n' that makes use of a combination of flexural hinges and pivot points. The closure device 200n' generally includes anchoring arms 2200, an actuation member 2210, and a body 2300. The anchoring arms 2200 are coupled to the actuation member 2210 by pivots 2310. Such a configuration may allow the actuation member 2210 to either pull the anchoring arms 2200 toward the proximal end 1210b to deploy the anchoring arms 2200, as illustrated in FIG. 23A, or push the anchoring arms 2200 away from the proximal end 1210b to deploy the anchoring arms 2200 as illustrated in FIG. 23B. Accordingly, the anchoring arms 2200 may be deployed by either pushing or pulling the actuation member 2210.

The body 2300 includes flexing sections 2320 by which the pivots 2310 couple the anchoring arms 2200 to the body 2300. As illustrated in FIG. 23C, as the anchoring arms 2200 are deployed, the flexing sections 2320 flex outwardly to accommodate the expansion of the anchoring arms 2200 relative to the body 2300. The body 2300 according to one example may be tubular and may be made of NiTiNol or stainless steel or other material that is capable of recovering elastically from large strains. The anchoring arms 2200 and pivots 2310 may be made from stainless steel or any other material with sufficient strength and rigidity to resist the delivery and stent opening forces. The actuation member 2210 may be made of metal or polymeric materials with one or more strands. The flexural structure may be fabricated from tubing or from a flat sheet. FIG. 23D illustrates a closure device 200o' that includes all pivots 2310 rather than a combination of pivots and flexing sections 2320.

Accordingly, closure devices 200 may be opened mechanically using a combination of actuation members, pivots, and/or flexing sections. Closure devices may also be used as part of a system with other closure devices in which one or more of the closure devices are deployed as a locator device to locate the system relative to an internal tissue opening and while additional closure devices are used to close the internal tissue opening. One such configuration will now be discussed in more detail.

Figure 24B:
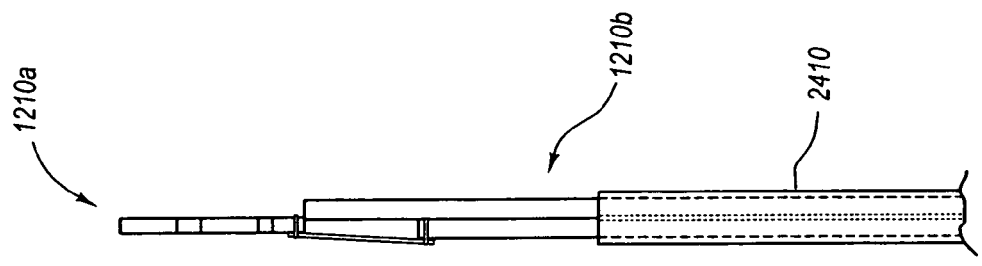
Figure 24A:
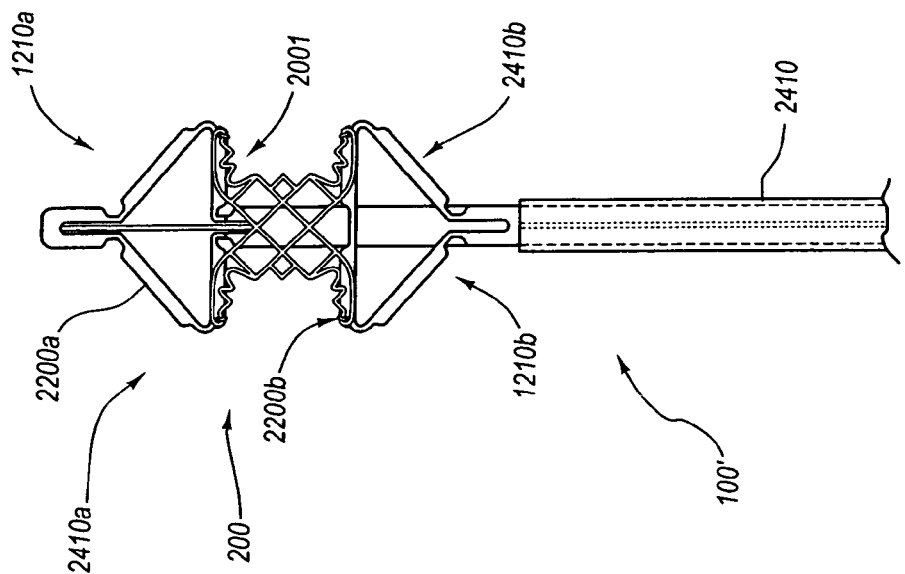

FIGS. 24A and 24B illustrate a medical system 100' configured to locate one or more closure devices relative to an internal tissue opening and to close the internal tissue opening. In the illustrated example, the most distal end 1210a of the system 100' includes a distal locator device 2400a, which may be similar in operation to closure device 200m' illustrated in FIGS. 22A-22B. The system 100' further includes a closure device 200 as well as a proximal locator device 2400b. The closure device 200 may be similar to the closure device illustrated in FIG. 5A while the proximal locator device 2400b may function in an analogous manner as the distal locator device 2400b. The distal locator device 2400a includes anchor arms 2200a. The anchor arms 2200a may be coupled to a first anchor 204. In one example, the anchor arms 2200a are coupled to the first anchor 204 by way of a distal stent compression tab 2410a. The closure device 200 is further coupled to the proximal locator device 2400b. In one example, anchor arms 2200b on the proximal locator device 2400b are coupled to a second anchor 206, such as by way of a proximal stent compression tab 2410b.

In order to deploy the distal locator device 2400a, the distal locator device 2400a may first be located beyond the distal surface of an internal tissue opening. The distal locator device 2400a may then be deployed to expand the anchor arms 2200a as well as the first anchor 204. Once the distal locator device 2400a is deployed, the system 100 may be drawn proximally to bring the closure device 200, and the first anchor 204 in particular, into contact with the tissue on the distal side of the internal tissue opening. In the case of a PFO, the first anchor 204 can be drawn into contact with the septum primum.

In one example, the proximal locator device 2400b and the second anchor 206 of the closure device 200 are then unsheathed from the delivery catheter 2410 while maintaining tension on the distal locator device 2400a. In the illustrated example, as the second anchor 206 is unsheathed, the second anchor 206 expands. While continuing to maintain tension on distal locator device 2400a, the proximal locator device 2400b is pushed toward the distal end 1210a. After the closure device 200 is deployed, the proximal locator device 2400b may be deployed to expand the anchoring arms 2200b into position against tissue on the proximal side of the internal tissue opening, such as the septum secundum in the left atrium.

The proximal locator device 2400b can then be pulled proximally to release the second anchor 206 while the proximal locator device 2400b can then be collapsed into its linear configuration. The distal locator device 2400a can then be pushed distally to release the first anchor 204. The distal locator device 2400a may then be collapsed and the entire system, less the deployed closure device 200, may be withdrawn.

Figure 25C:
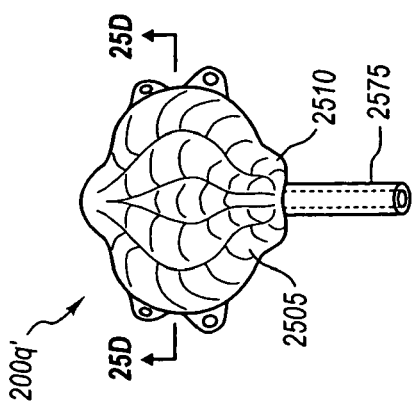
FIGS. 25C-25G illustrate inflatable closure devices according to the present invention.
Figure 25D:
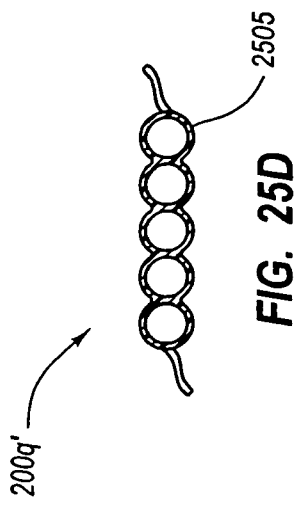
Figure 25B:
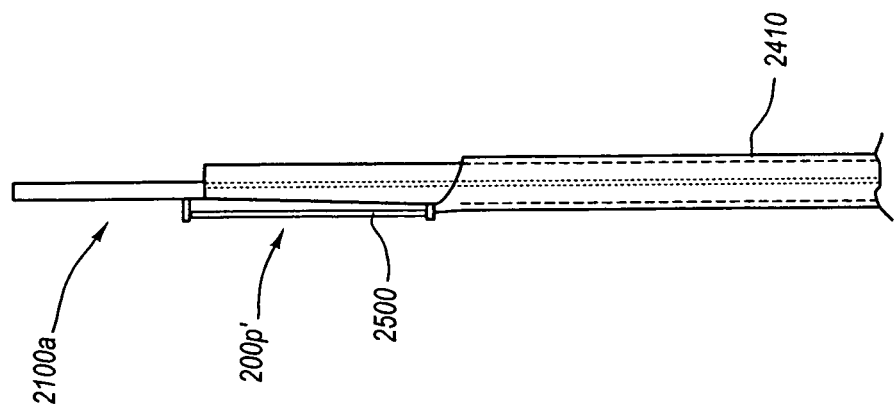
Figure 25A:
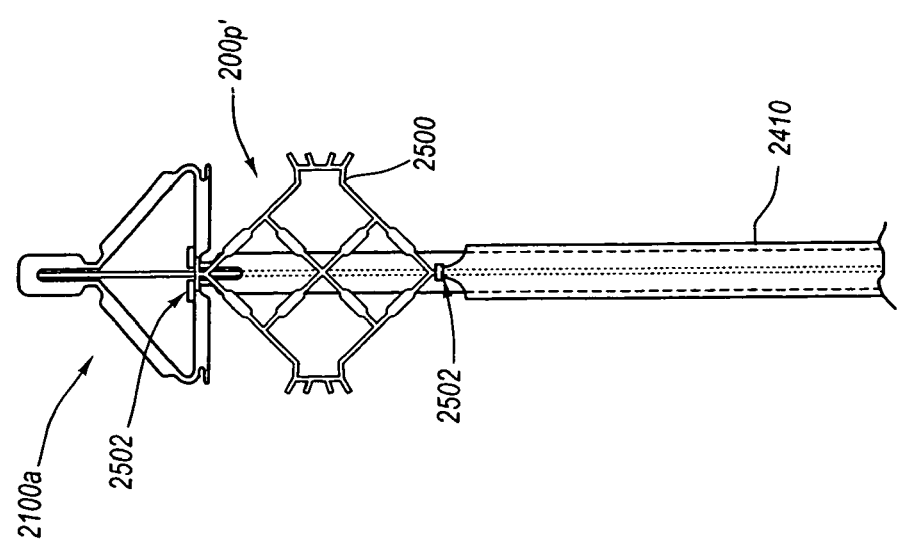
Figure 25G:
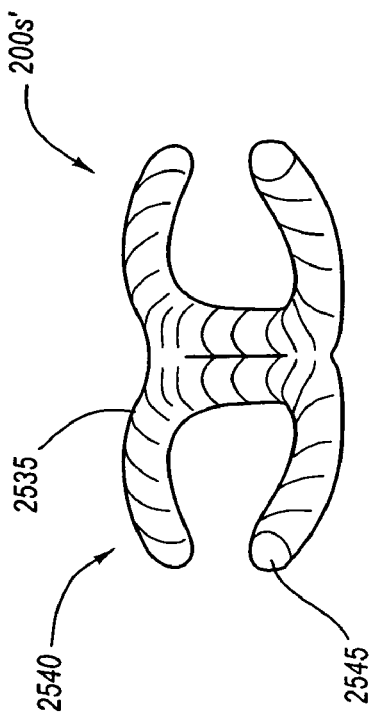

FIGS. 25A and 25B illustrate a partial view of a medical system 100" for delivering a closure device 200p' in which the closure device 200p' itself does not have proximal or distal anchoring arms. The closure device 200p' is retained by features 2500, such as laterally extending barbs that embed into the tissue of the PFO tunnel due to the lateral force that is applied by the closure device 200p'. In this case, the proximal anchor-expander has been omitted and replaced by a tab 2502 that is used to compress the closure device 200p' to deploy the closure device 200p' in the tunnel of an internal tissue opening, such as in the tunnel of a PFO. In the case of a PFO, the system 100" can be located against the septum primum at the entrance to the PFO tunnel by the distal locator device 2400a. This system 100" may be configured to reduce or eliminate the presence of anchoring arms in the atria of the heart after the closure device 200o' and the rest of the delivery system 100" has been removed.

FIGS. 25C-25F illustrate balloon-type closure devices for closing internal tissue openings. In particular, FIG. 25C illustrates a balloon-type closure device 200q' that includes a plurality of interconnected chambers 2505. FIG. 25D illustrates a view of the balloon-type closure device 200q' taken along section 25D-25D. As illustrated in FIGS. 25C and 25D, several of the interconnected chambers 2505 can be relatively long, thin chambers that are arranged in a side-by-side configuration. The interconnected chambers 2505 are in fluid communication with a manifold portion 2510. The manifold portion 2510 receives fluid from a fill port 2515. Fluid entering the manifold portion 2510 from the fill port is then distributed to the interconnected chambers 2505 to fill the interconnected chambers 2505 with fluid.

The interconnected chambers 2505 are configured to expand as they are filled with fluid in order to close an internal tissue opening. In particular, the configuration of the interconnected chambers 2505 allows the balloon-type closure device 200q' to have a relatively large lateral expansion relative to a thickness expansion as the interconnected chambers 2505 are inflated. The relatively large lateral expansion of the balloon-type closure device 200q' may exert a lateral force on the tunnel of an internal tissue opening to close the internal tissue opening as described above. Accordingly, the configuration of the interconnected chambers 2505 allows the closure device 200q' to close an internal tissue opening such as a PFO.

Figure 25E:
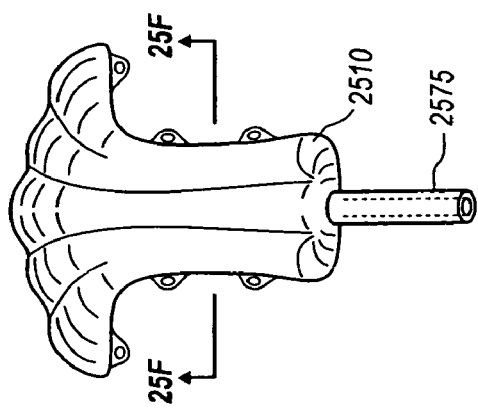

FIG. 25E illustrates a balloon-type closure device 200r' that includes flared interconnected chambers 2520. At least one of the flared interconnected chambers 2520 includes a tunnel section 2525 and a flared distal portion 2530. The flared distal portion 2530 may be configured to be expanded distally of an internal tissue opening to thereby provide a distal anchor for the closure device 200r'. Portions similar to the flared distal portion 2530 may also be provided on the proximal ends of the interconnected chambers 2520 to thereby provide proximal anchors for the closure device 200r'.

Figure 25F:
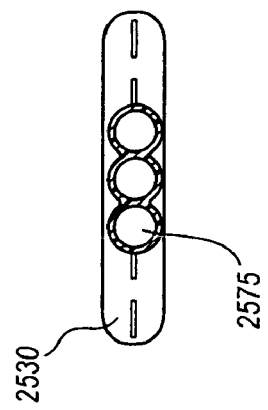

FIG. 25F illustrates a closure device 200s' that includes isolated chambers 2535. The isolated chambers 2535 form a first anchor 2540 and a second anchor 2545. The isolated chambers 2535 may be inflated in a specific sequence in order to locate and deploy the closure device 200s' in a desired manner. For example, an isolated chamber or chambers corresponding with the first anchor 2540 may be inflated first to locate the closure device 200s' in the entrance to the internal tissue opening. In the case of a PFO, the first anchor 2540 may be inflated in the left atrium. A central chamber may be inflated next to expand the central portion 2550 of the closure device 200s' to close the tunnel of the internal tissue opening. A proximal chamber may then be inflated to expand the second anchor 2545. Any of the balloon-type closure device configurations described above and otherwise may be formed of a resorbable or non-resorbable biocompatible material. Such a configuration may allow a practitioner to leave the inflated balloon in the PFO as an occlusive implant. While specific configurations are illustrated, balloon-type closure devices may be utilized that include any number of chambers that may include any combination of isolated and interconnected chambers that may be inflated in any number of stages.

In several examples, after the closure device has been deployed, the closure device is released from the rest of the system by a release mechanism. Accordingly, several release mechanisms may be provided to release the closure devices from locator devices and/or delivery devices once the closure device has been deployed to close an internal tissue opening such as a PFO. For example, the systems 100', 100" illustrated in FIGS. 24A-24B and 25A-25B, respectively, may make use of a post-in-hole configuration of connecting the closure devices 200 and 200o' to the medical system 100', 100". Other configurations may be utilized to selectively release the closure device from the delivery system. Generalized attachment points will be illustrated and described for closure devices as well as generalized delivery points for the delivery devices. It will be understood that the various configurations illustrated and described below may be adapted to use with any number of delivery devices in combination with any number of closure devices.

FIGS. 26A-26E illustrate several release mechanisms 2600a-2600e for releasing a closure device 90 from a delivery device 92. In particular, closure devices 90 may include an attachment member 240a-240e that couples the closure device 90 to a portion of the delivery device 92. For ease of reference, push members 96a-96e will be described as the portion of the delivery device to which the attachment member 240 is selectively secured. For example, FIG. 26A illustrates a release mechanism 2600a in which the attachment member 240a includes a post 2602 formed on the closure device 90 that engages a hole 2605 formed in the corresponding portion of the push member 96a. The attachment member 240a, and thus the associated closure device 90, is retained by the push member 96a as long as the attachment member 240a remains under compression by the push member 96a. When the compression is released, the post 2602 may slide out of the hole 2605 in the corresponding portion of the attachment member 240a.

FIG. 26B illustrates release mechanism 2600b that includes an attachment member 240b and push member 96b for retaining and selectively releasing a closure device 90b from a delivery device. The release mechanism 2600b illustrated includes a flexible loop 2610 attached to the push member 96b. The loop 2610 extends through a hole 2615 formed in the attachment member 240b. The loop 2610 is retained in position by release wire 2620. To release the closure device 90b, the release wire 2620 is pulled out of the tether loop 2610. Releasing the loop 2610 allows the closure device 90b to be released by sliding away the loop 2610 from the delivery device 300.

FIG. 26C shows a release mechanism 2600c that makes use of an attachment member 240c that includes a tab 2622. The tab 2622 is configured to engage a push member 96c. In particular, the tab 2622 may have a dog-leg shape that is configured to extend into a slot 2624 formed in the push member 96c. A release wire 2625 extends into the push member 96c and maintains the tab 2622 in engagement with the slot 2624 as illustrated. When the release wire 2625 is pulled proximally, the release wire 2625 is withdrawn from engagement with the tab 2622. As tab 2622 is released from the tab 2615, the tab 2622 is then freed from the slot 2620 and the push member 96c may then be withdrawn from the attachment member 240c to thereby release the closure device 90c.

FIG. 26D illustrates a release mechanism 2600d that includes an attachment member 240d and push member 96d configuration that includes flexible filament 2630. The flexible filament 2630 extends through a cross-hole 2635 formed in the push member 96d, distally through a hole 2640 in the attachment member 240d, and back into the push member 96d as illustrated. A cutting slug 2645 is also operatively associated with the push member 96d. The cutting slug 2645 is configured to be moved distally past the cross-hole 2635 to thereby cut flexible filament 2630. When the flexible filament 2630 is cut, the attachment member 240d is thereby freed from the push member 96d.

FIG. 26E illustrates a release mechanism 2600e that has an attachment member 240e that is retained within a push member 96e by nesting tabs 2650, 2655. Nesting tab 2650 may be part of the attachment member 240e while nesting tab 2655 may be operatively associated with the push member 96e. While the nesting tabs 2650, 2655 remain engaged and disposed within the push member 96e, the attachment member 240e remains coupled to the push member 96e. In order to release the attachment member 240e, the nesting tabs 2650, 2655 are moved distally relative to the push member 96e. Once the nesting tabs 2650, 2655 are outside of the push member 96e, the nesting tabs 2650, 2655 are allowed to separate to thereby release the attachment member 240e from the push member 96e.

In one example depicted in FIG. 27A, a release mechanism 2600f includes a push member 96f that is formed of a meltable material, such as, but not limited to, a polymer filament made from either a single polymer fiber or a bundle or braid of multiple fibers. The push member 96f may be secured to an attachment member 240f. In this illustrated embodiment, the push member 96f can be passed through a coil 2700 of electrically conductive wire. The coil 2700 can be attached to a current source through less resistive leads 2705.

When a current is passed through the coil 2700, the resistivity of the coil heats the push member 96f until the push member 96f melts, thereby severing the push member 96f proximally from the attachment member 240f. As the push member 96f is severed, the attachment member 240f and thus the closure device associated with the push member 96f are released. The current source 2705 may be configured to provide a direct current to perform the resistive heating of the coil 2700. It may also be desirable for the current source 2705 to provide alternating current with the alternating current ranging up to radio frequencies. The coil 2700 may also be covered with an optional insulating layer 2710. The inclusion of an insulating layer 2710 may aid with transfer of heat from the coil 2700 as it is heated to the surrounding tissues or fluids.

In another example, a release mechanism 2600f including the resistive coil 2700 forms a resistive temperature device (RTD) that provides feedback with respect to the temperature of the push member 96f while a current is applied to the coil 2700. The coil 2700 in this case may be made of a metal that exhibits a relatively large change in resistance as it is heated such as, but not limited to, nickel, copper, or platinum. The actual temperature of the push member 96f may be monitored at intervals during heating by removal of the heating current, and then applying a known voltage through the delivery mechanism 2600f, which may include the coil 2700. The resulting resistance measurement may then be proportional to the temperature of the coil as with a conventional RTD.

FIG. 27B is a schematic diagram of a release mechanism 2600g that includes a bimetallic actuator 2720. The bimetallic actuator 2720 may be configured to provide for mechanical detachment of a closure device (not shown) from a delivery device at a specified temperature or temperature range. The bimetallic actuator 2720 includes a coiled, bimetallic strip 2725 that can be connected to a securing member 2730, which couples an attachment member 240g to a push member 96g. As a result, the securing member 2730 allows the push member 96g to drive the attachment member 240g when the securing member 2730 is in place. More specifically, the securing member 2730 engages both the attachment member 240g and the push member 96g such that movement of the push member 96g is transferred from the push member 96g to the securing member 2730 and thence to the attachment member 240g.

The bimetallic strip 2725 is configured to uncoil at elevated temperatures. As the bimetallic strip 2725 uncoils, the securing member 2730 is drawn from its connection to the push member 96g. After the securing member 2730 is drawn from engagement with the attachment member 240g, the attachment member 240g may move freely and thus be released from the release mechanism 2600g. Further movement of the bimetallic strip 2725 may release the push member 96g, which may then be withdrawn proximally as desired.

FIG. 27C is a schematic diagram of a release mechanism 2600h that includes a bimetallic coil 2725. The bimetallic coil 2725 is coupled to a lever arm 2735, which in turn is coupled to a securing member 2730. The lever arm 2735 rotates about a pivot point 2740. As the bimetallic coil 2725 unwinds, such as in response to an increase in temperature, the bimetallic coil 2725 drives the lever arm 2735. The lever arm 2735 includes a relatively short portion 2745a proximate to the bimetallic coil 2725 and a relatively long portion 2745b proximate the securing member 2730. Such a configuration may amplify the amount of movement that is realized by the uncoiling of bimetallic coil 2725. As a result, relatively small increases in temperature may be used to move the securing member 2730 from engagement with the attachment member 240g and then the push member 96g. Additional configurations of bimetallic release mechanisms may be adapted to be compatible with the geometry of various specific closure devices.

Release mechanisms and assemblies may also make use of shape memory actuators to release a closure device. Certain shape memory alloys, such as NiTiNol, have the ability to transition from a first shape to a pre-set shape above a certain temperature that is dictated by the constituents of the alloy. FIGS. 27D-27G illustrate release mechanisms 2600i-2600j that may make use of shape memory materials. In FIG. 27D, the release mechanism 2600i includes a shape memory actuator 2750. The shape memory actuator 2750 is secured to a closure device 90. In particular, a first portion 2750a of the shape memory actuator 2750 is secured to an attachment member 240i of the closure device 90. The closure device 90 further has a recess 2755 defined therein opposite the attachment member 240i. The shape memory actuator 2750 extends from the attachment member 240i through a push member 96i and into engagement with the recess 2755.

In particular, the shape memory actuator 2750 extends through a loop 2757 in the push member 96i while in the secured position. Illustrated in FIG. 27D, a second portion 2750b of the shape memory actuator 2750 extends into the recess 2755 to retain the push member 96i to the closure device 90. The recess 2755 may also be made by forming a wire loop or other securing point for the shape memory actuator 2750. The shape memory actuator 2750 may also have a shape that will adapt to be secured within the recess 2755. While a pin and loop configuration is described in this and other examples, other pin and receiving member configurations may also be utilized to retain a closure device until the closure device is selectively released.

FIG. 27E depicts the release of the push member 96i by heating the shape memory actuator 2750. More specifically, as the shape memory actuator 2750 is heated to a temperature above the transition temperature of the shape memory material, the shape memory actuator 2750 may then recover to the preset shape illustrated in FIG. 27E. The preset shape of the shape memory actuator 2750 may be a coiled configuration such that the shape memory actuator 2750 may be drawn toward the attachment member 240i to release the push member 96i. As the push member 96i is released, the closure device 90 is free to move relative to the push member 96i and is thereby released as well.

FIGS. 27F and 27G are schematic views of a release mechanism 2600j that includes a plurality of shape memory actuators 2750a, 2750b. As illustrated in FIG. 27F, the shape memory actuators 2750a, 2750b may extend in opposing directions from opposing portions of a closure device 90 while the shape memory actuators 2750a, 2750b remain below the transition temperatures of the shape memory materials of which the shape memory actuators 2750a, 2750b are formed. In such a configuration, at least a portion of each of the shape memory actuators 2750a, 2750b extend through a loop 2757 formed in a push member 96j.

FIG. 27G illustrates the shape memory actuators 2750a, 2750b that have been heated to a temperature above the transition temperature of the shape memory material. As the shape memory actuators 2750a, 2750b are heated above the transition temperature of the shape memory material, the shape memory actuators 2750a, 2750b return to their preset states, which may be the coiled configurations illustrated in FIG. 27G. As the shape memory actuators 2750a, 2750b return to their preset states, the shape memory actuators 2750a, 2750b are removed from their securing positions relative to a loop 2757 in the push member 96j to release the push member 96j as shown in FIG. 27G. The heat input for heating shape memory actuators 2750, 2750a, 2750b may be provided by external exposure to elevated temperatures, radio frequency heating or applying an electrical current through the actuator member.

In another example (not shown), multiple shape memory securing members may be made to release the push member. In another embodiment (not shown), these multiple shape memory securing members may have actuators that transition at different temperatures that can allow for one part of the device to be released at one temperature and another portion of the device to be released at a second temperature. In another embodiment (not shown), the push member or push members may be comprised of a conductive material and an electrical connection to the implant may also be severed during the release of the push member. Combinations of the above embodiments may be utilized to provide both the desired mechanical detachment from the implant as well as to cause the actuation to occur at a pre-defined temperature or temperatures.

In some examples, the push member may include a central portion that includes one or more filaments, such as a polymer filament, or a bundle of filaments or braid. Polymers may include, without limitation, nylons, Dacron, polyester, polyethylene, Teflon, PTFE, Kevlar, Spectra or the like. These materials may also be components of a larger push member system that extends to the proximal, operable end of the device and consist of a polymer catheter or metallic hypotube of stainless steel or other biocompatible alloys.

FIGS. 27H and 27I illustrate a release mechanism 2600k that includes a cutting feature 2760. The cutting feature 2760 is coupled to a shape memory actuator 2750c. The shape memory actuator 2750c in turn s secured to a first portion 2765 of a closure device 90. A push member 96k is secured to a second portion 2770 of the closure device 90. The push member 96k extends away from the second portion 2770 and through an opening 2772 formed in the cutting feature 2760 while the shape memory actuator 2750c remains below the transition temperature and thus in an initial position.

As the shape memory actuator 2750c is heated above the transition temperature, the shape memory actuator 2750c moves to the preset shape illustrated in FIG. 27I. Accordingly, the shape memory actuator 2750c is drawn toward the first portion 2765 of the closure device 90. Drawing the shape memory actuator 2750c toward the first portion 2765 of the closure device also draws the cutting feature 2760 in the same direction, which causes the cutting feature 2760 to sever the push member 96k. The closure device 90 is thereby released from the push member 96k.

Figure 27K:
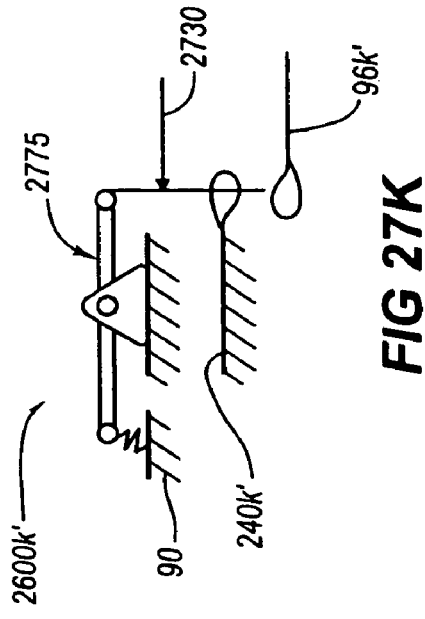
Figure 27J:
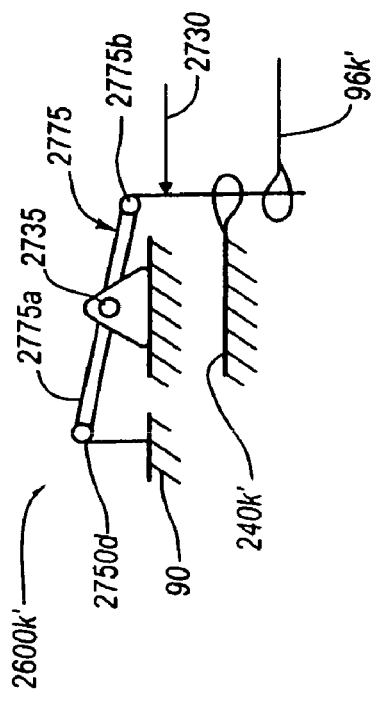

The properties of shape memory alloys may also be used to actuate the release of a securing member 2730 as illustrated in the release mechanism 2600k' in FIGS. 27J and 27K. In particular, a shape memory actuator 2750d is secured to a closure device 90, which is depicted as ground. A linkage 2775 is coupled at a first end 2775a to the shape memory actuator 2750d and at a second end 2775b to the securing member 2730. The linkage 2775 is configured to rotate about a pivot 2735, the pivot 2735 being secured to the closure device 90. In particular, the linkage 2775 is configured to rotate in response to movement of the shape memory actuator 2750*d* such that movement of the shape memory actuator 2750*d* is transferred by the linkage to the securing member 2730.

While the securing member 2730 engages both the attachment member 240*k'* and the push member 96*k'* such that movement of the push member 96*k'* is transferred from the push member 96*k'* to the securing member 2730 and thence to the attachment member 240*k'*. Accordingly, while the shape memory actuator 2750*d* remains at a temperature below the transition temperature of the shape memory material, the shape memory actuator 2750*d* remains extended and the securing member 2730 remains in engagement with the attachment member 240*k'* and the push member 96*k'*.

FIG. 27K illustrates the shape memory actuator 2750*d* returning to a preset state that corresponds to the shape memory material of the shape memory actuator 2750*d* being heated to a temperature above the transition temperature. As illustrated in FIG. 27K, as the shape memory actuator 2750*d* returns to its preset state, the first end 2775*a* is drawn toward the closure device 90 thereby drawing the securing member 2730 first from engagement with the push member 96*k'* and then engagement with the attachment member 240*k'*. As a result, heating the shape memory actuator 2750*d* releases the closure device 90 from the push member 96*k'*.

Figure 27M:
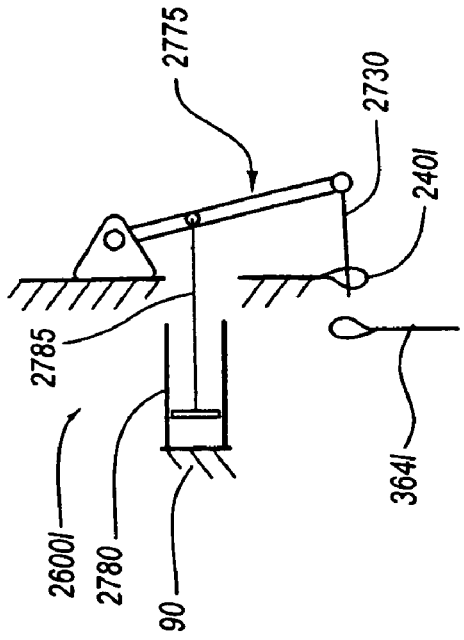
Figure 27L:
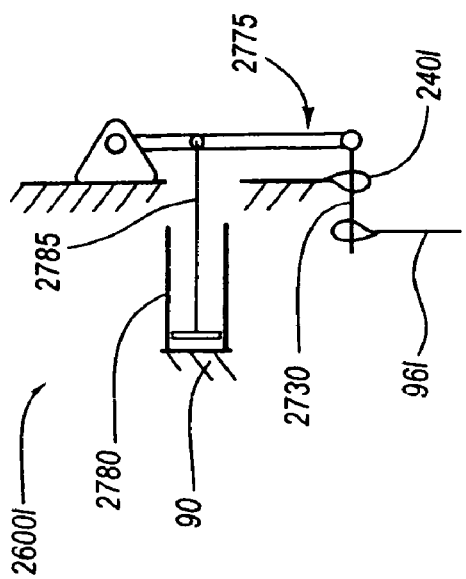

A phase change of a material in an enclosed space may also provide for the actuation of a release mechanism 2650*l*, as shown in FIGS. 27L and 27M. FIG. 27L depicts cylinder 2780 and piston 2785 attached to a closure device 90. The cylinder 2780 and piston 2785 are operatively associated with a linkage 2775 that is coupled to a securing member 2730. The securing member 2730 secures the push member 96*l* to an attachment member 240*l*, the attachment member 240*l* being part of the closure device 90.

Heating the material within the cylinder 2780 generates pressure that drives the piston 2785 away from the cylinder 2780. As the piston 2785 is driven away from the cylinder 2780, the piston 2780 drives the linkage 2775 and thus the securing member 2730. As the securing member 2730 is thus driven, the push member 96*l* is released from the closure device 90.

Other examples of release mechanisms (not shown) that make use of phase change include the removal of the linkage 2775 shown in FIGS. 27 L and 27M and making a direct connection between the securing member 2730 and the piston 2785. Another embodiment of the system (not shown) replaces the cylinder and piston 2780, 2785 with a bellows assembly that also provides a sealed container for the phase-change material that can expand axially when the phase change occurs. Phase change materials that may be utilized in this system for expansion upon heating may include, without limitation, various hydro-carbon fluids such as heptane, isopropyl alcohol and the like. Formulations of waxes such as those used in the thermostats of common automotive engine thermostats may also be utilized.

In some of the examples, portions of the release mechanism, such as the shape memory actuators, are attached to the closure device. Such attachment may be switched and/or altered as desired. In other examples (not shown), shape memory actuators may be attached to the push member. In still other examples (not shown), shape memory actuators may be attached in combination to the closure device and the push member. In yet other examples (not shown), shape memory actuators may be attached to other portions of the medical system.

Reference to FIGS. 28-38B will now be made to describe a delivery device 2800 that can be used to deploy a closure device 90. Furthermore, the method of using delivery device 2800 will also be described. In the illustrated configuration, delivery device 2800 can include a main handle 2802, a guide catheter 2818 coupled to and extending distally from main handle 2802, a pusher handle 2820 coupled to main handle 2802, a release knob 2826 coupled to pusher handle 2820 and an end cap 2832. Main handle 2802 can have an elongated cylindrical shape and can be substantially hollow. Main handle 2802 can be configured to assist a user in placing closure device 90.

Figure 29:
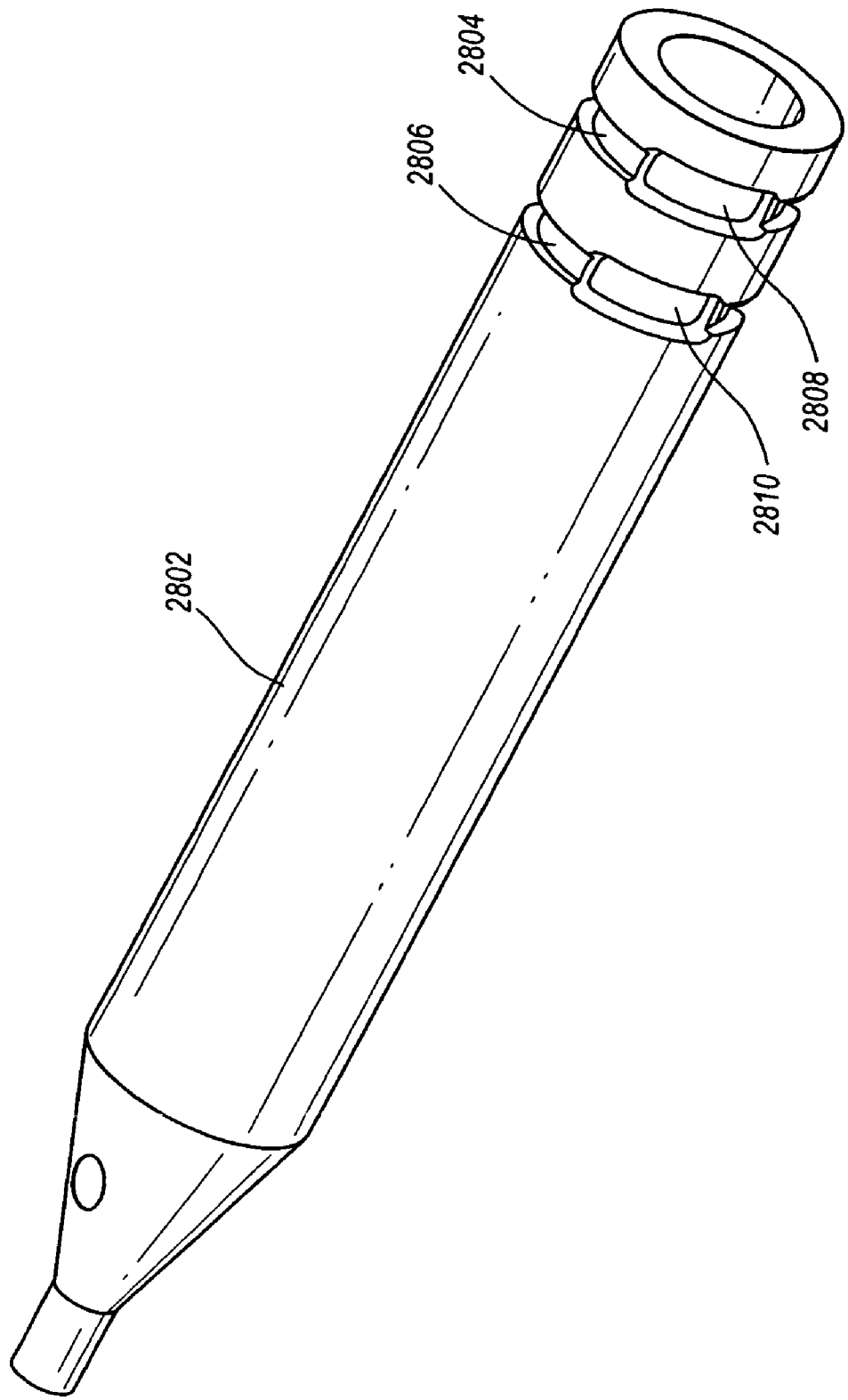

In fluid communication with a portion or the main handle 2802 can be a flush line 2816, while selectively movable relative to the main handle 2802 can be first and second stops 2812, 2814. Flush line 2816 can be configured to be in fluid communication with guide catheter 2818. First stop 2812 can be configured to be received in a first groove 2804 (FIG. 29) and second stop 2814 can be configured to be received and at least partially movable in a second groove 2806 (FIG. 29). First groove 2804 can extend radially along the circumference of main handle 2802. First groove 2804 can be configured to receive first stop 2812 therein and allow first stop 2812 to at least partially rotate therein. First groove 2804 can include a first opening 2808. First opening 2808 can extend through the wall of main handle 2802. First opening 2808 can be configured to receive a set screw (not shown) positioned a hole disposed through first stop 2812. This hole enables the set screw to be received within first opening 2808 and can limit rotational movement of first stop 2812 relative to main handle 2802. It will be understood that a portion of the first stop 2812, instead of or in addition to the set screw, can extend into first opening 2808.

Similarly, second groove 2806 can extend radially along the circumference of main handle 2802. Second groove 2806 can be configured to receive second stop 2814 therein and allow second stop 2814 to at least partially rotate therein. Second groove 2806 can include a second opening 2810. Second opening 2810 can extend through the wall of main handle 2802. Second opening 2810 can be configured to receive a set screw (not shown) positioned in a hole disposed through second stop 2814. This hole enables the set screw to be received within second opening 2810 and can limit rotational movement of second stop 2814 relative to main handle 2802. It will be understood that a portion of the second stop 2814, instead of or in addition to the set screw, can extend into second opening 2810.

First stop 2812 can be received in first groove 2804 and can at least partially rotate circumferentially in first groove 2804. At least a portion of first stop 2812, or the set screw passing through the first stop 2812, can extend in and through first opening 2808. First stop 2812 can be configured to enable selective deployment of PFO closure device 3000, as will be discussed more fully hereinbelow. Similarly, second stop 2814 can be received in second groove 2806 and can at least partially rotate circumferentially in second groove 2806. At least a portion of second stop 2814, or the set screw passing through the second stop 2814, can extend in and through second opening 2810. Second stop 2814 can be configured to enable selective deployment of PFO closure device 3000, as will be discussed more fully hereinbelow. The distance between first and second stops 2812 and 2814 can correspond to the distance sufficient to expose and deploy distal anchors 3006 from guide catheter 2818 as pusher handle 2820 moves with respect to main handle 2802 in the distal direction while maintaining proximal anchors 3008 within guide catheter 2818.

PFO closure device 3000 can be inserted into the distal end of a guide catheter 2818 in a manner such that proximal anchors 3008 extend proximally and distal anchors 3006 extend distally within guide catheter 2818. PFO closure device 3000 can be attached to delivery device 2800 through use of tabs 3012.

Figure 31:
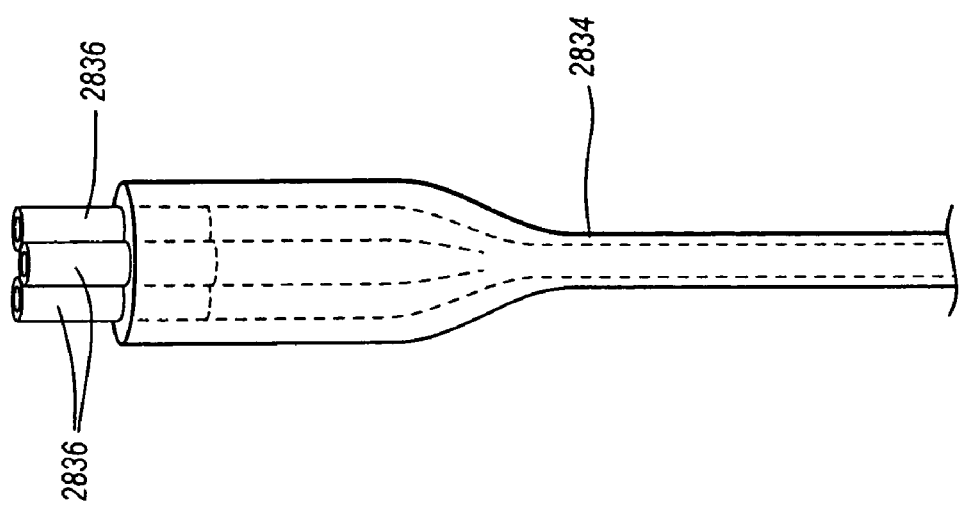

Delivery device 2800 can further include a pusher tube 2834 (FIG. 31). Pusher tube 2834 can be received and movable in guide catheter 2818 (FIG. 28) and can substantially extend from the distal end of guide catheter 2818 to pusher handle 2820. Pusher tube 2834 can be coupled to pusher handle 2820, such that movement of pusher handle 2820 relative to main handle 2802 can result in movement of PFO closure device 3000 out of the distal end of catheter shaft.

Figure 30C:
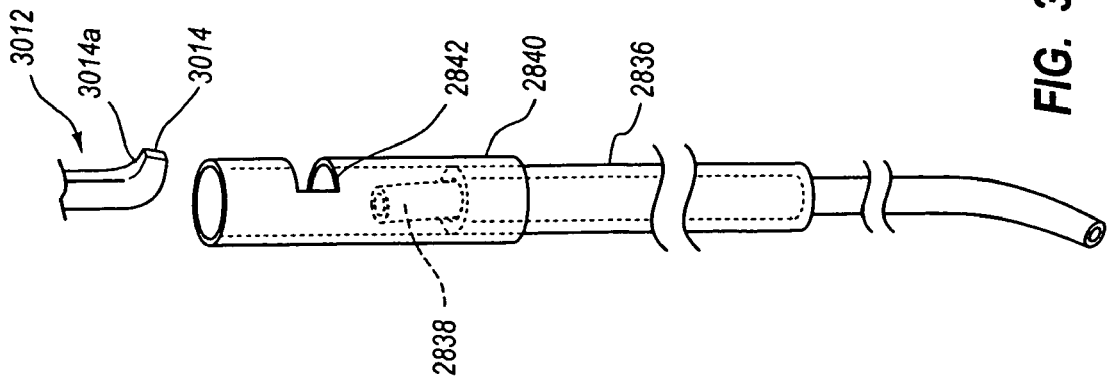
Figure 30B:
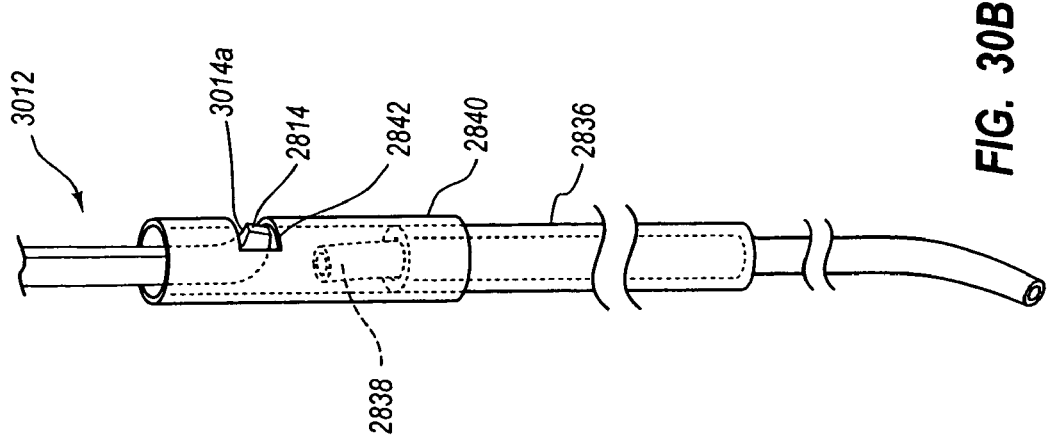
Figure 30A:
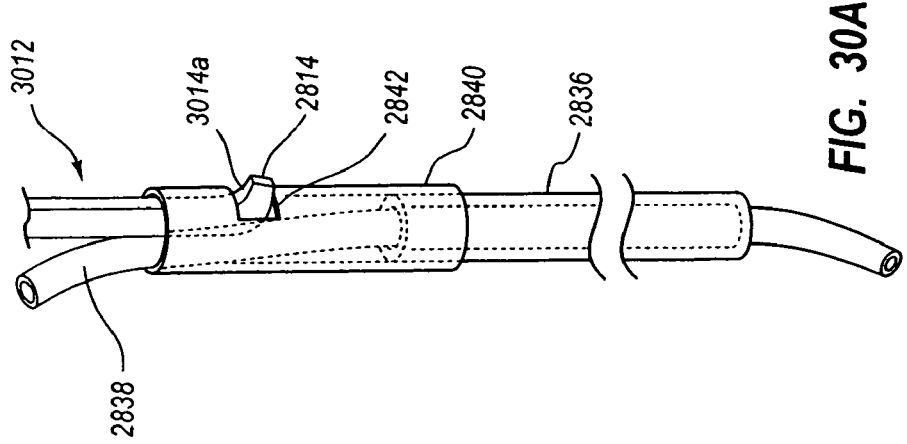

In the illustrated embodiment, delivery device 2800 can include one or more flexible tubes 2836 (FIGS. 30A-31). The number of flexible tubes 2836 can optionally correspond with the number of tabs 3012 of PFO closure device 90. In one configuration, flexible tube 2836 can be coupled to pusher tube 2834 such that movement of pusher tube 2834 can result in movement of flexible tube 2836. Generally, pusher tube 2834 can receive various wires, tubes, etc., of delivery device 2800 and the aid with deploying device 3000. For instance, pusher tube 2834 can receive a thermocouple, a tubular member receiving the thermocouple and associated electrically communicating wire(s), RF energy delivery and return wire (s) or conductor(s), or the like.

As shown in FIG. 31, one flexible tube 2836 is spaced apart from two adjacently positioned flexible tubes 2836. The resultant gap can receive a portion of the wires, tubes, etc., received by the pusher tube 2834. For instance, and not by way of limitation, the thermocouple, the tubular member receiving the thermocouple and associated electrically communicating wire(s), the RF energy delivery and return wire(s) or conductor(s), or the like, can exit from the pusher tube 2834 and pass to the closure device 3000.

To aid with such movement, each flexible tube 2836 can include a tube cap 2840, as illustrated in FIGS. 30A-30C. Tube cap 2840 can be sized and configured to receive tab 3012 therein. Tube cap 2840 can include a slot 2842 sized and configured to receive a foot 3014 of tab 3012 therein. The size and configuration of tube cap 2840 can be such that when foot 3014 of tab 3012 is in slot 2842, a detachment wire 2838 can extend through and out of the distal end of tube cap 2840. In this manner, detachment wire 2838 can serve to bias and substantially hold tab 3012 in tube cap 2840 and thus substantially prevent detachment of PFO closure device 3000 from delivery device 2800 until detachment wire 2838 is moved away from foot 3014, as will be described hereinbelow. FIGS. 30A-30C illustrate a single flexible tube 2836 as detachment wire 2838 is sequentially moved proximally to enable foot 3014 to be removed from tube cap 2840.

Guide catheter 2818 can be coupled to main handle 2802. Guide catheter 2818 can be configured to house at least a portion of pusher tube 2834 and other portions of the delivery device 2800 therein. Guide catheter 2818 can further be configured to allow pusher tube 2834 to rotate and translate therein. The distal end of guide catheter 2818 can be configured to receive PFO closure device 3000 therein.

Figure 28:
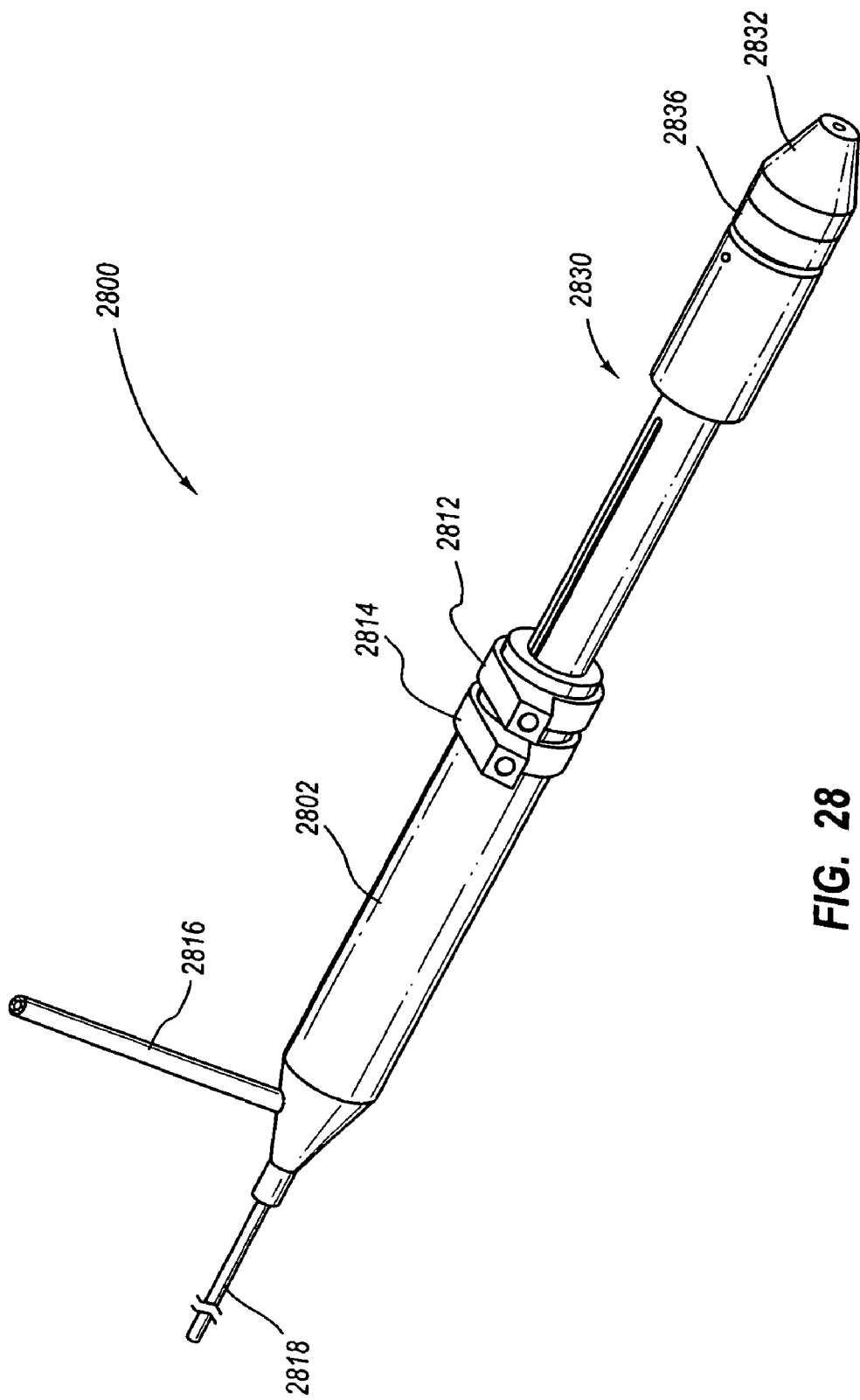
FIGS. 28-38B illustrate a delivery device according to the present invention.
Figure 32:
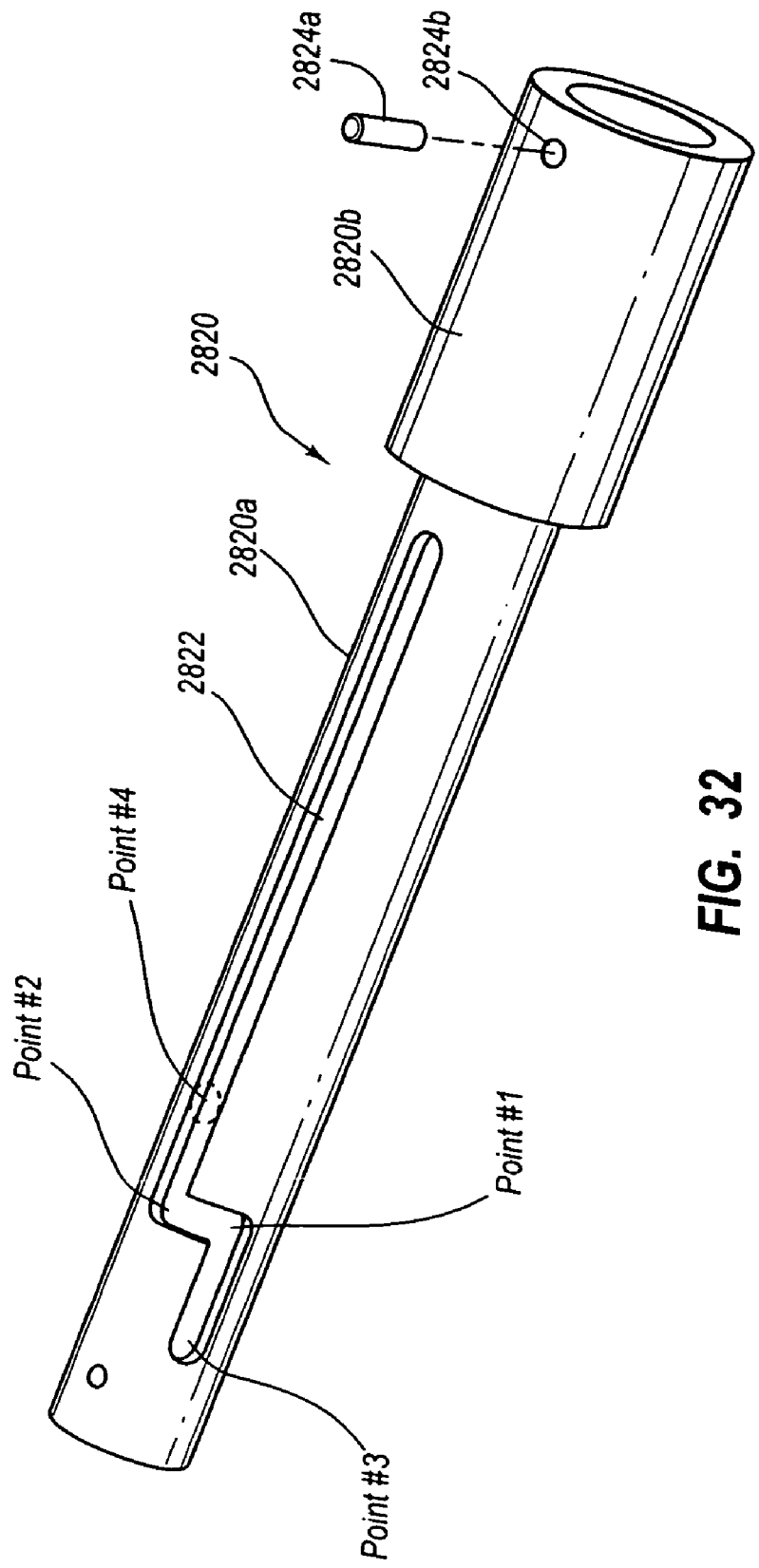

With reference to FIGS. 28 and 32, pusher handle 2820 can be a substantially hollow, rigid generally cylindrical member. Pusher tube 2834 can be coupled to pusher handle 2820. In this manner, movement of pusher handle 2820 relative to main handle 2802 in the distal direction can result in the deployment of PFO closure device 3000 from guide catheter 2818. In the illustrated embodiment, pusher handle 2820 can include a first portion 2820*a* and a second portion 2820*b*. First portion 2820*a* can be sized and configured to be received and movable within at least a portion of main handle 2802. First portion 2820*a* can include a track 2822. Track 2822 can be configured to serve as a guide for stops 2812 and 2814. Track 2822 can be configured to receive set screws of stops 2812 and 2814 therein, such that set screws can translate along track 2822.

Track 2822 can include various points, generally labeled as Point #1, Point #2, Point #3 and Point #4. The distance between Points #3 and #1 can correspond to the distance sufficient to expose and deploy distal anchors 3006 from guide catheter 2818 as pusher handle 2820 moves with respect to main handle 2802 in the distal direction. Furthermore, this distance can be sufficient to maintain proximal anchors 3008 within guide catheter 2818. The distance between Point #2 and the most proximal point in track 2822 can correspond with a distance sufficient to enable the entire PFO closure device 3000 to deploy from guide catheter 2818.

Figure 34A:
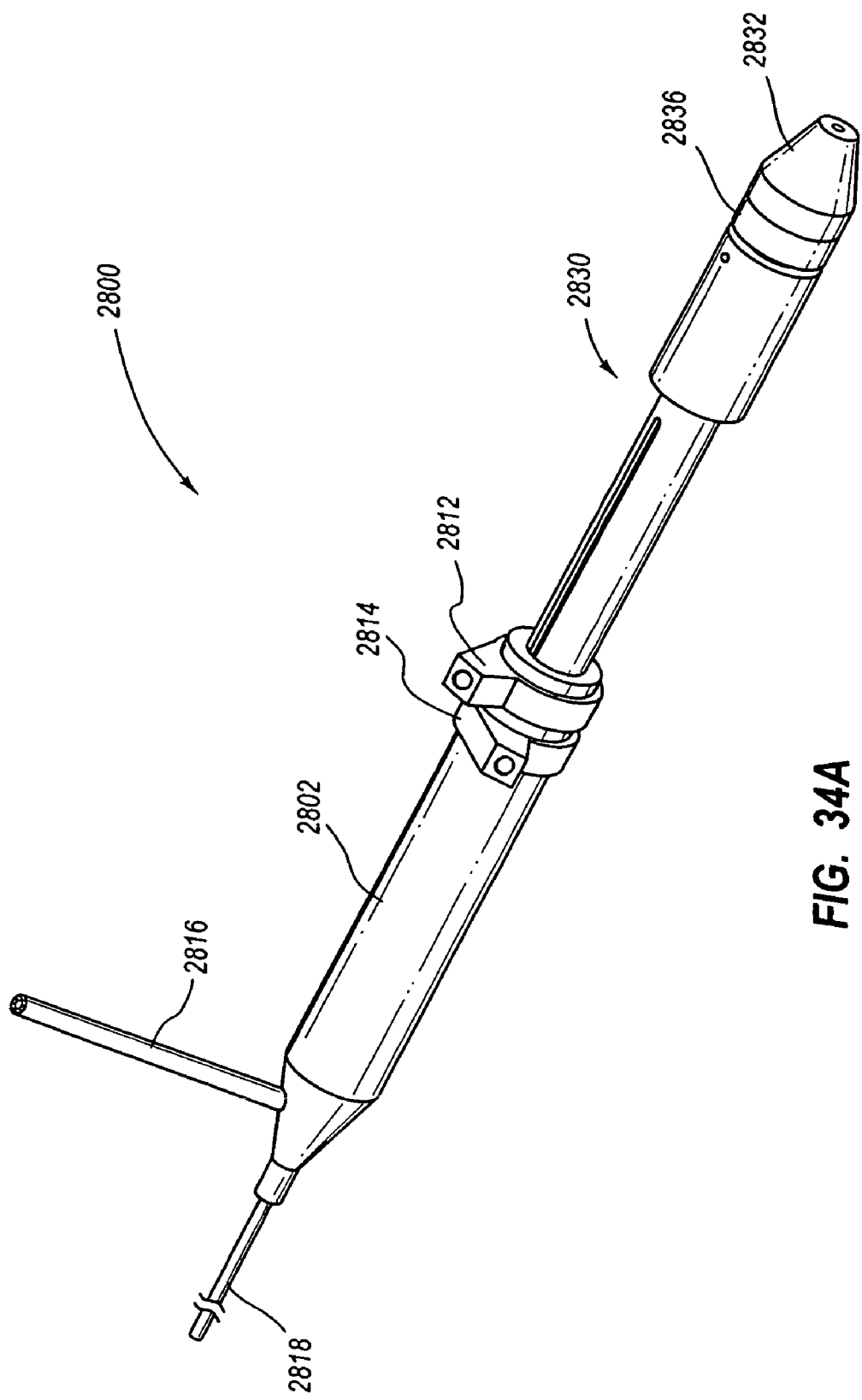
Figure 34B:
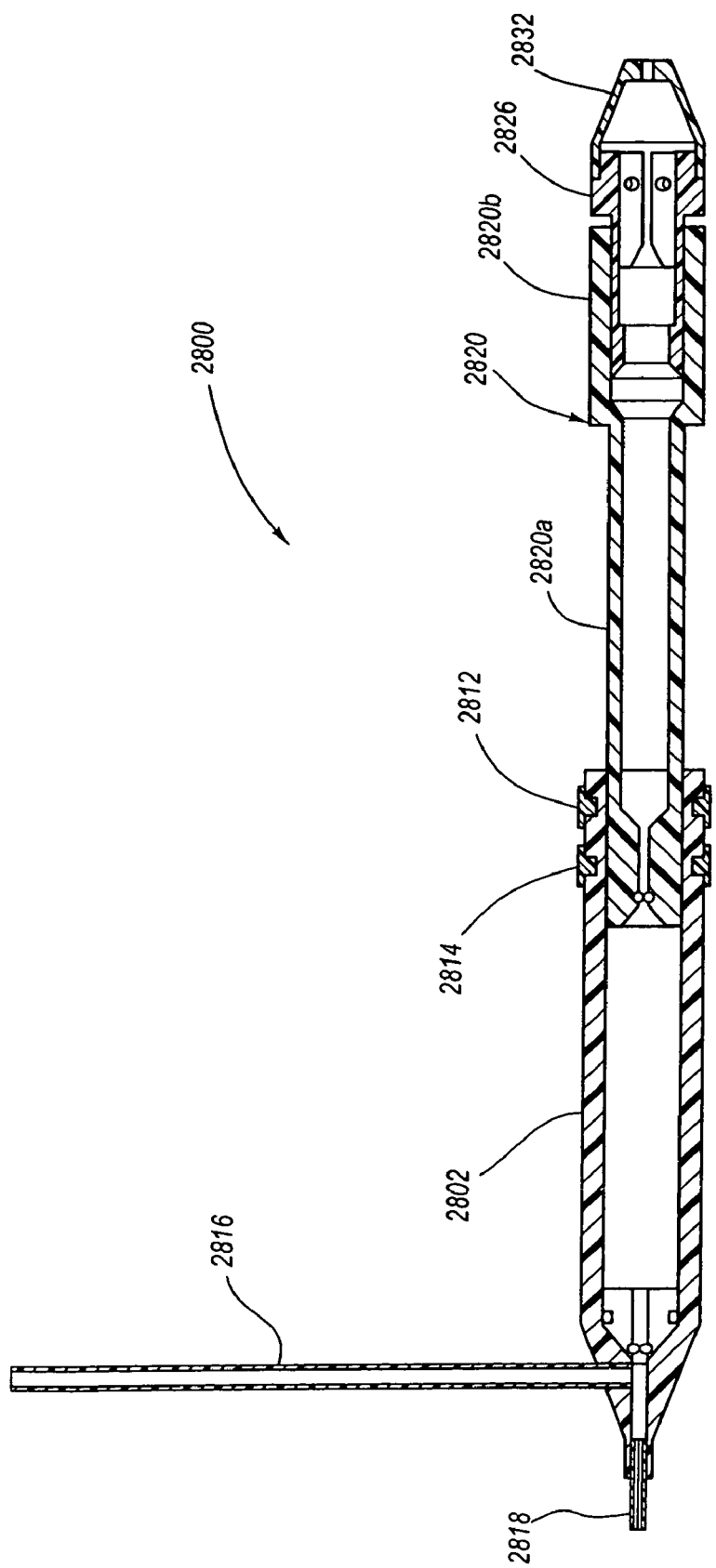
Figure 35A:
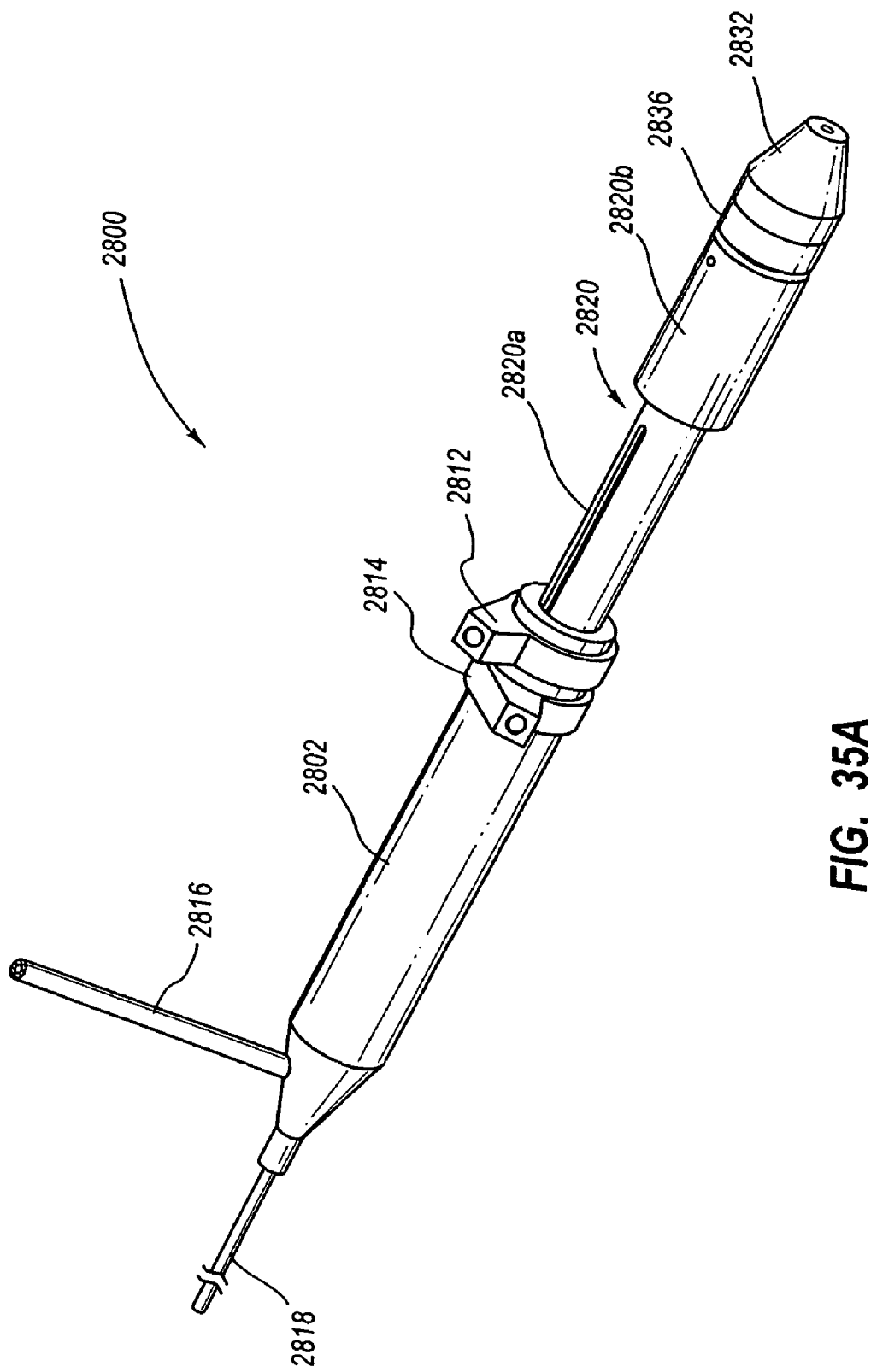
Figure 35B:
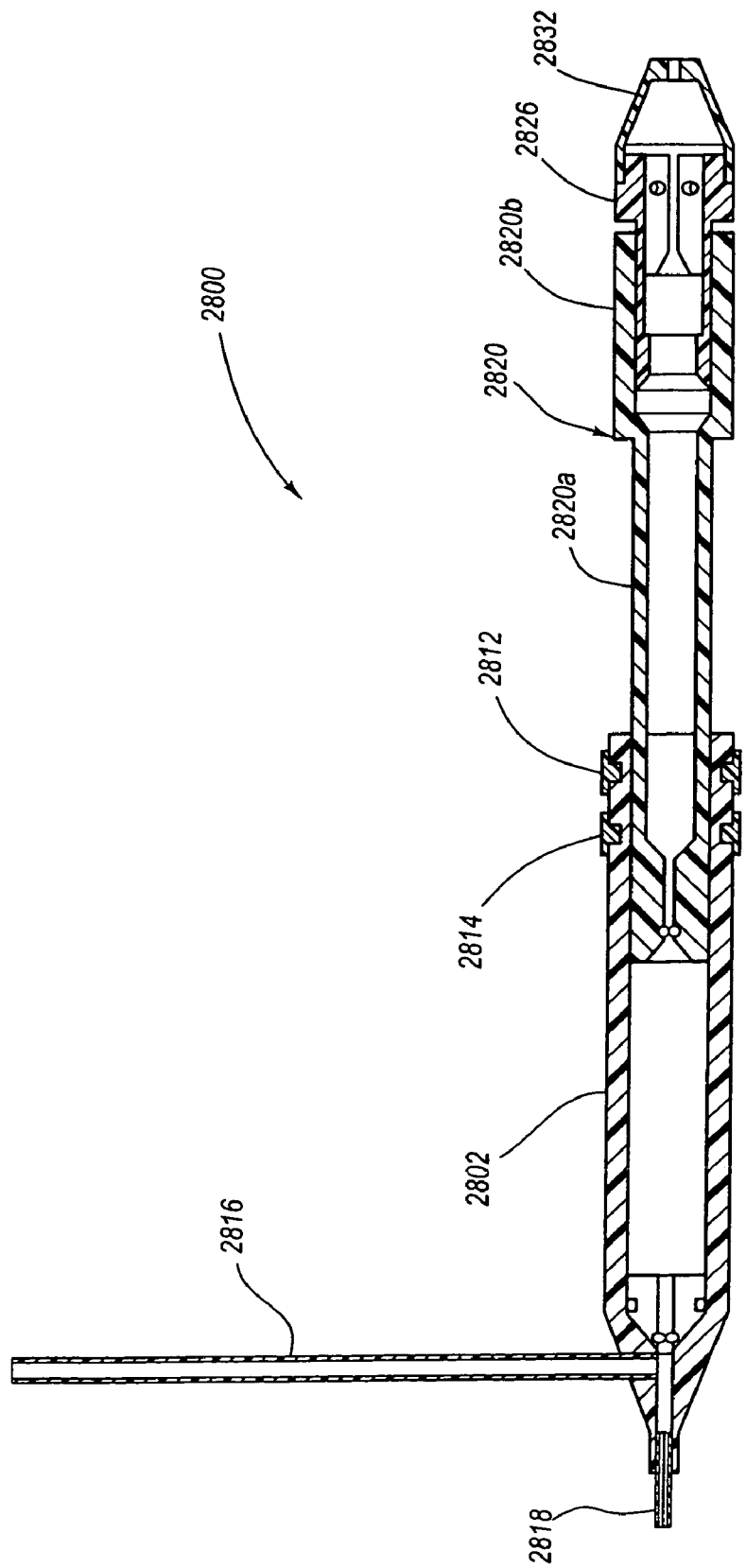
Figure 36:
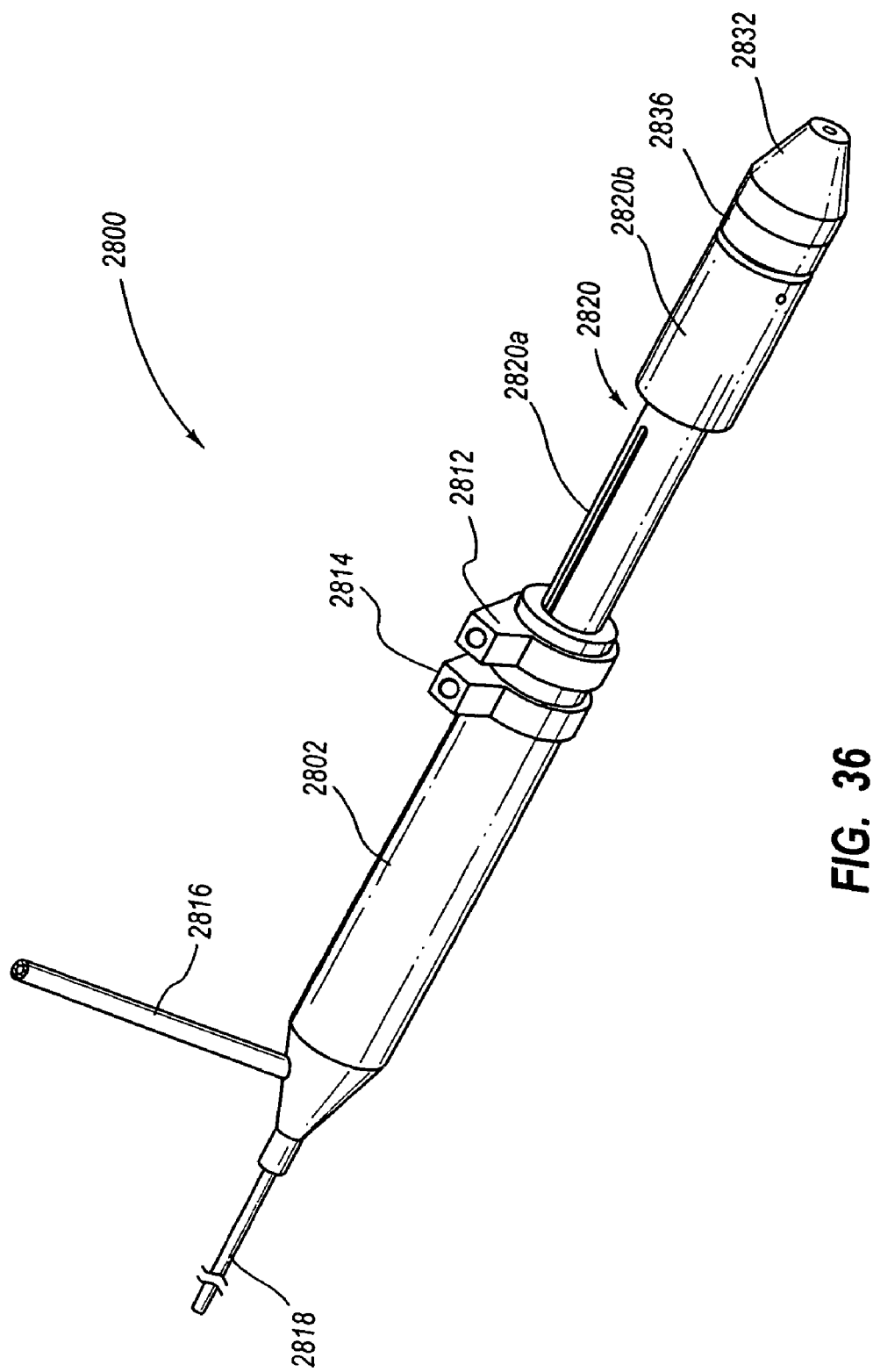
Figure 37A:
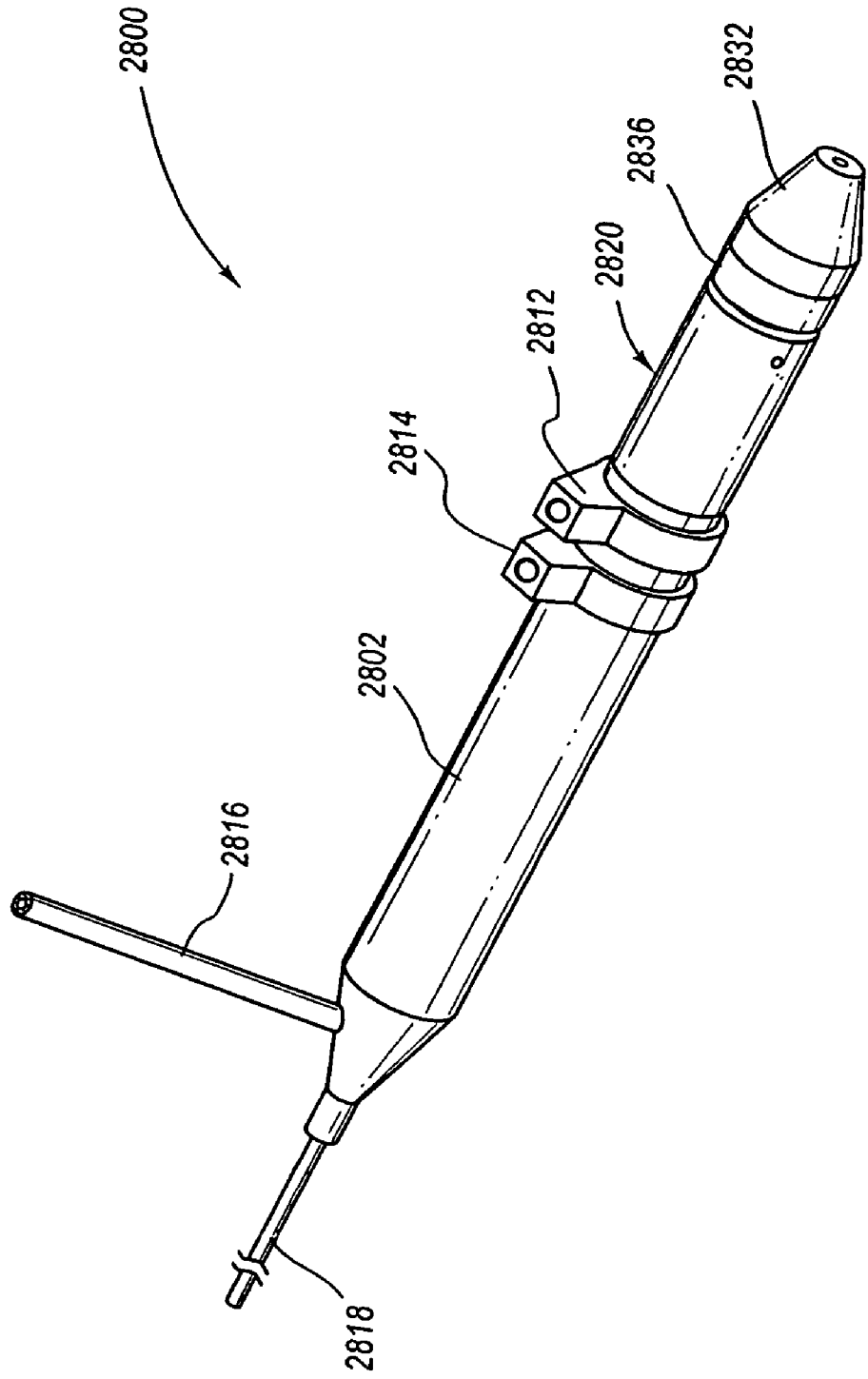
Figure 37B:
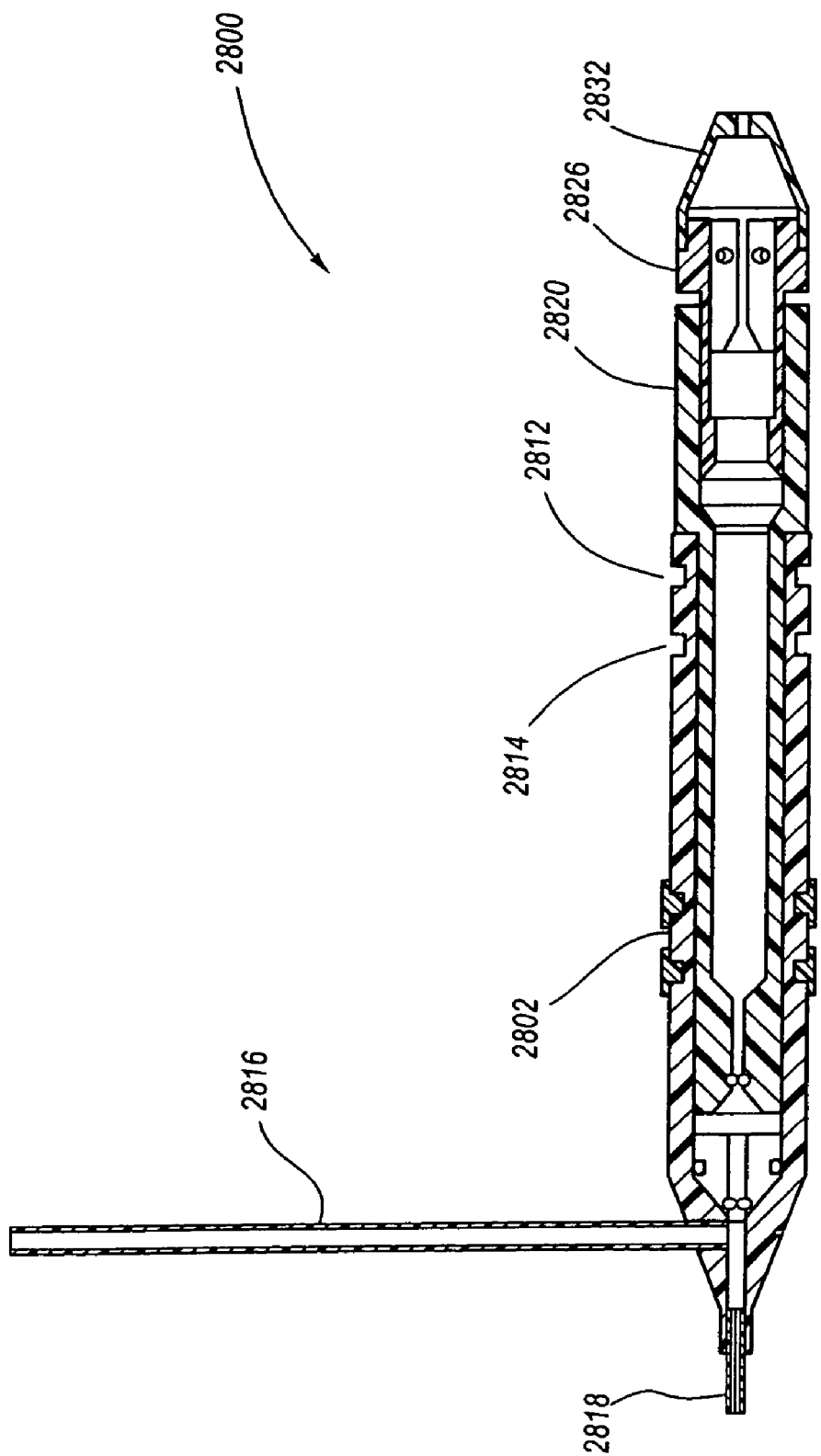

First and second stops 2812 and 2814 can be movable between a closed and open position. For example, first stop 2812 is in a closed position when the set screw of first stop 2812 is at Point #1 and in an open position when the set screw is at either of Points #2 or #4. Second stop 2814 is in the closed position when the set screw of second stop 2814 is either at Points #3 or #1, and in the open position when the set screw of second stop 2814 is at either of Points #2 or #4. As illustrated in FIG. 28, first and second stops 2812 and 2814 are in the closed position; as illustrated in FIGS. 34A and 35A, first stop 2812 is in the open position and second stop 2814 is in the closed position; as illustrated in FIGS. 36 and 37A, first and second stops 2812 and 2814 are both in the open position.

Second portion 2820*b* of pusher handle 2820 can be configured to receive at least a portion of release knob 2826 therein. Second portion 2820*b* can include a pin hole 2824 through which a pin 2824*a* can be received. Pin 2824*a* can be configured to be received and movable along a track 2828 of release knob 2826. It will be understood by one of ordinary skill in the art in view of the disclosure provided herein that the various pin and groove configurations serve as a guide and that other configurations can perform the same function without departing from the scope and spirit of the invention. For example, the pin and groove configurations may be replaced by various linkages that allow movement sufficient to enable the various elements of the invention to function correctly.

Figure 33:
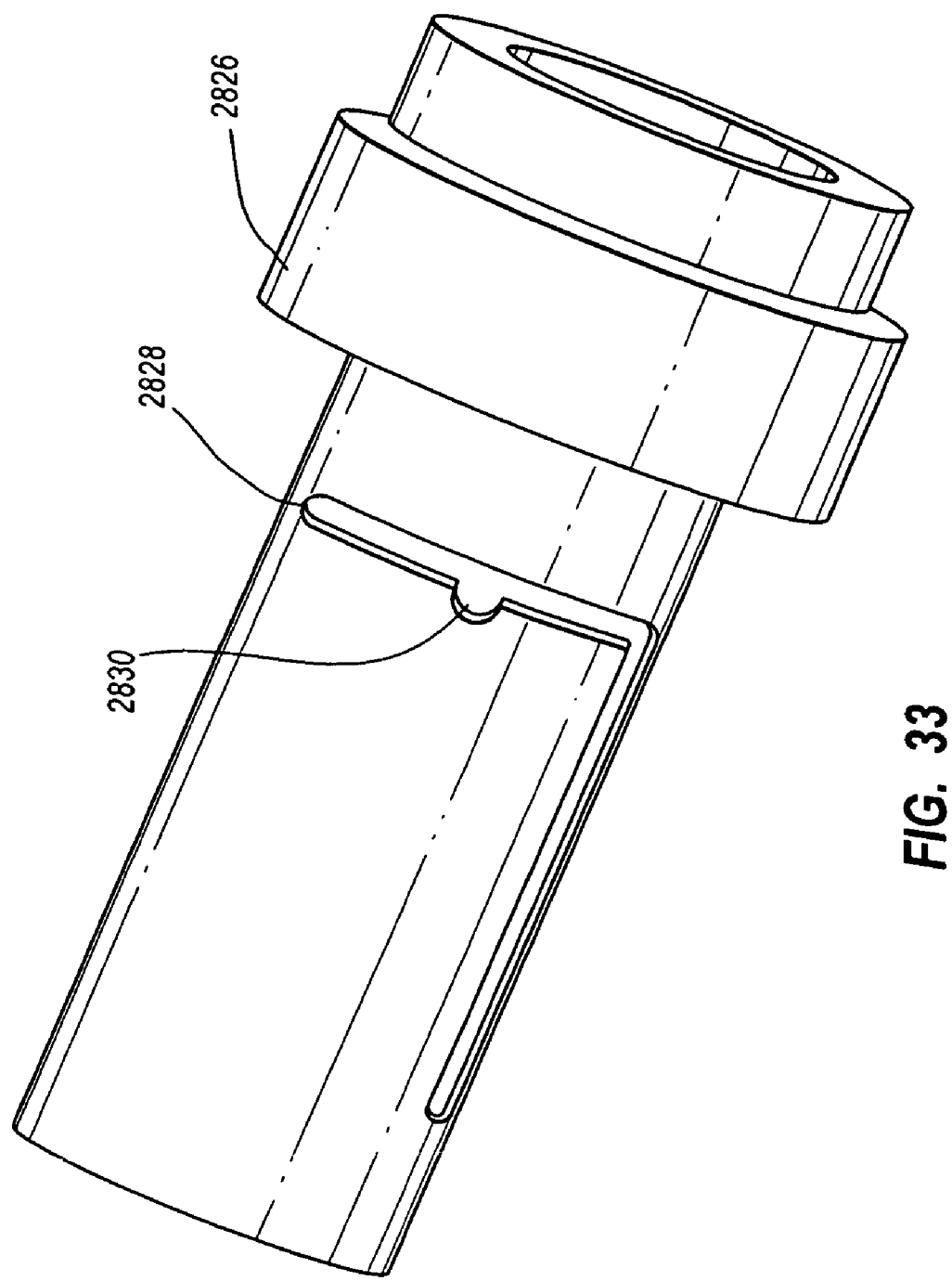

Release knob 2826, as illustrated in FIG. 33, can be configured to facilitate detachment of the closure device 3000 from delivery device 2800. At least a portion of release knob 2826 can be sized and configured to be received and movable within the proximal end of pusher handle 2820. Detachment wires 2838 can be coupled to release knob 2826. In this manner, movement of release knob 2826 relative to pusher handle 2820 in the proximal direction can result in detachment of PFO closure device 3000 from delivery device 2800.

Release knob 2826 can include a track 2828. Track 2828 can be configured to receive a portion of the pin 2824*a* (FIG. 32) from second portion 2820*b* of pusher handle 2820 therein and serve as a guide for movement of the pin 2824*a*. Track 2828 can be configured to allow release knob 2826 to rotate and/or translate relative to pusher handle 2820 in either clockwise or counterclockwise directions. The configuration of track 2828 can constrain the movement of release knob 2826 relative to pusher handle 2820 such that the path of movement of release knob 2826 relative to pusher handle 2820 is prescribed by the configuration of track 2828. Track 2828 can include a detent 2830. Detent 2830 can be configured to reduce movement of release knob 2826 relative to pusher handle 2820, such that release knob 2826 does not inadvertently move detachment wires 2836 relative to tube cap 2840 thus enabling displacement of foot 3014 of PFO closure device 3000 out of slot 2842 of tube cap 2840.

Delivery device 2800 can further include an end cap 2832, as illustrated in FIG. 34A. End cap 2832 can be coupled to the proximal end of release knob 2826. End cap 2832 can be configured to allow various wires and/or tubes to extend therethrough, such as, but not limited to, a thermocouple, electrode wires, RF wire(s) or conductor(s). Guide catheter 2818, main handle 2802, pusher handle 2820 and release knob 2826 can also be configured to allow various wires to extend therethrough, such as a thermocouple, electrode wires, and/or RF wire(s) or conductor(s). Furthermore, guide catheter 2818 and main handle 2802 can further be configured to allow pusher shaft 2836 to extend therethrough and be moveable therein.

The guide catheter 2818 is adapted to be positioned through the PFO such that the distal end of guide catheter 2818 is in the left atrium. The PFO closure device 3000 can then be deployed from guide catheter 2818 by moving pusher handle 2820 relative to main handle 2802, whether such movement includes moving pusher handle 2820 toward main handle 2802, main handle 2802 toward pusher handle 2820, or a combination thereof. This can be accomplished by the following procedure. First, first stop 2812 can be moved from the closed position to the open position, thus moving the set screw of first stop 2812 from Point #1 to Point #2, as illustrated in FIG. 34A. Then, main handle 2802 can be moved proximally with respect to pusher handle 2820 such that the set screw of first stop 2812 moves from Point #2 to Point #4 and the set screw of second stop 2814 moves from Point #3 to Point #1, as illustrated in FIG. 35A. This movement of main handle 2802 relative to pusher handle 2820 can be sufficient to cause distal anchors 3006 of closure device 3000 to extend out from the distal end of guide catheter 2818 and deploy into the left atrium.

A user can then manipulate the main handle 2802 until distal anchors 3006 are positioned against tissue adjacent the PFO in the left atrium. To deploy proximal anchors 3004, a user can move second stop 2814 to the open position (set screw of second stop 2814 moves from Point #1 to Point #2) as illustrated in FIG. 36, and then further proximally move main handle 2802 relative to pusher handle 2820, as illustrated in FIG. 37A. The length of track 2822 from Point #2 to the terminating proximal point can be sufficient so as to allow main handle 2802 to move enough for proximal anchors 3008 to fully extend out of the distal end of guide catheter 2818 and deploy, thus engaging the tissue adjacent the PFO in the right atrium.

Figure 38A:
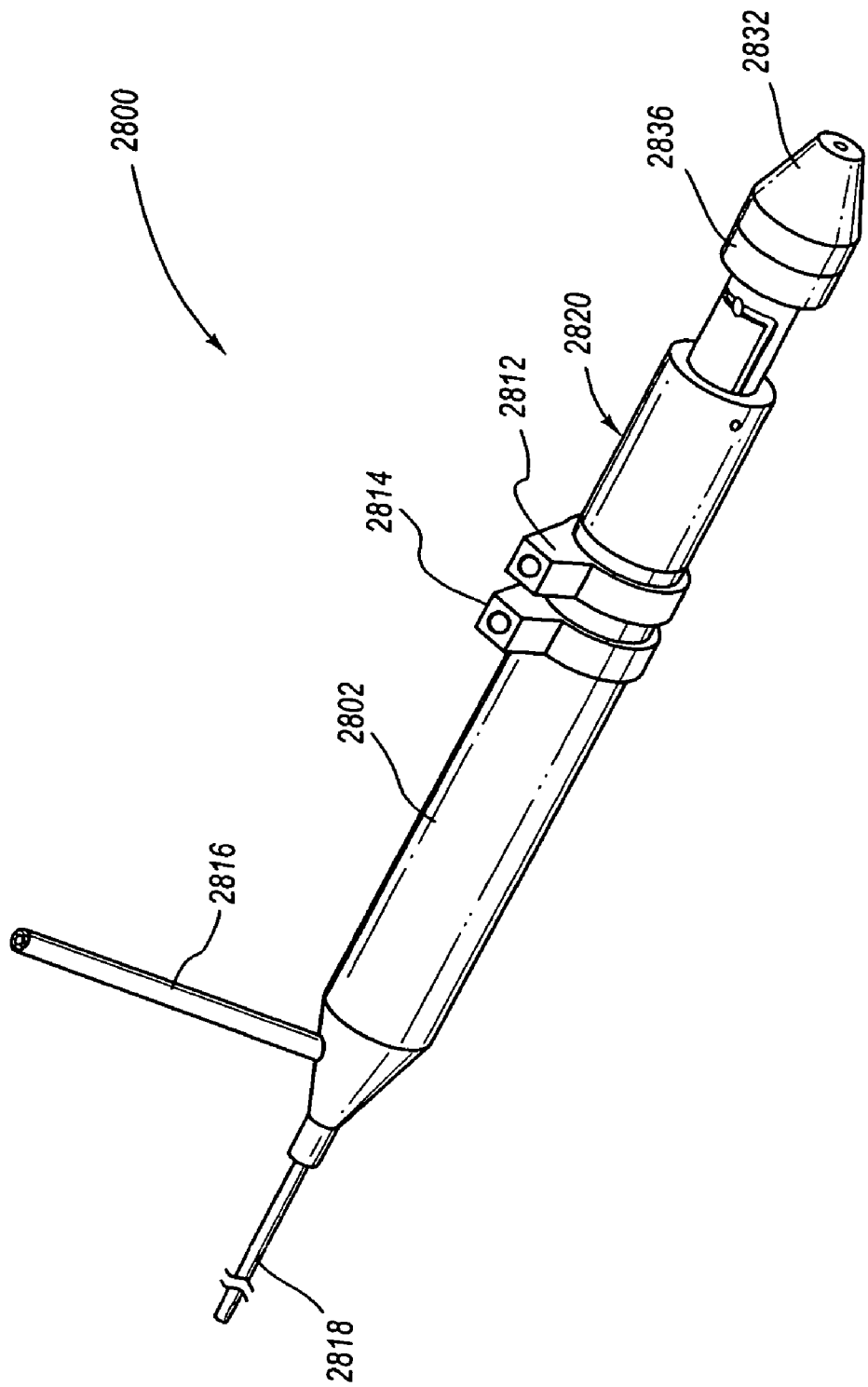
Figure 38B:
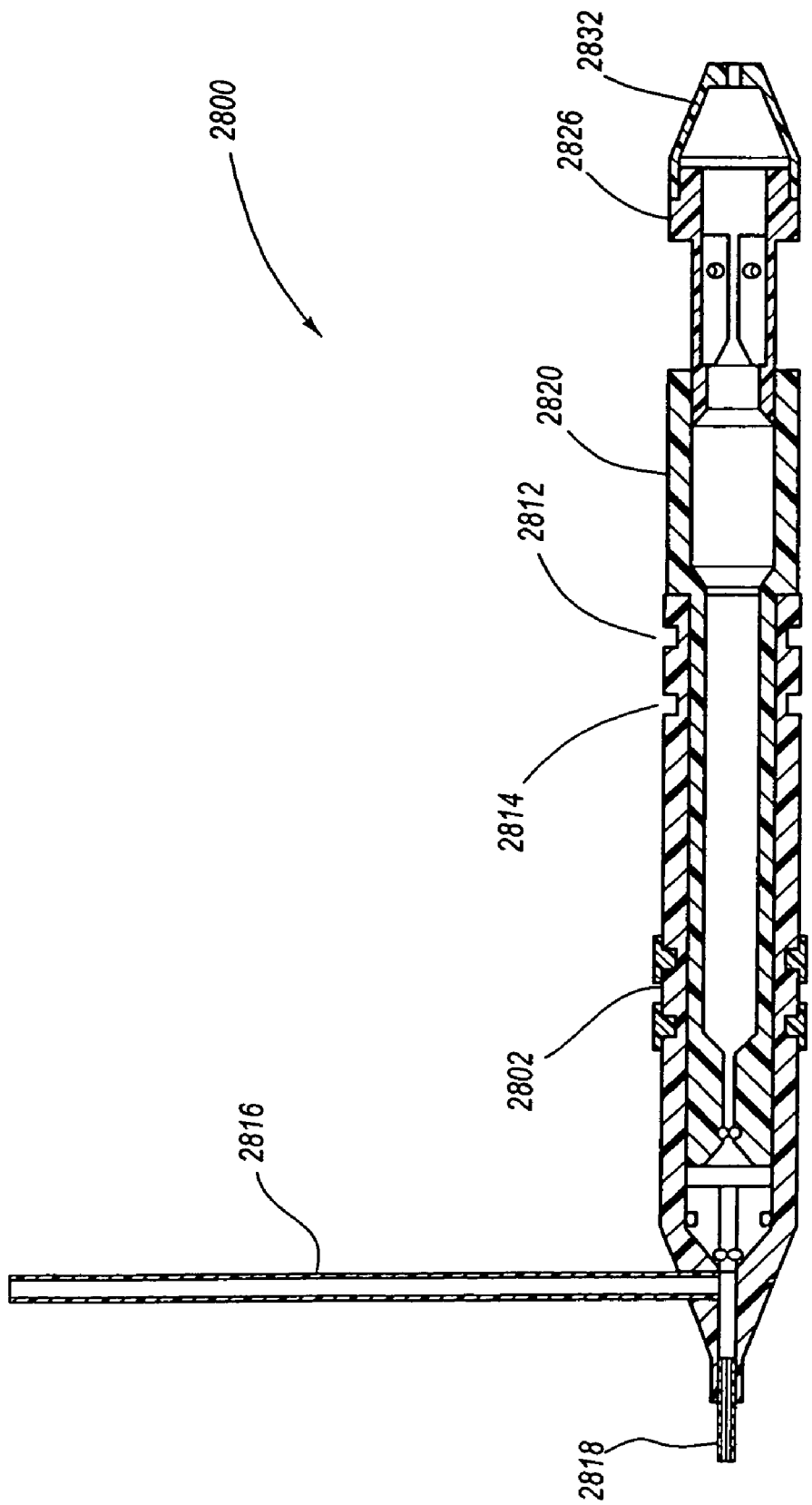

PFO closure device 3000 can be detached from delivery device 2800 through use of release knob 2826. Moving release knob 2826 proximally with respect to pusher handle 2820, as illustrated in FIG. 38A, can cause detachment wire 2838 to be pulled proximally through tube cap 2840. The configuration of track 2828 of release knob 2826 and pin of pusher handle 2820 enable release knob 2826 to be moved relative to pusher handle 2820 sufficiently to cause detachment wire 2838 to move proximally past foot 3014 of tab 3012. As detachment wire 2838 is moved past foot 3014, foot 3014 can be moved out of slot 2842 via the ramp 3014a of foot 3014. In this manner, tab 3012 can be detached from flexible tube 2836, and thus detached from delivery device 2800. At this point, PFO closure device 3000 is positioned and delivery device 2800 can be removed from the patient.

Although reference is made hereinto to the delivery device 3000 and deployment of the same, it will be understood that the present invention can more generally apply to the delivery and positioning of a structure disposable within a body lumen, where the structure can optionally receive RF or other electromagnetic energy to aid with implanting the structure, whether or not the structure is a generally planar structure.

FIG. 39A illustrates a closure device 90 that includes an in-growth media configuration 3900 attached thereto. The closure device 90 includes a plurality of cells 3902. The in-growth configuration 3900a may include filament 3905 secured to a central portion of the closure device 90. Securing filament 3905 to the central portion of the closure device 90 may encourage tissue in-growth into the closure device 90 within the center of the closure device 90 rather than the perimeter portions of the closure device 90 that may be exposed to flowing blood. As illustrated in FIG. 39A, the filaments 3905 are coiled around portions of one or more of the cells 3902. In-growth material in this embodiment can include fibers of biocompatible polymers such as Dacron (polyester), PTFE, or other filaments that provide a relatively large amount of surface area into which tissue can grow.

In FIG. 39A, the filament 3905 is depicted as a single fiber. While a single fiber may be used, the filament 3905 may also represent a fiber bundle that may have a braided structure, or a twisted structure. The surface of the fiber bundle may have many protruding ends of the individual fibers as a result of a looser braid or twist. The additional fiber ends can provide surfaces for in-growth as tissue forms around them. The fiber or fiber bundle may be secured to the structure of the cell 3910 by thermal bonding or adhesives.

An in-growth configuration 3900b that includes filament 3905 is shown in FIG. 39B. As illustrated in FIG. 39B, the closure device 90 may include features 3910, such as holes, formed into the closure device 90. The features 3910 may provide additional anchoring points for the filament 3905. The filament 3905 may be loosely sewn through these points, or fixed by adhesive or knots in the filament near each feature 3910 through which the filament 3905 passes.

Though not shown, the filament 3905 may extend over only a single cell or throughout all of the cells of the structure. Further, the path of the filament 3905 is shown being weaved to alternating sides of the structure. In such a configuration, the filament 3905 may have the ability to take up space out of the plane of the structure. Additionally, when the closure device 90 is in a compressed state for delivery, all of the fiber material may be kept out from between the struts of the closure device 90, which may allow for more efficient packing of the compressed structure for delivery through or by way of a catheter.

In at least one example, in-growth media, such as in-growth filaments, may be attached to the closure device by way of loops of wire, suture material or threads of in-growth material. In such an example, the in-growth media may be attached to one side of the closure device structure. In other examples, the in-growth media may be sandwiched between two PFO closure devices that are connected. The use of multiple closure devices may provide for the separation of functions of the structure (e.g., anchoring and tissue expansion) while also providing a secure place for the media. In yet another example, the in-growth media may be woven through the cells of the closure device and can be secured by the weaving or additional securing techniques or members could be provided as well.

In another example illustrated in FIG. 39C, the in-growth configuration 3900c includes filament 3905 secured to the closure device 90 in a pattern. The pattern of the in-growth configuration may increase the relative amount of in-growth media that is secured to the closure device 90. Further, the pattern illustrated, the points at which the filaments 3905 are attached are maintained at a constant distance from each other as the closure device 90 is deployed. Such a configuration may provide for a degree of tightness of the filament 3905 to remain relatively constant over a wide range of deployment.

FIG. 39D illustrates an in-growth configuration 3900*d* in which the points at which the filament 3905 is secured to the closure device 90 are not maintained at a constant distance from each other as the closure device 90 is deployed. Such a configuration may result in relative slack in the filament 3905 as the closure device 90 is deployed.

FIG. 39E illustrates an in-growth configuration 3900*e* in which strips 3915 of in-growth media are secured to the closure device 90. In particular, the strips 3915 of in-growth media may be secured to opposite sides of a cellular portion of the closure device 90. The strips 3915 may be loosely woven gauze-like material that is woven into an interlocking structure. The strips 3915 may be secured to the closure device 90 in any suitable manner. As illustrated in FIG. 39F in configuration 3900*f*, the strips 3915 may be wrapped around a cellular portion of the closure device 90 and back onto the strips 3915. The overlapping portions of the strips 3915 may then be secured to each other.

FIG. 39G illustrates an in-growth configuration in which one or more membranes 3920 are secured to a closure device 90. The membrane 3920 may include a number of materials, including, without limitation, fibers of Dacron (polyester), PTFE, or bio-absorbable polymers that are formed into a membrane through weaving, knitting, or some other manner. The membrane patterns may be precut as desired and secured to the closure device 90 in any suitable manner.

In addition to securing in-growth media to a single closure device, in-growth media may also be secured to multiple closure devices that are configured to be deployed in concert. In particular, FIG. 39H illustrates an in-growth configuration in which the membrane 3920 is sandwiched between two closure devices 90*a*, 90*b* that have been crimped together. The use of multiple closure devices 90*a*, 90*b* may increase the stiffness of the two devices when used together while allowing secure attachment of the membrane 3920.

Figure 39I:
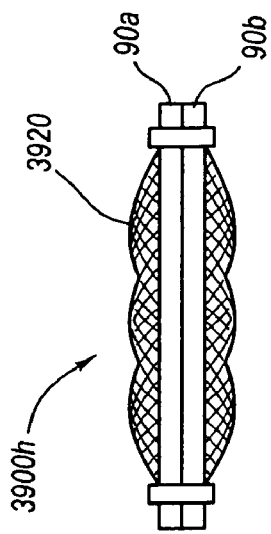
Figure 39K:
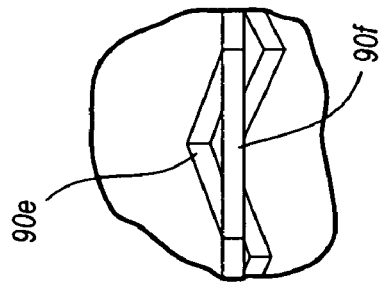
Figure 39H:
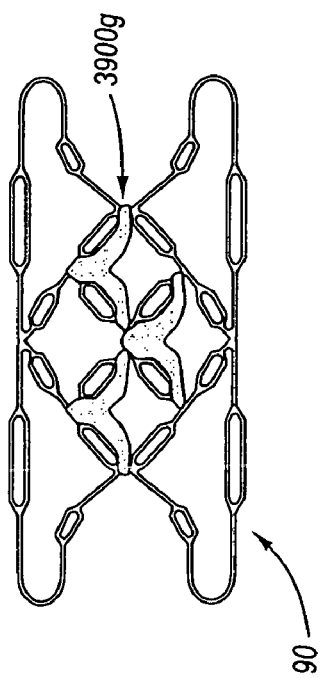
Figure 39J:
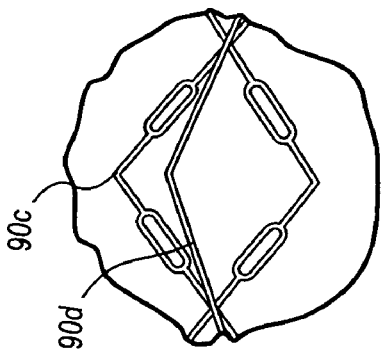
Figure 39M:
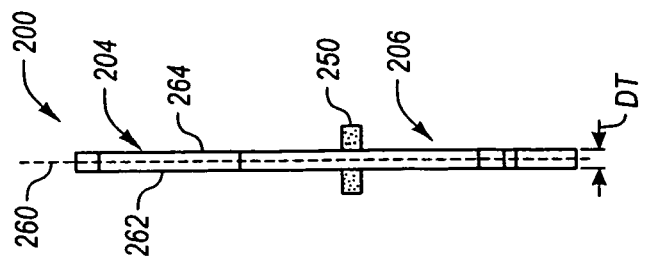

FIGS. 39I and 39J also illustrate additional configurations in which multiple closure devices are used in concert. In FIG. 39I the closure devices 90*c*, 90*d* are configured differently. FIG. 39K illustrates a similar configuration in which closure devices 90*e*, 90*f* are different. The second closure device 90*f* may be biased out of plane relative to the first closure device 90*e*. Such a configuration may also provide out-of-plane structure to contact surrounding tissues to thereby secure the closure device 90*e* in the internal tissue opening.

Figure 39L:
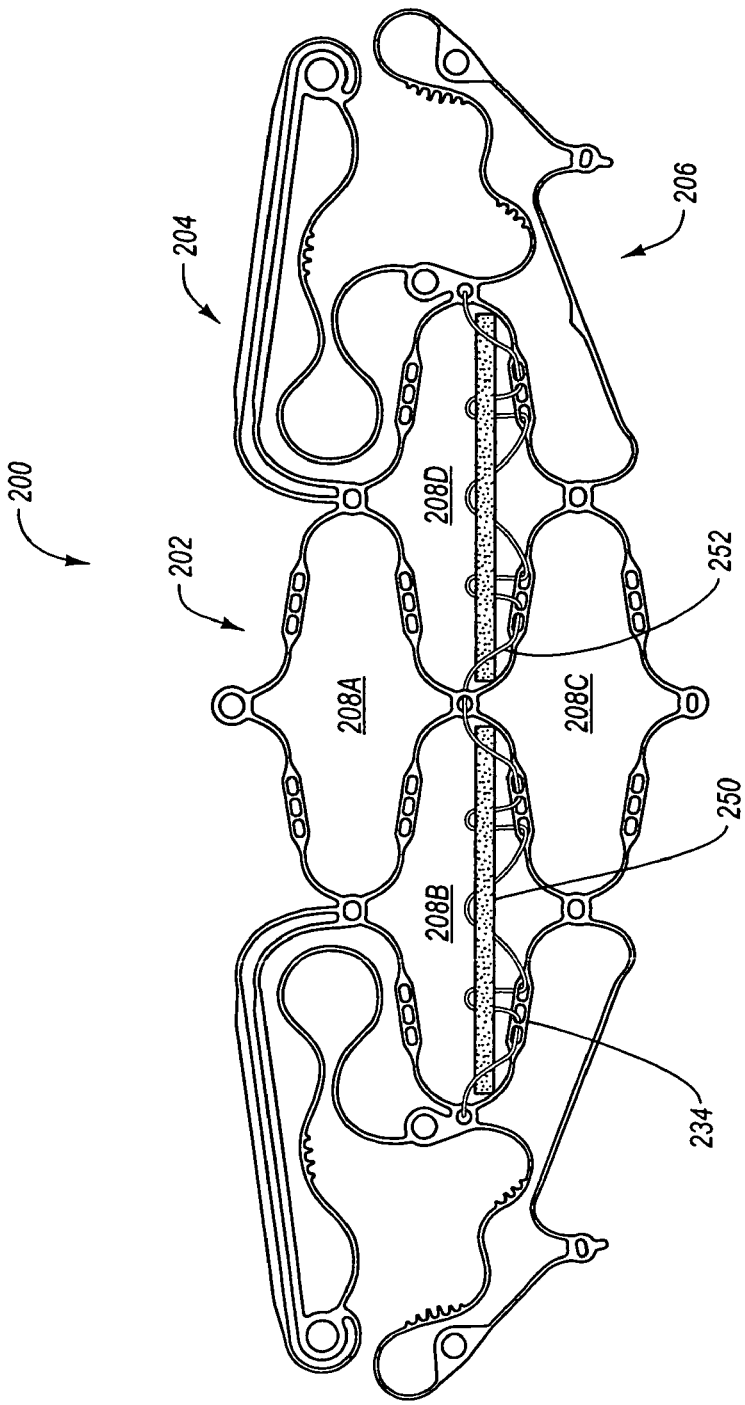

FIG. 39L illustrates one embodiment of a closure device 200 that can include a member 250, such as an in-growth material. The member 250 can be configured to induce tissue growth. The member 250 can be fixed to the closure device 200 by means of a securing element, such as a thread 252. For example, the thread 252 can extend through the member 250 and through the apertures in the intermediate portions 234 in order to secure the member 250 to the closure device 200. In other embodiments, the member 250 can be secured to the closure device 200 by a known securing means, such as by an adhesive, a heat weld, or some other known or hereafter developed means for securement.

The member 250 and the thread 252 can include a bioresorbable material, such as polylactide or polyglycolide or collagen. The member 250 can be sized and configured to enable the closure device 200 to be deployed from and received into the delivery portion 366 of the delivery device 300. Furthermore, the member 250 can be configured to interact with tissue of the internal tissue opening to stimulate growth of tissue for closure of the internal tissue opening. For example, the member 250 can interact with the tunnel tissue 58 of a PFO in order to stimulate growth of tissue in the PFO tunnel 58.

The member 250 can be any suitable material that can or tends to promote tissue growth. Examples of such material can include a polymeric material, or a woven material, such as a woven metallic or biological material. In one embodiment, the member 250 can be a piece of foam. In alternative embodiments, the member 250 can be a piece of yarn, fabric or string, or some combination thereof. Other tissue growth-promoting members can include a coating disposed on the closure device 200. In other embodiments, the member 250 can be a piece of foam, braided material such as a piece of yarn or string, or fabric that has a coating disposed thereon.

The member 250 can include materials such as a piece of polyurethane or some other biocompatible polymer, including bioresorbable polymers. The member 250 can also include Dacron or polymeric threaded materials that have been woven or knitted, or formed into compressed, nonwoven fabrics. The member 250 can also include a metallic material, such as a NiTiNol, stainless steel or some other biocompatible alloy or bioresorbable metal, such as magnesium alloy, or some combination thereof. In one embodiment, the member 250 comprises a metallic wire.

FIG. 39M illustrates a side view of the closure device 200, and illustrates one example of the closure device having a substantially flat configuration. In the illustrated embodiment, the closure device 200 can include a depth or depth thickness designated as DT, and a plane 260 extending perpendicularly into and out of the plane of the page. In this embodiment, the member 250 can extend beyond at least a first edge 262 of the closure device 200. Furthermore, the member 250 can extend beyond both the first edge 262 and a second edge 264 of the closure device 200. In this manner, member 250 can contact tissue adjacent the closure device 200 to promote tissue growth in the tissue opening.

The member 250 can be sized and configured to extend beyond at least the first edge 262 of the closure device 200 a sufficient distance to contact tissue of the tissue opening. In one embodiment, the member 250 can extend beyond at least the first edge 262 a sufficient distance to contact tissue adjacent the first edge 262, thereby causing the end of the member 250 that is in contact with the tissue to deflect or bend. In this manner, more surface area of the member 250 can be in contact with tissue to thereby facilitate an increase in tissue growth. In other embodiments, the member 250 can extend beyond both the first edge 262 and the second edge 264 a sufficient distance to cause both ends of the member 250 to bend, which can result in more surface area contacting the tissue. In one embodiment, the member 250 can extend between at least 0.5 mm and 5 mm beyond the first edge 262. In another embodiment, the member 250 can extend between at least 0.5 mm and 5 mm beyond the first edge 262, and can extend between at least 0.5 mm and 5 mm beyond the second edge 264. Furthermore, the member 250 can have a thickness of between at least 0.25 mm and 2 mm.

In addition, in some embodiments the member 250 can be configured to decrease the size of a remaining void in the tissue opening after the closure device 200 has been positioned in the tissue opening. Member 250 extending beyond the first edge 262 of the closure device 200 is an example of the member 250 extending substantially out of plane of the substantially flat configuration.

As discussed, cell structures may be variable and/or irregular. A completely random structure of very small cells can also have properties that provide the correct force to the internal tissue opening. These structures may be constructed of fine wire that has been shaped into the desired flat form but has sufficient voids to allow for compressibility within a delivery system. Other random celled structures may be constructed from polymer foams such as, but not limited to, ePTFE or polyurethane.

For metallic-based structures for implant, the surface finish may be electro-polished. In this application, all, or specific portions of the device, may be electro-polished to provide a smooth and trauma-free surface. The edges of the device may be specifically designed to contact the inner side walls of the tunnel and may be electro-polished to prevent sharp edges of the structure from puncturing the tissues except for specific locations where it is desired for anchoring. A smooth surface on the edge can also be amenable to coating, which can add lubricity for ease of delivery. Rougher surfaces on surfaces of the device other than the outer edge may be desirable and can aid in providing anchoring locations and/or locations for more aggressive tissue in-growth after implantation. In portions of the structure where more roughness is desired, the roughness may be added by grit-blasting, chemical etching or other mechanical means using appropriate abrasives. Polymer structures may be similarly smooth or textured as desired for fixation and in-growth.

Closure devices can also be adapted to serve as a drug delivery platform and/or the placement of other substances that can enhance the closing of internal tissue openings. In at least one example, drugs may be delivered by elution, such as from a polymer-based coating. Such drugs may include, without limitation, drugs that can induce the closing of an internal tissue opening, such as vascular endothelial growth factor, synthetic or naturally occurring proteins, and/or refined proteins such as collagen or bovine serum albumin.

Structures that perform the same functions as the multi-celled structures may also be constructed from a single member. The single-member structure may include anchoring features as shown herein, where an anchor is made to anchor the device from the distal side of its deployment. After the waist of the structure, a portion of the member is constructed to provide lateral anchoring force within the opening. The bottom-most portion of the device will provide the support for the distal anchors as well as the lateral force exerted through the waist of the device. A relief in the most proximal portion of the member may be provided to allow the closure device to be collapsed within a catheter for delivery. Other means of providing this relief may be used such as a coil spring or a localized material property modification of that section of the member. A single member structure may also have integral, more complex anchors (3) as depicted in FIG. 14B.

In addition to the above, it may be desirable to add additional features to encourage in-growth to close an internal tissue opening, such as a PFO. Threads or fabric of polymeric materials such as Dacron felt, fabrics or filaments, PTFE, ePTFE or the like, may be wrapped around the struts of the PFO closure device or woven through the cells to provide more aggressive tissue in-growth surfaces where desired. Fine metallic wires, meshes or braids may also be used. Alternatively, fabric or thin membranes may be sewn, welded, or adhered to the struts to cover any desired part of the PFO closure device.

In addition to the embodiments and configurations described above, the present invention can also be related to various other medical devices, systems, and methods. For instance, in another configuration, disclosed a medical device that has a multi-cellular structure being configured to be moved from a collapsed state to an expanded state, the multi-cellular structure including a waist portion and at least one anchor portion, wherein the anchor portion is wider in the expanded state of the device than the waist portion and the waist portion is configured to engage a tunnel of an internal tissue opening in the expanded state to close the internal tissue opening. This device can also include one or more distal anchors and/or proximal anchors. These anchors can be substantially the same width, or one may be wider than the other. These anchors may also include a plurality of elongate arms. One or more of the elongate arms may have a serrated edge, such as a serrated edge configured to face toward the center of a tunnel of an internal tissue opening when the medical device is deployed. The elongate arms may also have smooth edges. The multi-cellular structure may include a plurality of cellular portions having substantially the same size or the cellular portions may be of different sizes. The medical device may also be configured to shorten its overall length dimension upon deployment. If the medical device has a distal anchor and a proximal anchor, the proximal anchor may be configured to roll at least partially onto itself upon deployment to shorten the overall length of the medical device upon deployment. The medical device may have a spring member secured to the waist and a solid anchor portion. The solid anchor portion may be a solid proximal anchor portion. In one example in which the medical device includes both proximal and distal anchor arms, the waist portion of the medical device may also include a hinged portion. The medical device may be formed of a resilient material such that the medical device is configured to expand from the compressed state to the expanded state due at least in part to spring forces associated with the resilient material. The medical device may also be configured to be expanded from the compressed state to the expanded state mechanically.

A medical device according to one example includes opposing expansion members and at least one connecting member coupling the opposing expansion members. The connecting member may be configured to move the opposing expansion members from a compressed state to an expanded state to seal an internal tissue opening. The medical device may also include a plurality of connecting members and pinned joints between adjacent connecting members and between the connecting members and the opposing expansion arms. The pinned joints may include a ratcheting mechanism configured to allow the connecting members to move relative to each other to allow expansion of the expansion members during deployment but to prevent the expansion members from collapsing after deployment of the medical device. The medical device may further include an actuation member, such as a cable or tether, coupled to at least one connecting member. The expansion arms may be configured to be expanded from the compressed to the expanded state by drawing the actuation member proximally. The medical device may also include a locking member configured to lock the expansion member in the expanded state. The locking member may include a clasp operatively associated with the actuation member. Further, the connecting member may have a strut and piston configuration.

In yet another configuration, a medical device includes a plurality of elongate arms and an actuation member coupled to the elongate arms, the actuation member being configured to mechanically expand the elongate arms from a collapsed position to an expanded position. The actuation member may include alternating thinner portions between relatively thicker portions. Further, the actuation member may be configured to be drawn proximally and/or moved distally to mechanically expand the elongate arms. The medical device may also include a body portion operatively associated with the elongate arms. The body portion may include flexing sections and/or pivots coupling the elongate arms to the body portion. The medical device may be a distal locator device, a proximal locator device, and/or a closure device.

In yet another configuration, a medical system includes a first medical device having expandable elongate arms, the expandable elongate arms being configured to expand from a collapsed state to an expanded state and to locate an opening of an internal tissue opening, and a second medical device operatively associated with the first medical device, the second medical device having a multi-cellular structure being configured to be moved from a collapsed state to an expanded state, the multi-cellular structure including a waist portion configured to engage a tunnel of an internal tissue opening in the expanded state to close the internal tissue opening. The first medical device may be a distal locator device or a proximal locator device. For example, the first medical device may be configured to locate a distal opening of the internal tissue opening. The system may further include a third medical device operatively associated with the second medical device, wherein the third medical device includes expandable elongate arms, the expandable elongate arms being able to expand from a collapsed state to an expanded state and to locate a proximal opening of the internal tissue opening. The second medical device may include outwardly facing tines, first anchor portions, and/or second anchor portions.

A device for releasing an implant within a body lumen includes an attachment member coupled to the implant and a push member operatively associated with the attachment member. The device may be configured to secure the implant to a delivery device before release of the implant and to selectively release the attachment member. The attachment member may have a post configuration and the push member has a hole defined therein to receive the post. The attachment member may include a loop of material coupled to the push member and a pin, the loop extending through a hole formed in the attachment member and being secured to the attachment member by the pin, wherein removing the pin releases the attachment member. The attachment member may also include a tab while the push member includes a pin configured to retain the tab in contact with the push member. The tab may have a dog-leg shape. The push member may include a slot defined therein configured to receive a portion of the tab while the device further includes a release wire configured to retain the tab in the slot and to be withdrawn to release the tab from the slot. The pin and tab may be interlocking members held in engagement while retained within the push member and that are released when moved from the push member. The push member may be formed from a meltable material. In such an example, the device may further include a coil of electrically conductive wire in which a portion of the push member extends at least partially through the coil. The device is configured to release the attachment member by heating the coil to melt a portion of the push member. Insulation may surround at least a portion of the coil. The device may also include a current source configured to provide a direct current and/or alternating current to the coil. The current source may be configured to provide an alternating current to the coil at a frequency up to radio frequencies. The coil may also be configured as a resistive temperature device and may be formed from nickel, copper, and/or platinum or any other suitable material.

In another example, the device includes a bimetallic actuator configured to release the attachment member from the push member at a specified temperature range. The bimetallic actuator may include a bimetallic strip and a securing member operatively associated with both the attachment member and the push member. The securing member may be configured to couple movement of the push member to the attachment member when engaged and to be disengaged at a specified temperature range to decouple the attachment member from the push member. The push member and the attachment member may each include a receiving portion, such as a loop, defined therein that allows the securing member to pass at least partially through each of the receiving portions. The bimetallic actuator may be secured directly to the securing member and/or a linkage may couple the bimetallic strip and the securing member. A pivot may also be coupled to the linkage member. A device according to the invention, further includes a pivot coupled to the linkage member. The linkage member may include a first portion proximate the bimetallic strip relative to the pivot and a second portion proximate the bimetallic strip relative to the pivot in which the first portion is shorter than the second portion.

In yet another example, a medical device further includes a shape-memory actuator configured to move between an initial shape below a transition temperature and a preset shape above the transition temperature to secure the attachment member in the initial shape and release the attachment member when moved to the preset shape. The push member may include a receiving portion. The shape memory actuator may extend through the receiving portion in the initial shape to secure the push member to the attachment member and wherein the shape memory actuator is drawn from engagement with the receiving portion when moved to the initial state to release the push member from the attachment member. For example, the attachment member has a recess defined therein and the shape memory actuator engages the recess when in the initial state and is released from engagement with the recess when moved to the preset shape. Multiple shape memory actuators may engage the receiving portion from opposing sides of the attachment member in the preset shape. Further, the device may include a cutting feature secured to the shape memory actuator, the cutting feature being configured to cut a portion of the push member when the shape memory actuator is moved to the preset shape. For example, a cutting feature may have an opening defined therein and at least a portion of the push member may extend through the opening. Additionally, the device may include a linkage and a securing member, the linkage coupling the shape memory actuator to the securing member. The securing member may couple the push member to the attachment member when the shape memory actuator is in the initial shape and release the push member from the attachment member when the shape memory actuator is in the preset shape. A pivot may also be operatively associated with the linkage. In another example, a device includes a cylinder and piston secured to the implant, a linkage, and a securing member. The securing member may be configured to release the push member in response to operation of the cylinder and piston, such as by expansion of the cylinder and piston. A phase change material may be expanded within an enclosed space of the cylinder to drive the piston. Phase change materials may include a hydro-carbon fluid as well as formulations of waxes such as those used in the thermostats of common automotive engines. In one example, a cross-hole is defined in the push member and a hole is defined in the attachment member. The device may further include a flexible filament extending through the cross-hole through the hole and into a distal end of the push member. The device may include a cutting feature. The cutting feature may engage the filament at the cross-hole to cut the filament.

A delivery device for delivering a closure device includes a handle body and a pusher handle operatively associated with the handle body, the pusher handle having a guide slot defined therein. The guide slot may be configured to allow the pusher handle to move linearly with respect to the handle body a first linear distance to deploy a first portion of the closure device. The guide slot may be further configured to allow the pusher handle to move linearly with respect to the handle body additional linear distances to deploy additional portions of the closure device, such as a second linear distance to deploy a second portion of the closure device. The guide slot may be configured to allow the pusher handle to rotate a rotational distance between the first linear distance and the second linear distance. First and second grooves may be defined in the handle body while first and second stops may be associated with the first and second grooves. The first and second stops may be associated with the guide slot. The first and second stops are configured to move between initial positions and rotated positions to constrain the movement of the pusher handle. For example, rotating the first stop to the rotated position allows the pusher handle to move from the first position to the second position and rotating the second stop to the rotated position after rotating the first stop to the rotated position allows the pusher handle to move from the second position to the third position. The linear distance from the first position to the second position may correspond to the first linear distance and the distance between the second position and the third position may correspond to the second linear distance. Accordingly, in one example, the guide slot includes a first linear portion, a transverse portion transverse to the first linear portion and in communication with the first linear portion, and a second linear portion substantially parallel to the first linear portion, the second linear portion in communication with the transverse portion. The delivery device may also include a release assembly configured to release the closure device from the delivery device. The release assembly may include a release cap having a slot defined therein, the slot having a linear portion and a transverse portion transverse to the linear portion in which the linear portion extends proximally of the linear portion. The slot may also include a detent formed defined therein in communication with the transverse portion. In one example, a pin is coupled to the handle portion and is operatively associated with the pin. The delivery device may also include a drain lumen in fluid communication with the handle body.

A medical device has a multi-cellular structure being configured to be moved from a collapsed state to an expanded state, the multi-cellular structure including a waist portion configured to engage a tunnel of an internal tissue opening in the expanded state to close the internal tissue opening, and in-growth media having an in-growth configuration secured to the medical device. The in-growth configuration may include at least one filament secured to a central portion of the medical device, a filament coiled around the central portion of the medical device, and/or anchoring points configured to have the in-growth media secured thereto. The anchoring points may allow the filament to be secured to the medical device by sewing, fixing by adhesive, and/or knots. In another example, points at which the in-growth media is attached to the closure device are maintained at a constant distance from each other as the closure device is deployed. The in-growth media also include strips of in-growth media. The strips may be formed of a loosely woven gauze-like material that is woven into an interlocking structure. The strips may also be wrapped around a cellular portion of the closure device. The in-growth media may also include a membrane. The in-growth media may be located at least partially between the closure device and an adjacent closure device. The closure device and the adjacent closure device may be different or may be substantially similar.

In yet another configuration, a medical device has multiple chambers configured to be inflated from a collapsed state to an expanded state, the multiple chambers having a waist portion configured to engage a tunnel of an internal tissue opening and, in the expanded state, to close the internal tissue opening. The multiple chambers may have a distal anchor portion and/or a proximal anchor portion. The distal anchor portion may be configured to be inflated first and the proximal anchor portion may be configured to be inflated subsequent to inflation of the proximal anchor portion, such as second. The multiple chambers may be interconnected, isolated or a mix of the two. The multiple chambers may also be formed of bioresorbable materials.

In another example, a method for detaching a tether from an implant within a body lumen is provided that includes positioning an implant within a body lumen, a tether being coupled to the implant to aid with positioning the implant within the body lumen, and applying at least one of an electrical input or a thermal input to the tether to detach the tether from the implant. Applying at least one of an electrical input or a thermal input may include applying electrical input to the tether to melt the tether and detach the tether from the implant, applying thermal input to a bimetallic actuator to remove a securing member from engagement with the tether and detach the tether from the implant, applying thermal input to a shape memory actuator releasably coupled to the implant to move a portion of the shape memory actuator relative to the implant to disengage from the tether and detach the tether from the implant, applying thermal input to a shape memory actuator, the shape memory actuator being mounted to a cutting structure that at least partially surrounds the tether, wherein the thermal input moves the shape memory actuator and the cutting structure to cut the tether and detach the tether from the implant, and/or applying thermal input to a phase change assembly resulting in detaching of the tether from the implant.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

What is claimed is:

1. A system for treating a hole defined in a tissue structure between a left atrium and a right atrium of a heart, the hole defining an axis oriented axially through the hole, the system comprising:
   a handle body;
   a catheter coupled to said handle body;
   a tip portion extending from a distal end of said catheter;
   a tether system coupled to said handle body and extending through said catheter, said tether system including a first tether and a second tether, the first and second tethers each including a coil defining a lumen with a first wire and a second wire each extending through the lumen of the coil; and
   a medical device including a frame, said frame configured to assume a substantially flat configuration oriented substantially parallel to, or extending substantially along, the axis of the hole while in an intended, as-deployed state within the tissue structure, said frame including a central portion with at least a distal anchor and a first proximal anchor and a second proximal anchor extending from said central portion, each of said distal anchor, said first proximal anchor and said second proximal anchor configured to extend substantially coplanar with said central portion, said distal anchor configured to extend in the left atrium and said first and second proximal anchors configured to extend in the right atrium, said first proximal anchor configured to be directly coupled to said first tether and said second proximal anchor configured to be directly coupled to said second tether, said first and second proximal anchors configured to deflect proximally and continually extend substantially coplanar with said central portion as the tip portion moves distally over the first and second tethers toward the first and second proximal anchors;

wherein the second wire includes a loop and the first wire is configured to engage with the loop of the second wire to couple the medical device and maintain the medical device taut against the coil.

2. The system of claim 1, wherein said distal anchor, said first proximal anchor and said second proximal anchor are maintained substantially coplanar with said central portion in a non-deployed, constricted state within said tip portion of said catheter.

3. The system of claim 1, wherein said tether system further comprises a third tether, said third tether directly coupled to said central portion to facilitate moving said medical device between a constricted configuration and an expanded configuration.

4. The system of claim 3, wherein said first tether and said second tether are configured to facilitate deflection of said first and second proximal anchors in a proximal direction when moving said medical device from a deployed configuration to an undeployed configuration within said tip portion such that said first proximal anchor and said second proximal anchor enter said tip portion before said central portion enters said tip portion.

5. The system of claim 1, wherein said first and second proximal anchors and said central portion maintain said substantially flat configuration when moving said medical device between a deployed configuration and an undeployed configuration.

6. The system of claim 1, wherein the medical device comprises a tissue growth promoting member attached to said frame.

7. The system of claim 6, wherein said tissue growth promoting member is attached to said frame such that said tissue growth promoting member extends substantially out of plane relative to said substantially flat configuration of said frame.

8. The system of claim 1, wherein said medical device comprises a tissue growth promoting member attached to said frame, said tissue growth promoting member including a length dimension, a width dimension and a height dimension, the length dimension and the height dimension configured to extend substantially transverse to the axis of the hole and the width dimension configured to have at least one portion extending substantially parallel to the axis of the hole, the height dimension of the tissue growth promoting member configured to extend substantially out of plane relative to said substantially flat configuration of said frame, and the length dimension and the height dimension being substantially different from one another.

9. The system of claim 8, wherein the width dimension is smaller than the height dimension.

10. The system of claim 1, wherein said medical device comprises a tissue growth promoting member attached to said frame, said tissue growth promoting member having an elongated structure configured to be oriented substantially transverse to the axis of the hole and configured to be oriented across a width of the hole, said elongated structure having a height dimension configured to extend substantially out of plane relative to said substantially flat configuration of said frame to be in contact with the tissue structure.

11. The system of claim 1, wherein said medical device comprises a tissue growth promoting member attached to said frame, said tissue growth promoting member comprises a polyurethane foam.

12. The system of claim 1, wherein said medical device comprises a tissue growth member having an elongated structure, the elongated structure configured to be oriented on the medical device so as to be transverse to the axis of the hole and extend across an entire width of the hole in the tissue structure.

13. The system of claim 1, wherein the first proximal anchor and the second proximal anchor each define an eyelet, each eyelet configured to receive the loop of the second wire with the first wire extending through the loop to facilitate a locking arrangement between the tether system and the medical device.

14. The system of claim 1, wherein the loop of the second wire extends through an aperture defined in the medical device.

15. The system of claim 1, wherein the coil comprises a polymeric material formed thereon.

16. The system of claim 1, wherein, upon release of the medical device from the first and second tethers, the first wire is configured to be moved from the loop of the second wire.

17. The system of claim 1, wherein the coil is configured to effectively push the medical device to move the medical device from a constricted state within the tip portion to the intended, as deployed state.

18. The system of claim 1, wherein the first wire and the second wire are configured to effectively pull the medical device to move the medical device from the deployed state to a constricted state within the tip portion.

* * * * *